United States Patent
Almansa et al.

[11] Patent Number: 5,554,624
[45] Date of Patent: Sep. 10, 1996

[54] IMIDAZOPYRIDINE DERIVATIVES AS ANGIOTENSIN II ANTAGONISTS

[75] Inventors: Carmen Almansa; Elena Carceller; Concepcion Gonzalez, all of Barcelona; Carmen Torres, Badalona; Javier Bartroli, Barcelona, all of Spain

[73] Assignee: J. Uriach & Cia., Spain

[21] Appl. No.: 393,981

[22] Filed: Feb. 24, 1995

[30] Foreign Application Priority Data

Feb. 24, 1994 [ES] Spain ..................... 94-00364

[51] Int. Cl.$^6$ ............ A61K 31/435; C07D 471/04
[52] U.S. Cl. ............... 514/303; 546/23; 546/118
[58] Field of Search ............ 546/23, 118; 514/303

[56] References Cited

U.S. PATENT DOCUMENTS 5,240,938  8/1993  Greenlee et al. .............. 514/303

FOREIGN PATENT DOCUMENTS

| | | |
|---|---|---|
| 400974 | 12/1990 | European Pat. Off. . |
| 4142366 | 6/1993 | Germany . |
| 91/11999 | 8/1991 | WIPO . |

OTHER PUBLICATIONS

Wexler, R. R., et al., *American Journal of Hypertension*, vol. 5 (1992), 209S–220S.

*Primary Examiner*—Bernard Dentz

*Attorney, Agent, or Firm*—Rothwell, Figg, Ernst & Kurz p.c.

[57] ABSTRACT

The present invention relates to new imidazopyridine derivatives of formula I

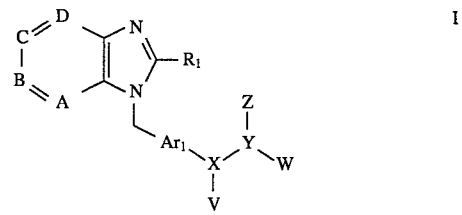

wherein: one of A, B, C and D is N and the other are CR, wherein each R independently represents hydrogen, $C_{1-4}$ alkyl, COOH or halogen; $R_1$ represents $C_{1-4}$ alkyl or $C_{3-7}$ cycloalkyl; $Ar_1$ represents phenyl or pyridyl which can be optionally substituted; V represents $C_{1-4}$ alkyl, $C_{3-7}$ cycloalkyl, aryl, aryl-$(C_{1-4})$alkyl or a 5- or 6-membered aromatic heterocycle; the group X-Y represents C=C or CH—$CR_3$; $R_3$ represents hydrogen, $C_{1-4}$ alkyl or aryl-$(C_{1-4})$alkyl; Z represents among others —$CO_2R_4$, —tetrazol-5-yl, —$CONHSO_2R_4$, —$CONR_4R_5$, —$CH_2NHSO_2R_4$; $R_4$ and $R_5$ independently represent hydrogen, $C_{1-4}$ alkyl, aryl, aryl-$(C_{1-4})$alkyl or perfluoro-$(C_{1-4})$alkyl; W represents hydrogen, cyano, $C_{1-4}$ alkyl, $C_{1-4}$ haloalkyl, $C_{3-7}$ cycloalkyl, aryl, aryl-$(C_{1-4})$alkyl, $C_{1-4}$ alkylsulfonyl, $C_{1-4}$ alkylsulfinyl, $C_{1-4}$ alkylthio, $C_{1-4}$ alkoxy, $C_{1-4}$ alkylcarbonyl, halogen, hydroxymethyl or $C_{1-4}$ alkoxymethyl, or W can have any of the meanings disclosed for Z. These compounds are angiotensin II antagonists.

21 Claims, No Drawings

IMIDAZOPYRIDINE DERIVATIVES AS ANGIOTENSIN II ANTAGONISTS

FIELD OF THE INVENTION

The present invention relates to new imidazopyridine derivatives which are potent angiotensin II antagonists. The invention also relates to a process for their preparation, to the pharmaceutical compositions containing them and to their use in the treatment of hypertension, congestive heart failure, elevated intraocular pressure and other diseases or medical conditions in which the action of angiotensin II is implicated.

DESCRIPTION OF THE PRIOR ART

The renin-angiotensin system (RAS) plays a key role in the regulation of blood pressure and volume homeostasis. Activation of the renin-angiotensin cascade begins with renin secretion front the juxtaglomerular apparatus of the kidney and culminates in the formation of the octapeptide angiotensin II.

Angiotensin II exerts its biological effects via interactions with specific receptors present in many tissues. Two basic types of angiotensin II receptors have been characterized so far, both with a broad distribution: the $AT_1$ receptors, responsible for the majority of effects attributed to this peptide, and the $AT_2$ receptors, the functional role of which has not yet been identified.

The main effects of angiotensin II are the regulation of blood pressure through vasoconstriction thereby effecting an increase in vascular resistances, the regulation of volemia through the stimulation of the release of vasopressin and particularly aldosterone, which induces saline retention, and the regulation of the adrenocorticotropic hormone (ACTH). Angiotensin II can act as a neuropeptide at the central nervous system and can play a modulating function in the release of other neurotransmitters.

Furthermore, it has been described that the administration of angiotensin II to either the rat brain dorsal neostriatum or the lateral ventricle produces alterations in the rat cognitive responses. This fact suggests that probably angiotensin II is involved in several cerebral processes related with the learning function, memory and the like.

One of the possible modes of interfering with the RAS is to block the action of angiotensin II at the receptor level. Although several peptidic analogues of angiotensin II having greater affinity for its receptors than angiotensin II itself have been discovered, their therapeutic use has been severely limited by their lack of bioavailability and short duration of action.

More recently, several nonpeptide angiotensin II receptor antagonists have been reported in the literature (Rationale for the chemical Development of Angiotensin II Receptor Antagonists, Wexler et al., *Am. J. Hypertens.*, 5: 209S–220S, 1992). Patent applications EP 400974 and WO 9111999 disclose imidazopyridine-derived compounds related to those described in the present invention.

DESCRIPTION OF THE INVENTION

The present invention relates to novel imidazopyridines of general formula I:

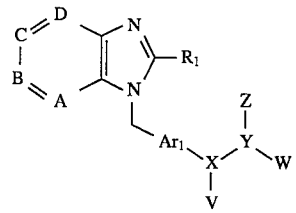

wherein:
one of A, B, C and D is N and the other are CR, wherein each R independently represents hydrogen, $C_{1-4}$ alkyl, COOH or halogen;

$R_1$ represents $C_{1-4}$ alkyl or $C_{3-7}$ cycloalkyl;

$Ar_1$ represents phenyl or pyridyl which can be optionally substituted with a group $C_{1-4}$ alkyl, $C_{1-4}$ alkoxy, halogen, nitro, amino, $C_{1-4}$ alkylamino or $C_{1-4}$ dialkylamino;

V represents $C_{1-4}$ alkyl, $C_{3-7}$ cycloalkyl, aryl, aryl-(C1-4)alkyl or a 5- or 6-membered aromatic heterocycle, in which from 1 to 3 of the ring atoms are nitrogen and/or oxygen and/or sulphur, said heterocycle being unsubstituted or having one or more substituents $R_2$;

aryl represents phenyl or phenyl substituted with one or more groups $R_2$;

$R_2$ represents $C_{1-4}$ alkyl, $C_{1-4}$ haloalkyl, $C_{1-4}$ alkoxy, $C_{1-4}$ haloalkoxy, halogen, nitro, cyano, hydroxy, amino, $C_{1-4}$ alkylamino, $C_{1-4}$ dialkylamino;

the group X-Y represents C=C or CH—$CR_3$;

$R_3$ represents hydrogen, $C_{1-4}$ alkyl or aryl-($C_{1-4}$)alkyl;

Z represents —$CO_2R_4$; -tetrazol-5-yl; tetrazol-5-ylmethyl; —CONH(tetrazol-5-yl); —$CONHSO_2R_4$; —$CONHSO_2$-Het; —$CONHOR_4$; —$CONR_4R_5$; —$COCH_2COR_4$; —$COCH_2CO_2R_4$; —$CONHNHSO_2R_4$; —$CONHNHCONH_2$; —$CH_2NHSO_2R_4$; —$CH_2CO_2R_4$; —$CH_2SO_2NHCOR_4$; —$CH_2SO_2NHCONHR_4$; —$CH_2CONHSO_2R_4$; —$CH_2SO_2NH$-Het; —$CH_2NHCOR_4$; —$NHSO_2R_4$; —$NHCOR_4$; —$NHCONHSO_2R_4$; —$NHSO_2NHCOR_4$; —$NHCONR_4SO_2CH_2R_4$; —$SO_3H$; —$SO_2NHR_4$; —$SO_2NHCONR_4R_5$; —$SO_2NHCO_2R_4$; —$SO_2N(CO_2R_4)_2$; —$SO_2NHCOR_4$; —$SO_2NH$—Het; —$SO_2NHCHO$-Het; —$PO(OH)_2$; —$PO(OR_4)_2$; —$PO(OH)(OR_4)$; 3-(trifluoromethyl)-1,2,4-triazol-5-yl; or a group of formula

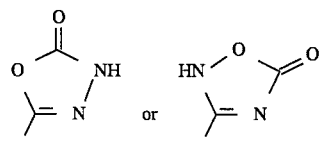

wherein Het represents a 5- or 6-membered aromatic heterecycle in which from 1 to 3 of the ring atoms are nitrogen and/or oxygen and/or sulphur and which can be optionally substituted with one or two groups chosen from hydroxy, mercapto, $C_{1-4}$ alkyl, $C_{1-4}$ alkoxy, halogen, nitro, $CO_2H$, $CO_2C_{1-4}$ alkyl, amine, $C_{1-4}$ alkylamino and $C_{1-4}$ dialkylamino; and $R_4$ and $R_5$ independently represent hydrogen, $C_{1-4}$ alkyl, aryl, aryl-($C_{1-4}$)alkyl or perfluoro-($C_{1-4}$)alkyl;

W represents hydrogen, cyano, $C_{1-4}$ alkyl, $C_{1-4}$ haloalkyl, $C_{3-7}$ cycloalkyl, aryl, aryl-($C_{1-4}$)alkyl, $C_{1-4}$ alkylsulfonyl, $C_{1-4}$ alkylsulfinyl, $C_{1-4}$ alkylthio, $C_{1-4}$ alkoxy, $C_{1-4}$ alkylcarbonyl, halogen, hydroxymethyl or $C_{1-4}$ alkoxymethyl, or W can have any of the meanings disclosed for Z;

and the salts and solvates thereof.

The present invention also provides pharmaceutical compositions which comprise an effective amount of a compound of formula I or a pharmaceutically acceptable salt or solvate thereof in admixture with a pharmaceutically acceptable excipient.

The invention further provides the use of a compound of formula I or a pharmaceutically acceptable salt or solvate thereof in the treatment or prevention of diseases or medical conditions in which angiotensin II is involved, such as hypertension, congestive heart failure and elevated intraocular pressure. Accordingly, the present invention provides a method of inhibiting the effects (particularly undesirable physiological effects) of angiotensin II in a mammal, which comprises administering to said mammal an angiotensin II-inhibiting amount of a compound of formula I or a pharmaceutically acceptable salt or solvate thereof. Preferred is a method of treating or preventing hypertension, congestive heart failure and elevated intraocular pressure in a mammal in need thereof, the method comprising administering to the mammal an effective amount of a compound of formula I, or a pharmaceutically acceptable salt or solvate thereof.

The invention still further provides a process for preparing a compound of formula I, which comprises:

(a) reacting a compound of formula VII

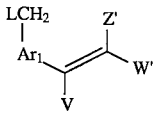

VII wherein L represents a halogen atom such as chlorine or bromine, Z' represents a group Z or a group convertible thereto by known chemical reactions, W' represents a group W or a group convertible thereto by known chemical reactions, and $Ar_1$ and V have the previously defined meaning, with a compound of formula VIII

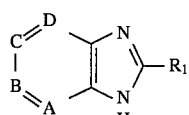

VIII wherein A, B, C, D and $R_1$ have the previously defined meaning, in the presence of a base; or (b) reducing a compound of formula IX

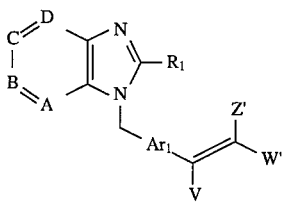

IX wherein A, B, C, D, $Ar_1$, V, $R_1$, Z' and W' have the previously defined meaning, with hydrogen in the presence of a catalyst or with a metallic hydride; or (c) reacting a compound of formula XIII

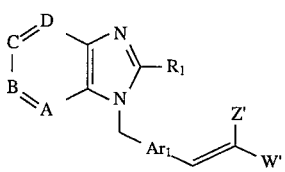

XIII wherein A, B, C, D, $Ar_1$, $R_1$, Z' and W' have the previously defined meaning, with an alkylmagnesium halide of formula VMgHal (XIV, wherein V has the previously defined meaning); or (d) converting a compound of general formula I into another compound of general formula I; and (e) optionally after step (a) or step (b) or step (c), converting the groups Z' and/or W' into the groups Z and/or W; and (f) optionally, reacting a compound of formula I with an acid or a base to give the corresponding salt.

In the above definitions, the term $C_{1-4}$ alkyl means a linear or branched alkyl chain containing from 1 to 4 carbon atoms. It includes methyl, ethyl, propyl, isopropyl, butyl, isobutyl, sec-butyl and tert-butyl.

A $C_{1-4}$ alkoxy group means a group derived from the union of a $C_{1-4}$ alkyl group to an oxygen atom of an ether functional group. Examples include methoxy, ethoxy, propoxy, isopropoxy, butoxy, isobutoxy, sec-butoxy and tert-butoxy.

A halogen atom means a fluorine, chlorine, bromine or iodine atom.

A $C_{3-7}$ cycloalkyl group represents cyclopropyl, cyclobutyl, cyclopentyl, cyclohexyl or cycloheptyl.

A $C_{1-4}$ haloalkyl group means a group resulting from the substitution of one or more hydrogen atoms of a $C_{1-4}$ alkyl group by one or more halogen atoms (i.e. fluorine, chlorine, bromine or iodine), which can be the same or different. Examples include trifluoromethyl, fluoromethyl, chloroethyl, fluoroethyl, iodoethyl, pentafluoroethyl, fluoropropyl, chloropropyl, 2,2,3,3,3-pentafluoropropyl, heptafluoropropyl, fluorobutyl, and non-fluorobutyl.

A perfluoro-($C_{1-4}$)alkyl group means a group resulting from the substitution of all hydrogen atoms of a $C_{1-4}$ alkyl group by fluorine atoms. Examples include trifluoromethyl, pentafluoroethyl, heptafluoropropy and nonafluorobutyl.

A $C_{1-4}$ alkylcarbonyl group means a group resulting from the union of a $C_{1-4}$ alkyl group to a carbonyl group. Examples include the groups acetyl, propionyl, isopropionyl, and butanoyl.

A $C_{1-4}$ alkylsulfonyl group means a group resulting from the union of a $C_{1-4}$ alkyl group to a sulfonyl group. Examples include methylsulfonyl, ethylsulfonyl, propylsulfonyl, isopropylsulfonyl, butylsulfonyl, isobutylsulfonyl, sec-butylsulfonyl, and tert-butylsulfonyl.

A $C_{1-4}$ alkylsulfinyl group means a group resulting from the union of a $C_{1-4}$ alkyl group to a sulfinyl group. Examples include methylsulfinyl, ethylsulfinyl, propylsulfinyl, isopropylsulfinyl, butylsulfinyl, isobutylsulfinyl, sec-butylsulfinyl, and tert-butylsulfinyl.

A $C_{1-4}$ alkylthio group means a group resulting from the union of a $C_{1-4}$ alkyl group to a sulphur atom of a thioether functional group. Examples include methylthio, ethylthio, propylthio, isopropylthio, butylthio, isobutylthio, sec-butylthio, and tert-butylthio.

A $C_{1-4}$ alkylamino or $C_{1-4}$ dialkylamino group represents a group resulting from the substitution of one or two hydrogen atoms, respectively, of an amino group by one or two $C_{1-4}$ alkyl groups, which can be the same or different. Examples include methylamino, dimethylamino, ethylamino, diethylamino, ethylmethylamino, propylamino, dipropylamino, isopropylamino and diisopropylamino.

In the compounds where V represents a 5- or 6-membered aromatic heterocyclic group, from 1 to 3 of the ring atoms are nitrogen and/or oxygen and/or sulphur, and said heterocycle can be unsubstituted or substituted with one or more, preferably one or two, substituents $R_2$. Examples of said heterocycles include pyridine, pyrimidine, pyrazine, pyridazine, furan, pyrrole, thiophene, imidazole, triazole, thiazole, oxazole and isoxazole.

As examples of the group that defined above in connection with the substituent Z, we can mention the same heterocycles that have been listed in the preceding paragraph for group V.

In the compounds of the present invention, $Ar_1$ represents a phenyl or pyridyl group which can be unsubstituted or substituted with a group $C_{1-4}$ alkyl, $C_{1-4}$ alkoxy, halogen, nitro, amino, $C_1$ alkylamino or $C_{1-4}$ dialkylamino. The imidazopyridinemethyl moiety and the radical —X(V)—Y(Z)W attached to the $Ar_1$ ring can be in any available position of said ring and they can be in an ortho, meta or para relationship one to another, but it is preferred that they are in a meta or para relationship, and it is more preferred that they are in a para relationship. Thus, when it is stated below that the radical —X(V)—Y(Z)W is in the para position of the $AR_1$ ring, it is to be understood that this radical is in a para relationship with respect to the imidazopyridinemethyl moiety.

Preferred embodiments of the present invention are those compounds of formula I wherein:

$Ar_1$ represents phenyl which can be optionally substituted with a group $C_{1-4}$ alkyl, $C_{1-4}$ alkoxy, halogen, nitro, amino, $C_{1-4}$ alkylamino or $C_{1-4}$ dialkylamino;

the radical —X(V)—Y(Z)W is in the para position of the $AR_1$ ring; and

A, B, C, D, $R_1$, V, W, X, Y and Z have the previously defined meaning.

More preferred embodiments of the present invention are those compounds of formula I wherein:

$Ar_1$ represents phenyl which can be optionally substituted with a group $C_{1-4}$ alkyl, $C_{1-4}$ alkoxy, halogen, nitro, amino, $C_{1-4}$ alkylamino or $C_{1-4}$ dialkylamino;

the radical —X(V)—Y(Z)W is in the para position of the $Ar_1$ ring;

A is N;

B, C and D are each CR; and

R, $R_1$, V, W, X, Y and Z have the previously defined meaning.

Still more preferred embodiments of the present invention are those compounds of formula I wherein:

$AR_1$ represents phenyl which can be optionally substituted with a group $C_{1-4}$ alkyl, $C_{1-4}$ alkoxy, halogen, nitro, amino, $C_{1-4}$ alkylamino or $C_{1-4}$ dialkylamino;

the radical —X(V)—Y(Z)W is in the para position of the $AR_1$ ring;

A is N;

C is CH and B and D are each CR;

R represents hydrogen or $C_{1-4}$ alkyl; and $R_1$, V, W, X, Y and Z have the previously defined meaning.

Even more preferred embodiments of the present invention are those compounds of formula I wherein:

$Ar_1$ represents phenyl which can be optionally substituted with a group $C_{1-4}$ alkyl or halogen;

the radical —X(V)—Y(Z)W is in the para position of the $AR_1$ ring;

A is N;

C is CH and B and D are each CR;

R represents hydrogen or $C_{1-4}$ alkyl;

V represents $C_{1-4}$ alkyl, $C_{3-7}$ cycloalkyl, aryl, or aryl-($C_{1-4}$)alkyl; and $R_1$, W, X, Y and Z have the previously defined meaning.

Particularly preferred embodiments of the present invention are those compounds of formula I wherein:

$Ar_1$ represents phenyl which can be optionally substituted with a group $C_{1-4}$ alkyl or halogen;

the radical —X(V)—Y(Z)W is in the para position of the $Ar_1$ ring;

A is N;

C is CH and B and D are each CR;

R represents hydrogen or $C_{1-4}$ alkyl;

V represents $C_{1-4}$ alkyl, $C_{3-7}$ cycloalkyl, aryl, or aryl-($C_{1-4}$)alkyl;

Z represents —$CO_2R_4$; -tetrazol-5-yl, —$CONHSO_2R_4$, —$CONR_4R_5$, —$CH_2NHSO_2R_4$—, —$SO_2NHR_4$ or —$SO_2NHCOR_4$; and $R_1$, $R_4$, $R_5$, W, X and Y have the previously defined meaning.

Highly preferred embodiments of the present invention are the following groups of compounds:

I) Those compounds of formula I wherein:

$Ar_1$ represents phenyl which can be optionally substituted with a group $C_{1-4}$ alkyl or halogen;

the radical —X(V)—Y(Z)W is in the para position of the $AR_1$ ring;

A is N;

C is CH and B and D are each CR;

R represents hydrogen or $C_{1-4}$ alkyl;

V represents $C_{1-4}$ alkyl, $C_{3-7}$ cycloalkyl, aryl, or aryl-($C_{1-4}$)alkyl;

Z represents —$CO_2R_4$; -tetrazol-5-yl, —$CONHSO_2R_4$, —$CONR_4R_5$, —$CH_2NHSO_2R_4$, —$SO_2NHR_4$ or —$SO_2NHCOR_4$;

the group X—Y represents C=C;

W represents cyano, $C_{1-4}$ alkyl, aryl, aryl-($C_{1-4}$)alkyl, $C_{1-4}$ alkylsulfonyl, $C_{1-4}$ alkylsulfinyl, $C_{1-4}$ alkylthio, or halogen, or W can have any of the meanings disclosed for Z; and $R_1$, $R_4$ and $R_5$ have the previously defined meaning.

II) Those compounds of formula I wherein:

$AR_1$ represents phenyl which can be optionally substituted with a group $C_{1-4}$ alkyl or halogen;

the radical —X(V)—Y(Z)W is in the para position of the $Ar_1$ ring;

A is N;

C is CH and B and D are each CR;

R represents hydrogen or $C_{1-4}$ alkyl;

V represents $C_{1-4}$ alkyl, $C_{3-7}$ cycloalkyl, aryl, or aryl-($C_{1-4}$)alkyl;

Z represents —$CO_2R_4$; -tetrazol-5-yl, —$CONHSO_2R_4$, —$CONR_4R_5$, —$CH_2NHSO_2R_4$, —$SO_2NHR_4$ or —$SO_2NHCOR_4$;

the group X—Y represents CH—CH;

W represents hydrogen, $C_{1-4}$ alkyl, aryl, aryl-($C_{1-4}$)alkyl or halogen, or W can have any of the meanings disclosed for Z; and $R_1$, $R_4$ and $R_5$ have the previously defined meaning.

Most preferred embodiments of the present invention are those compounds of formula I wherein:

$Ar_1$ represents phenyl which can be optionally substituted with a group $C_{1-4}$ alkyl or halogen;

the radical —X(V)—Y(Z)W is in the para position of the $Ar_1$ ring;

A is N;

C is CH and B and D are each CR;

R represents hydrogen or $C_{1-4}$ alkyl;

V represents $C_{1-4}$ alkyl, $C_{3-7}$ cycloalkyl, aryl, or aryl-$(C_{1-4})$alkyl; Z represents —$CO_2R_4$; -tetrazol-5-yl, —$CONHSO_2R_4$, —$CONR_4R_5$, —$CH_2NHSO_2R_4$, —$SO_2NHR_4$ or —$SO_2NHCOR_4$;

the group X—Y represents CH=CH;

W represents $C_{1-4}$ alkyl, aryl, aryl-$(C_{1-4})$alkyl or halogen, or W can have any of the meanings disclosed for Z; and $R_1$, $R_4$ and $R_5$ have the previously defined meaning.

The formulae of some specific examples are shown below, together with the number corresponding to the example in which their preparation is described:

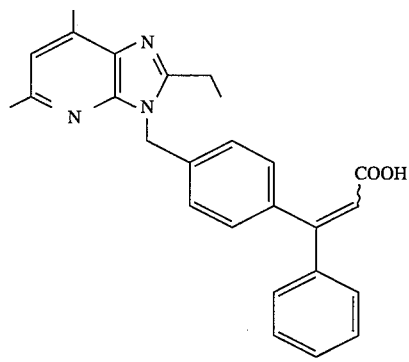

1

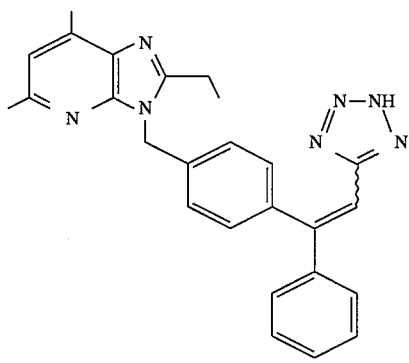

2

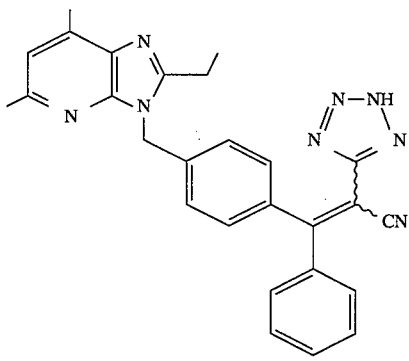

3

-continued

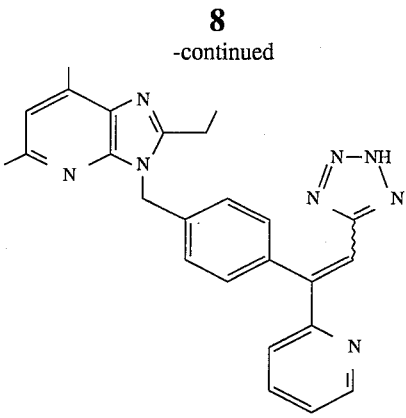

4

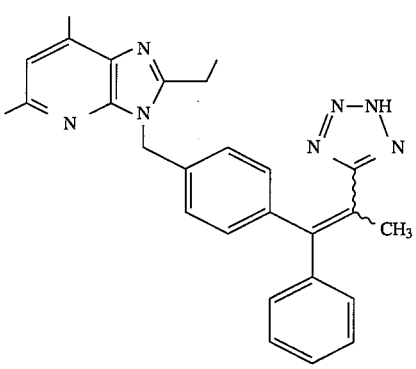

5

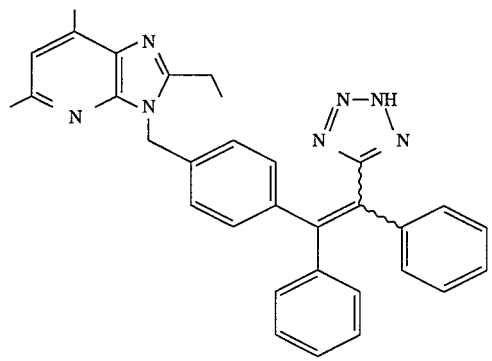

6

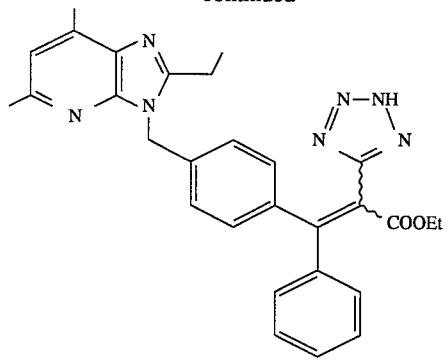
7
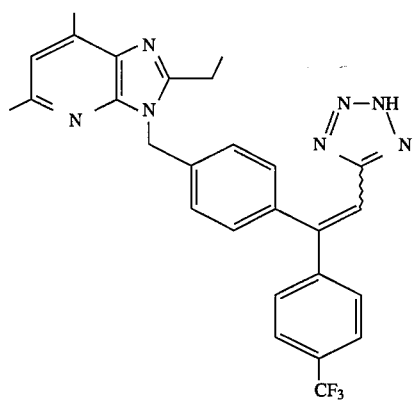
8
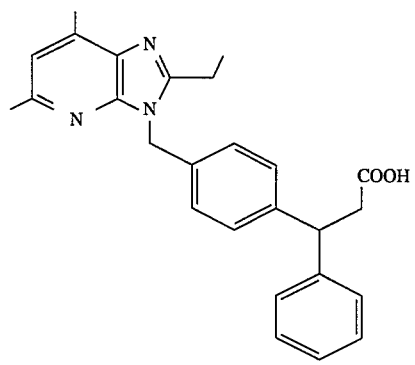
9
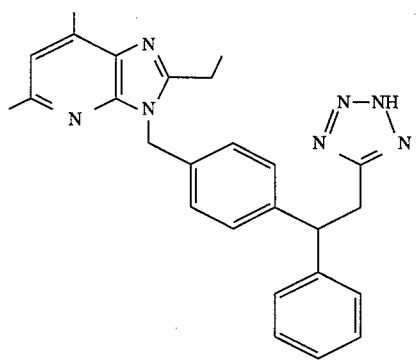
10
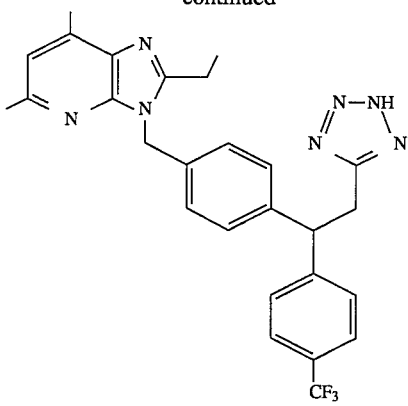
11
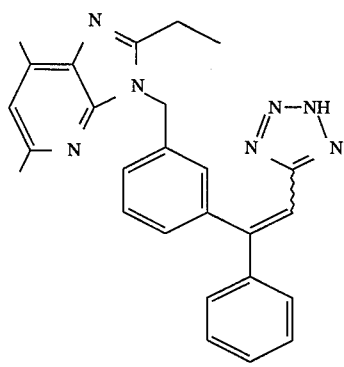
12
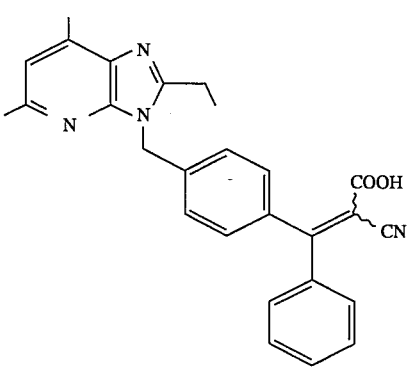
13
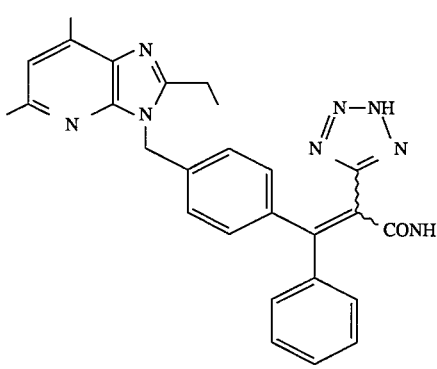
14

11
-continued
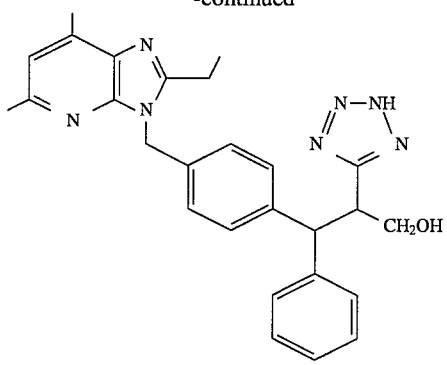
15
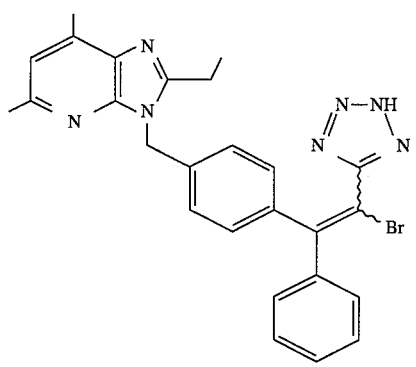
16
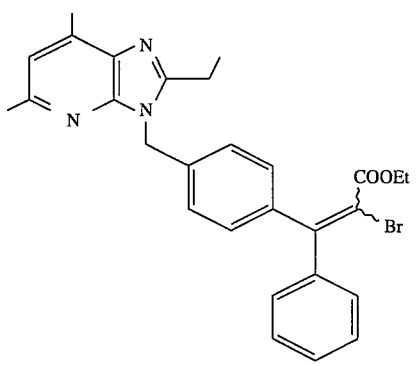
17
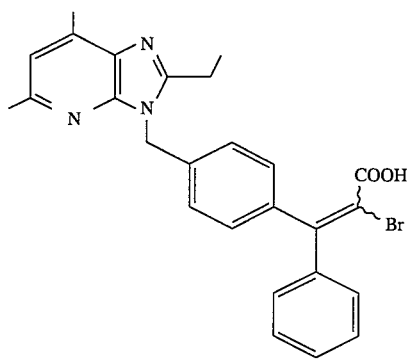
18
12
-continued
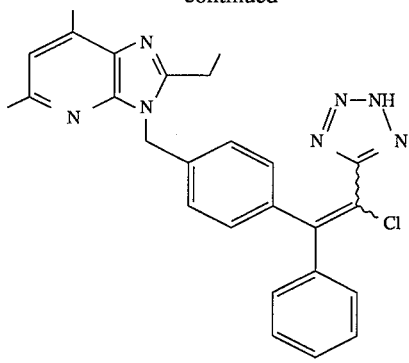
19
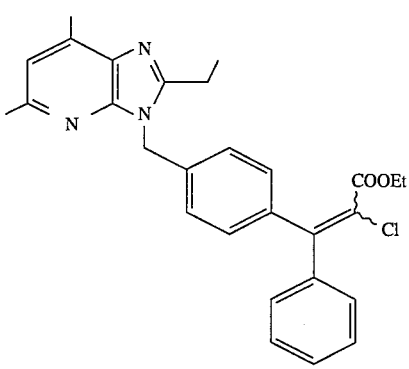
20
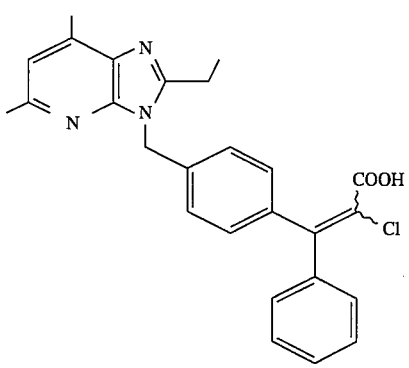
21
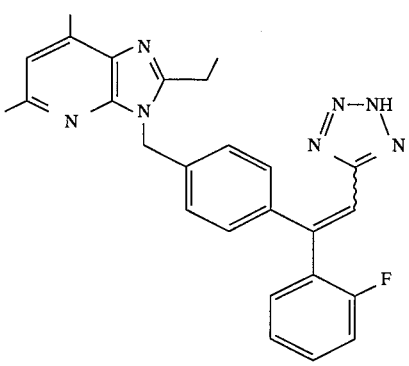
22

23
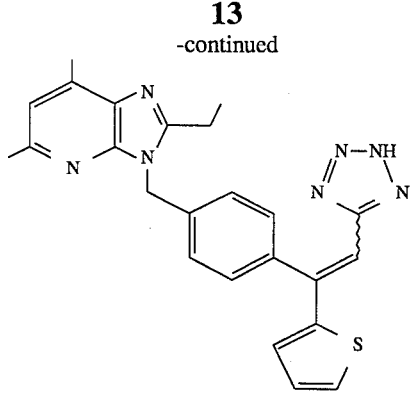
24
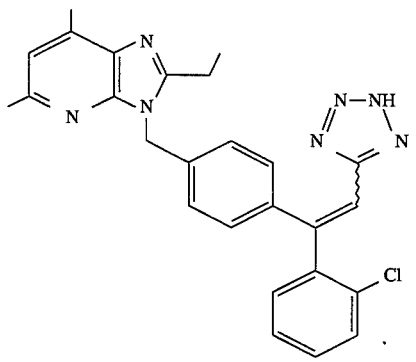
25
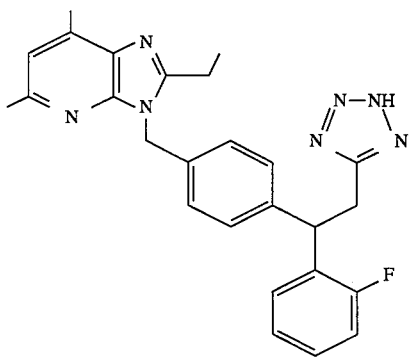
26
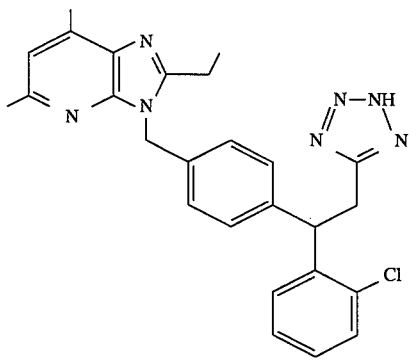
27
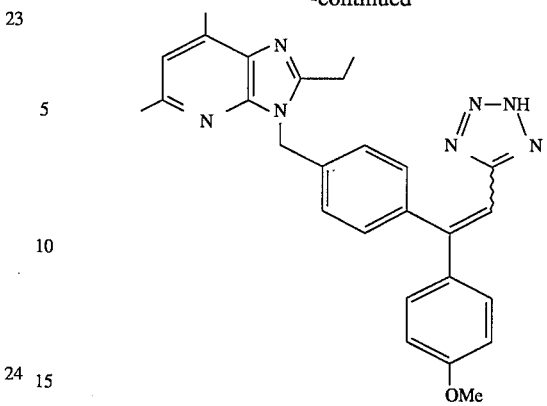
28
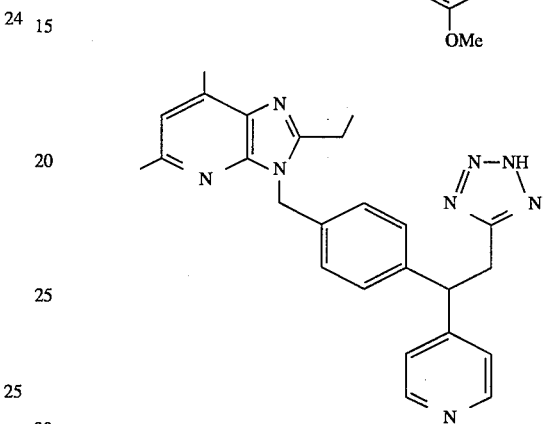
29
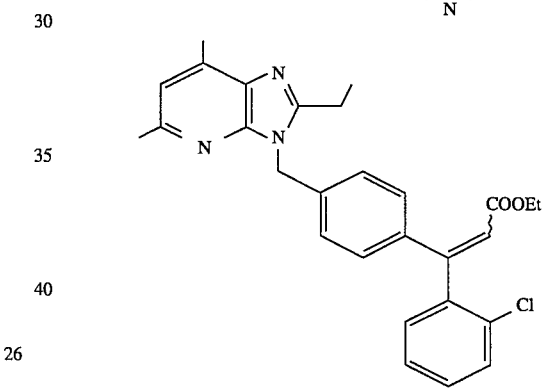
30
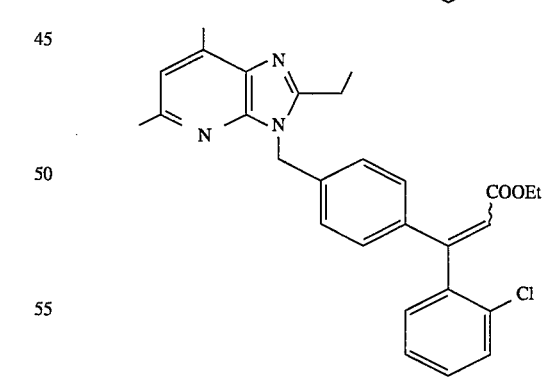

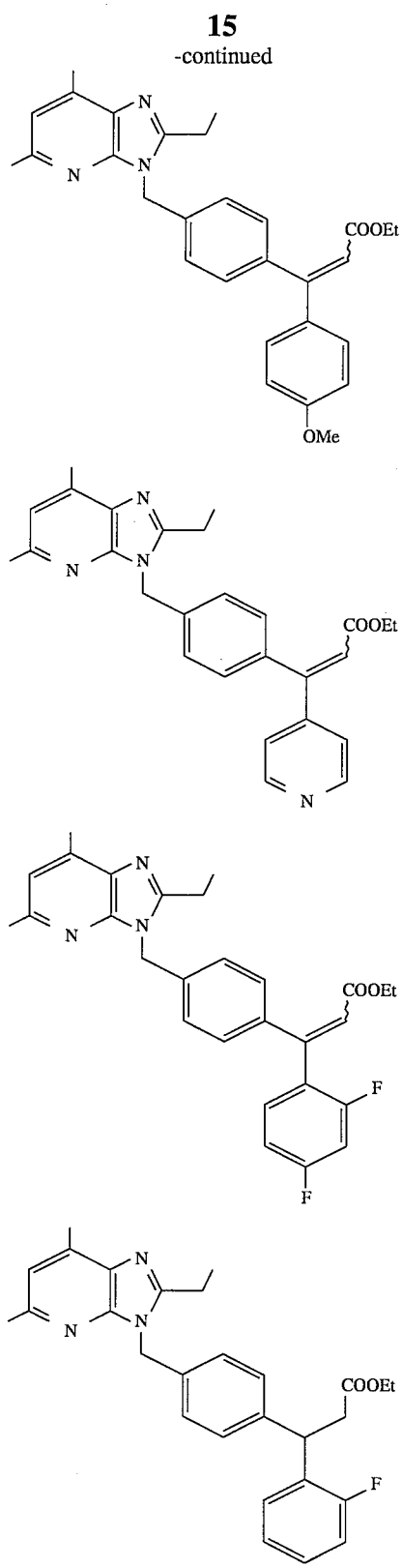
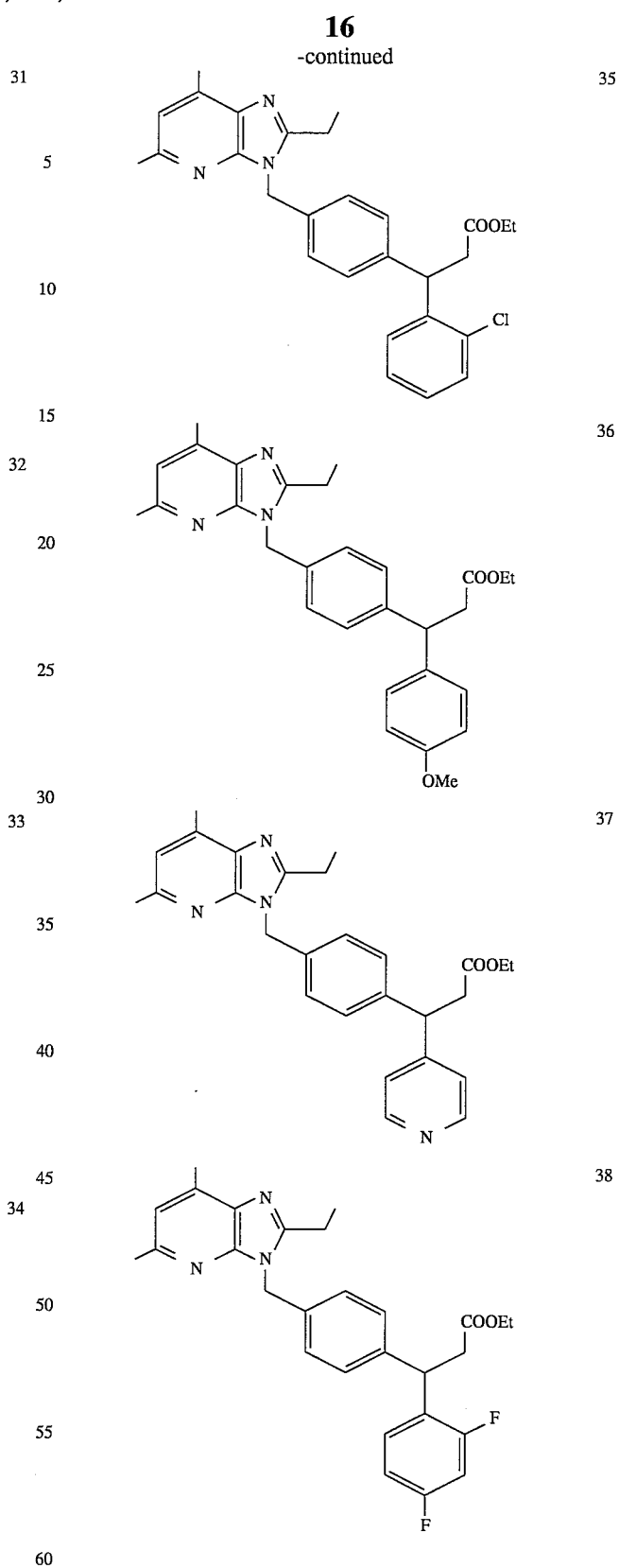

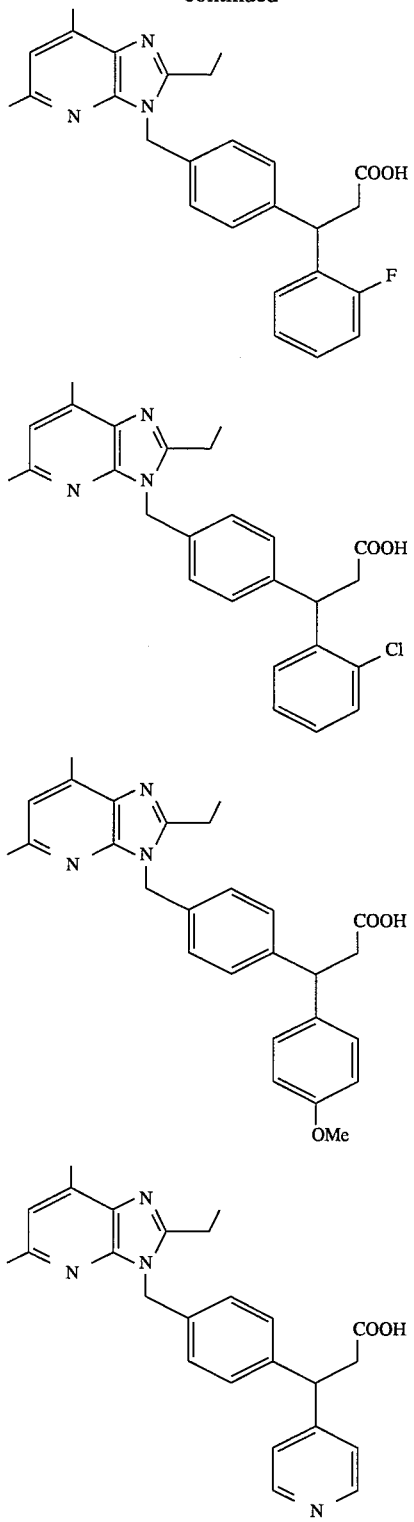
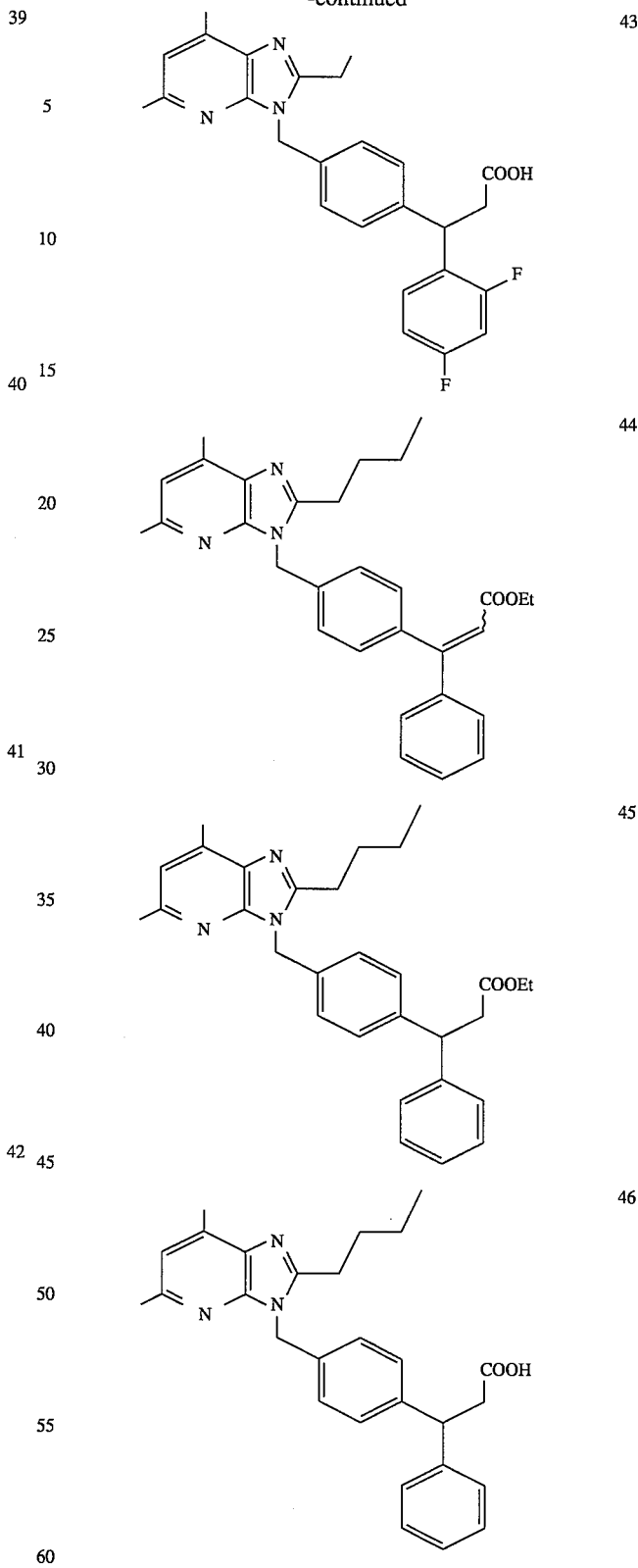

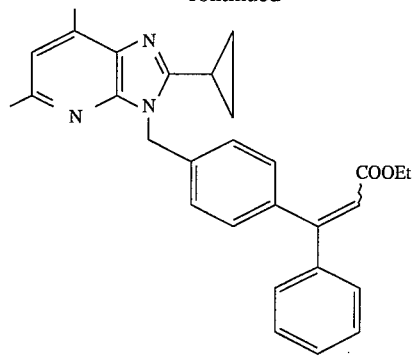
47
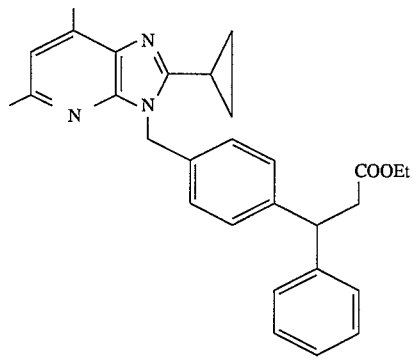
48
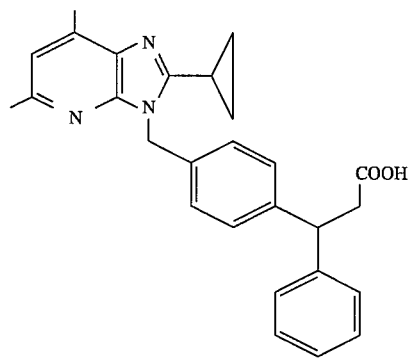
49
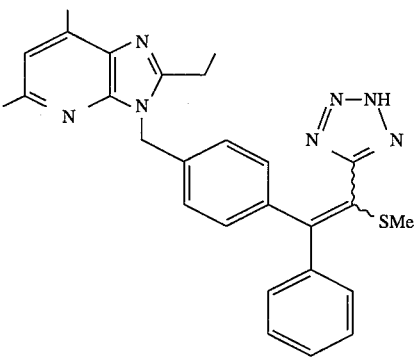
50
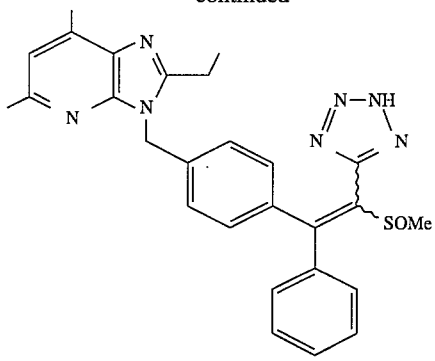
51
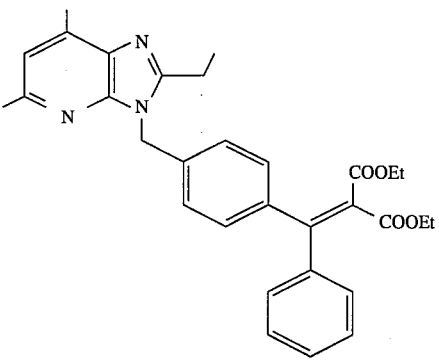
52
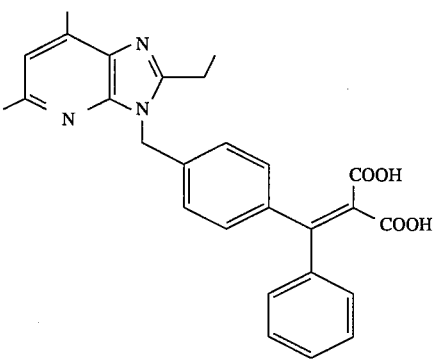
53
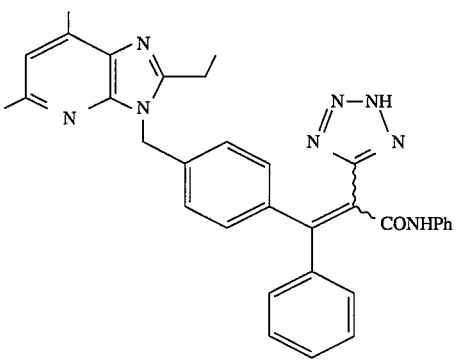
54

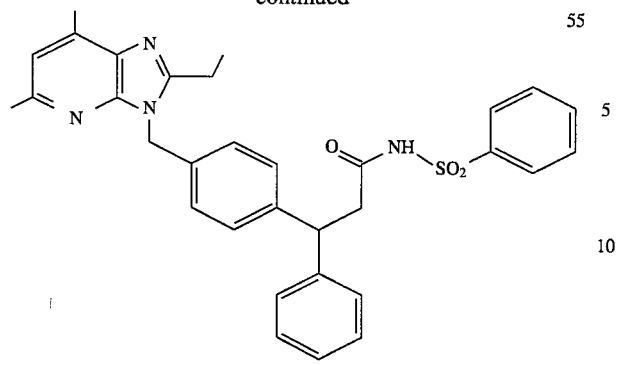
55
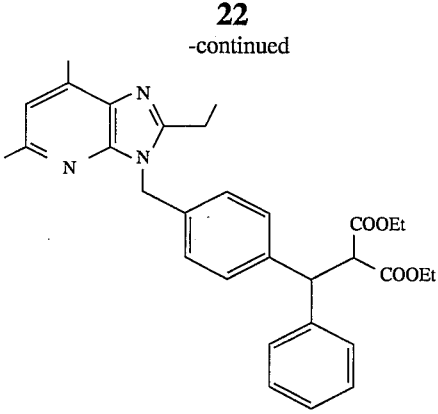
59
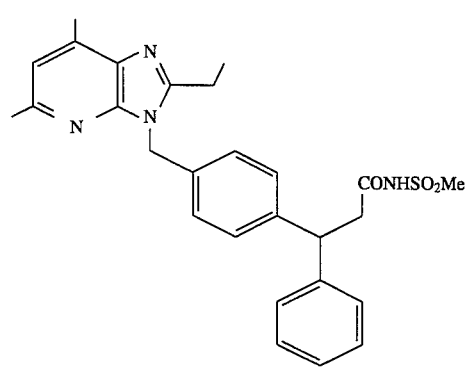
56
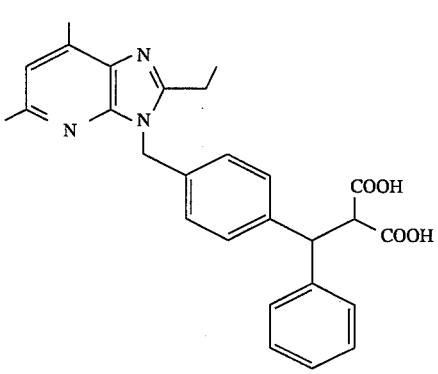
60
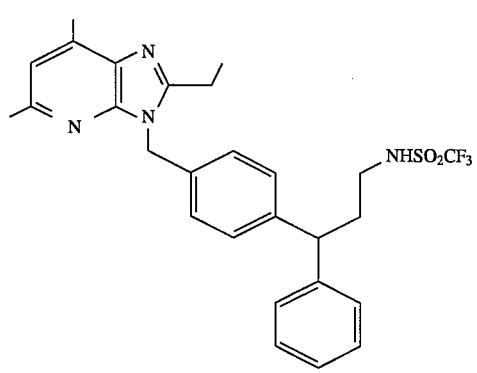
57
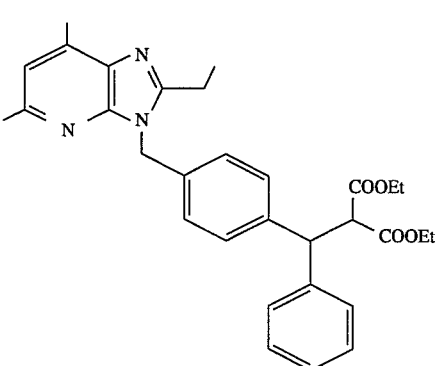
61
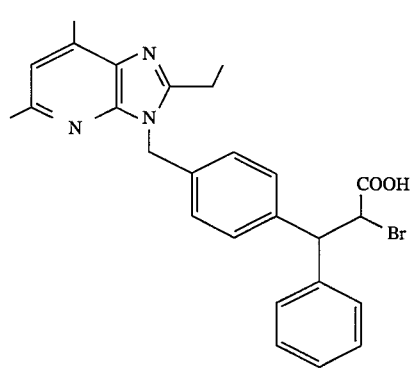
58
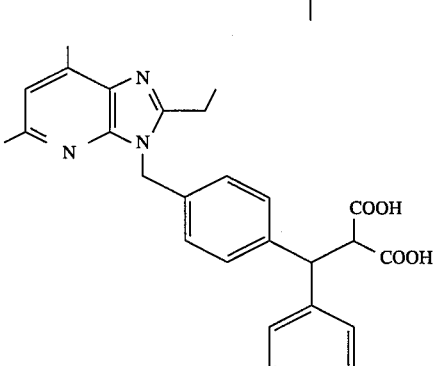
62

63
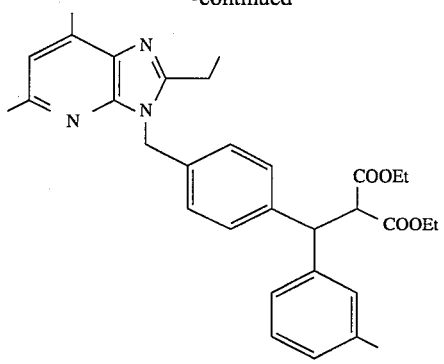
64
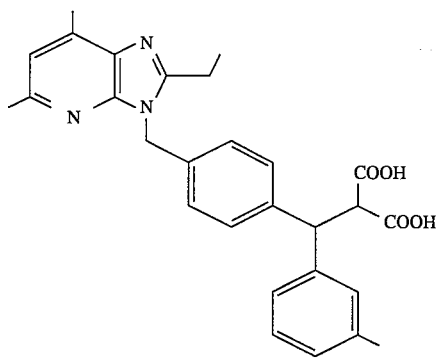
65
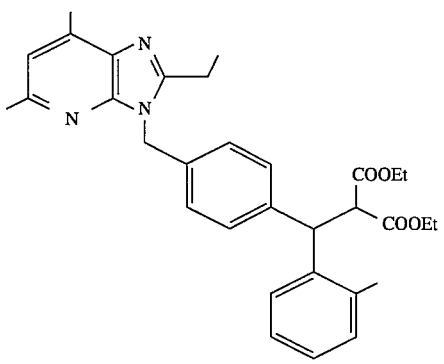
66
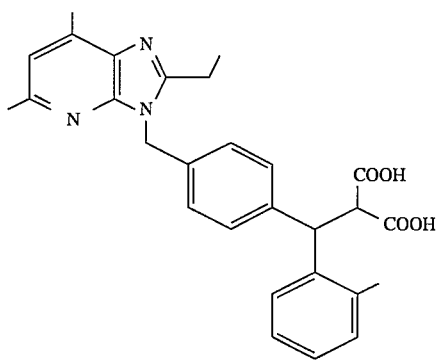
67
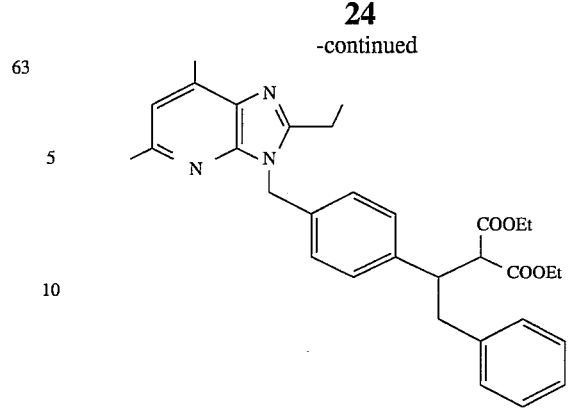
68
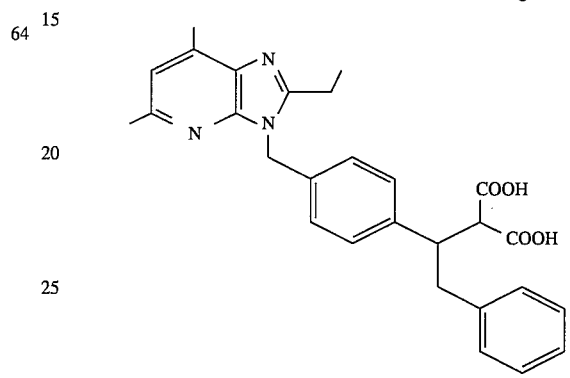
69
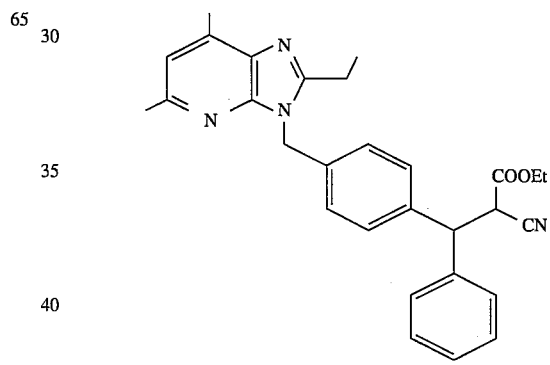
70
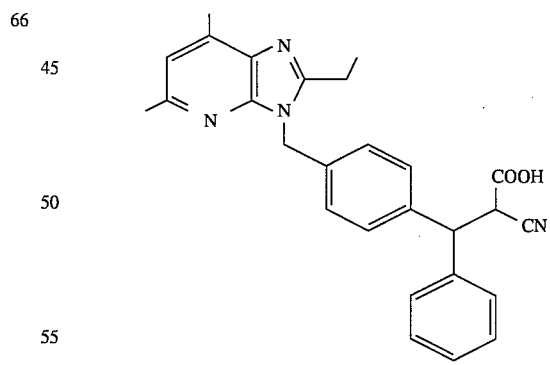

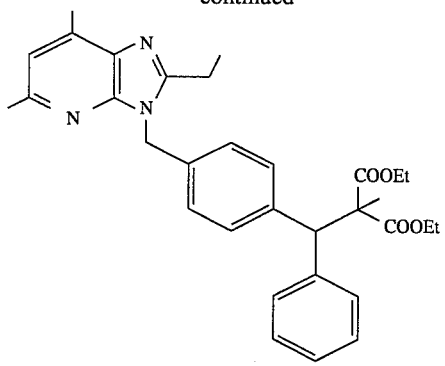# 71
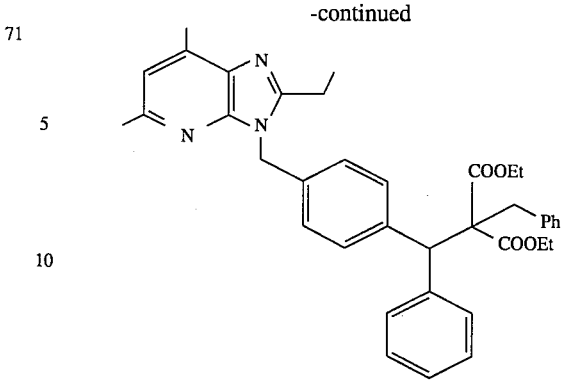# 75
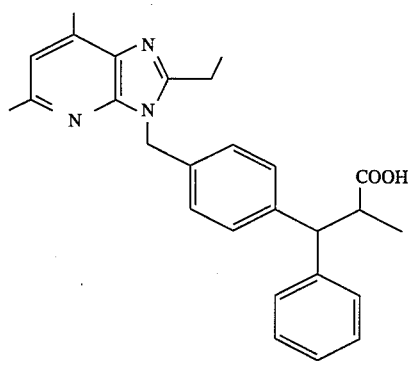# 72
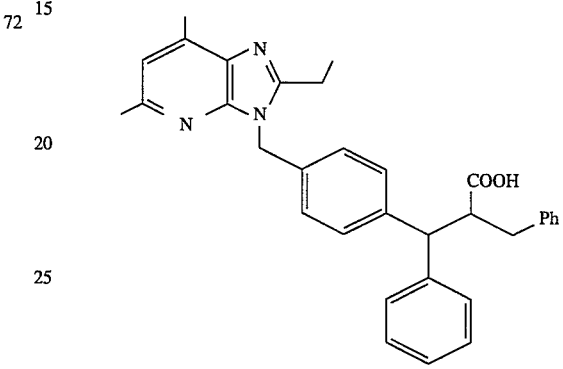# 76
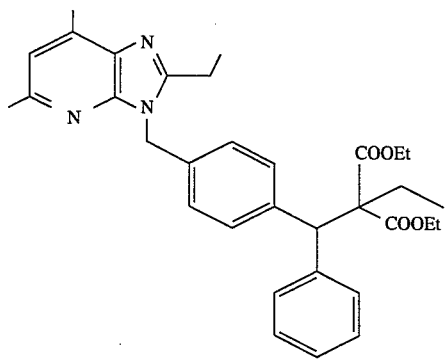# 73
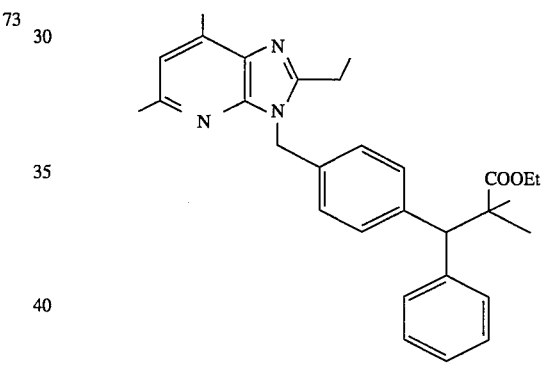# 77
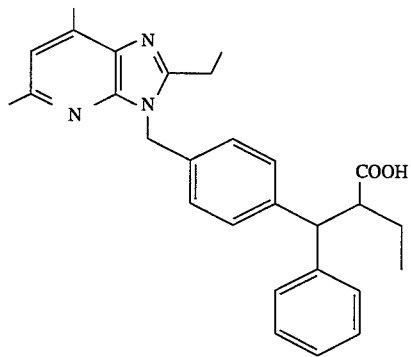# 74
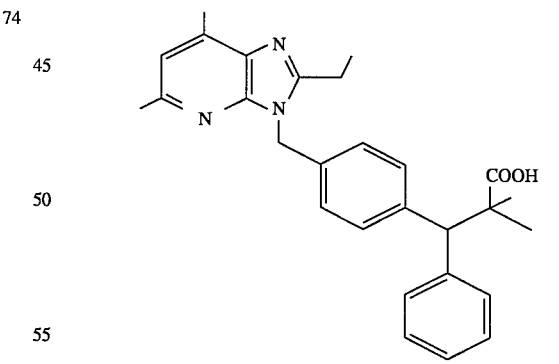# 78

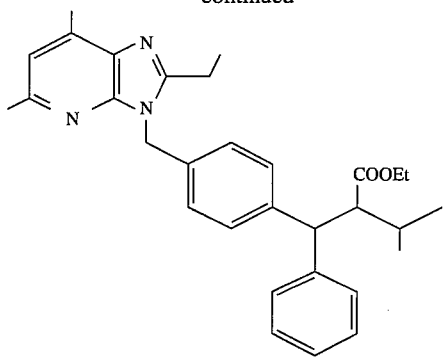
79
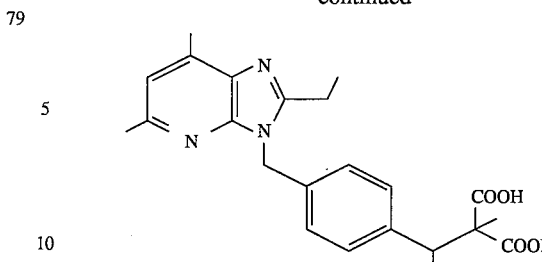
84
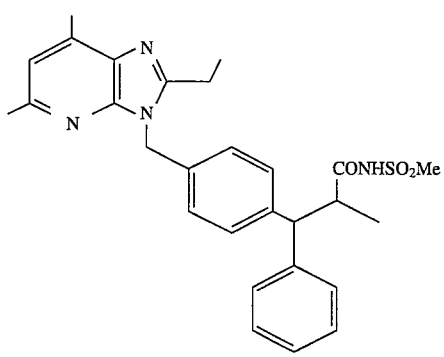
80
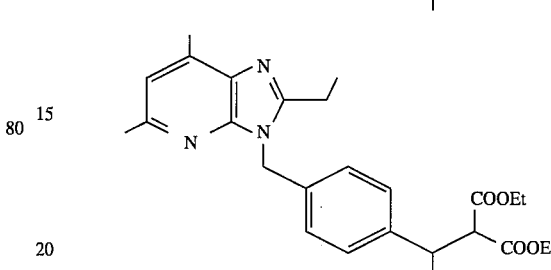
85
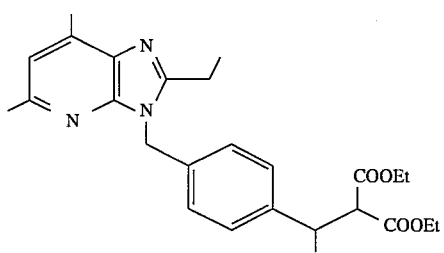
81
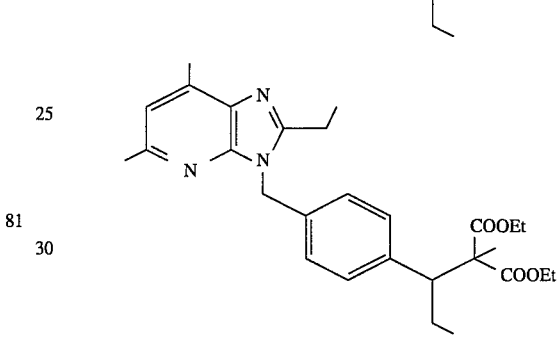
86
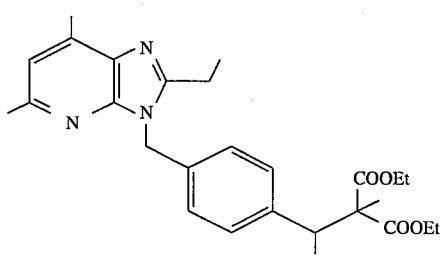
82
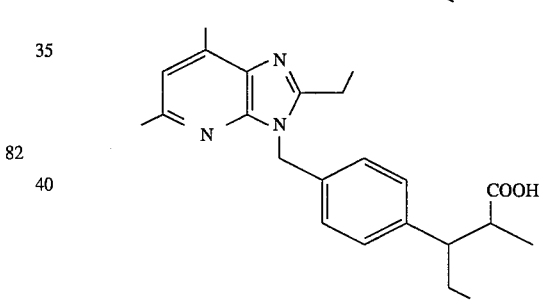
87
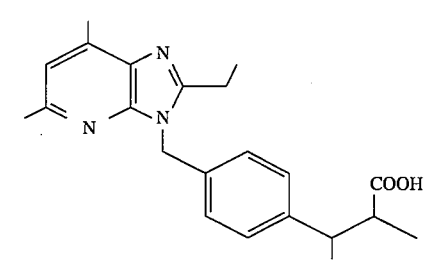
83
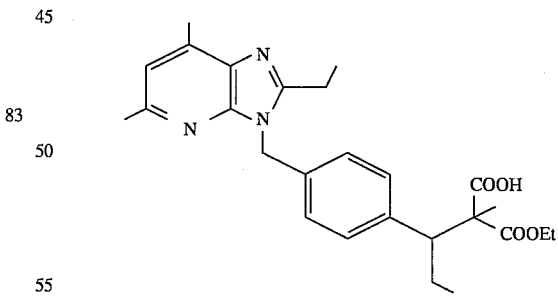
88

89

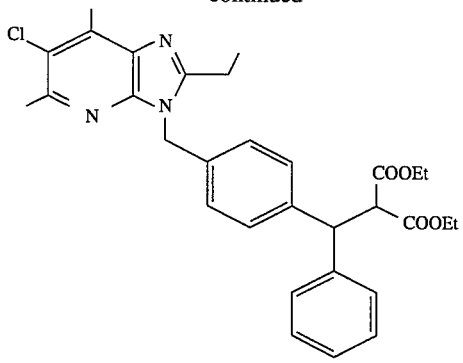

90

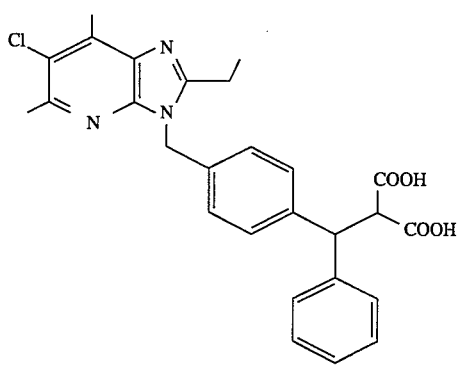

91

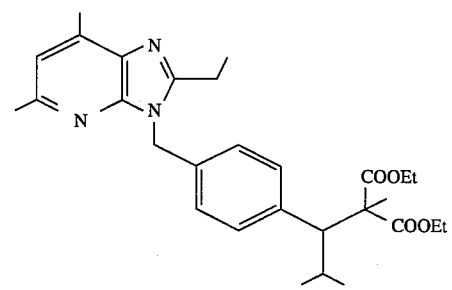

92

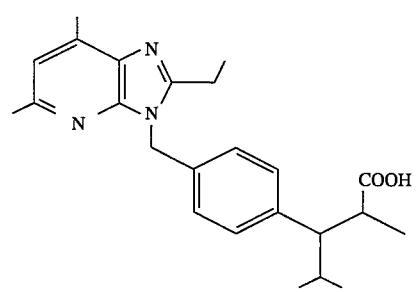

93

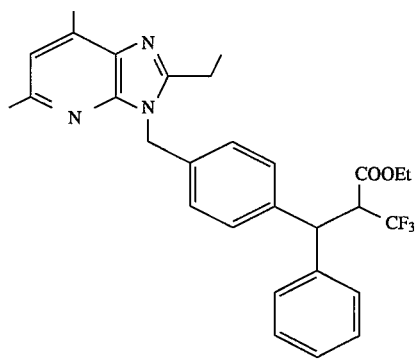

94

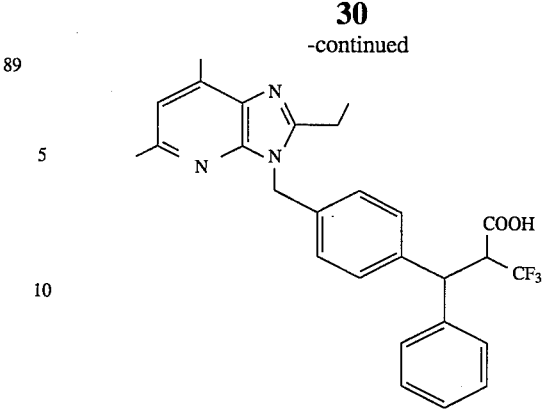

The compounds of the present invention contain one or more basic nitrogen atoms and one or more acid hydrogen atoms and, consequently, they can form salts with acids and bases both organic and inorganic, which salts are also included in the present invention. There is no limitation on the nature of these salts, provided that, when used for therapeutic purposes, they are pharmaceutically acceptable, which, as is well known in the art, means that they do not have reduced activity (or unacceptable reduced activity) or increased toxicity (or unacceptable increased toxicity) compared with the free compounds. Examples of these salts include: salts with inorganic cations such as sodium, potassium, calcium, magnesium, lithium, aluminium, zinc, etc; and salts formed with pharmaceutically acceptable amines such as ammonia, alkylamines, hydroxyalkylamines, lysine, arginine, N-methylglucamine, procaine and the like; salts with inorganic acids such as hydrochloric acid, hydrobromic acid, hydriodic acid, nitric acid, perchloric acid, sulfuric acid, or phosphoric acid; and salts with organic acids, such as methanesulfonic acid, trifluoromethanesulfonic acid, ethanesulfonic acid, benzenesulfonic acid, p-toluenesulfonic acid, fumaric acid, oxalic acid or maleic acid. The salts are prepared by treatment of the compound of formula I with a sufficient amount of the desired acid or base to produce the salt in a conventional manner. Free bases and their salts differ in certain physical properties, such as solubility, but they are equivalent for the purposes of the invention.

The compounds of the present invention can exist in unsolvated as well as solvated forms, including hydrated forms. In general, the solvated forms, with pharmaceutically acceptable solvents such as water, ethanol and the like, are equivalent to the unsolvated forms for the purposes of the invention.

Some compounds of the present invention can exist as different diastereoisomers and/or optical isomers. Diastereoisomers can be separated by conventional techniques such as chromatography or fractional crystallization. The optical isomers can be resolved using any of the conventional techniques of optical resolution to give optically pure isomers. Such a resolution can be performed in any chiral synthetic intermediate as well as in the products of general formula I. The optical resolution techniques include separation by chromatography on a chiral phase or formation of a diastereoisomeric pair, resolution and subsequent recovery of the two enantiomers. When the racemic form of a compound of formula I (or an intermediate thereof) contains an acidic group, a diastereoisomeric salt can be formed by reaction with an optically active form of a suitable organic base such as α-methylbenzylamine. The optically pure isomers can also be individually obtained using enantiospecific synthesis. The present invention covers both the individual isomers and their mixtures (e.g. racemic mixtures), whether as obtained by synthesis or by physically mixing them up. Furthermore, some of the compounds of the present invention may present cis/trans isomery. The present invention includes each of the geometric isomers as well as their mixtures.

The compounds of formula I may be prepared using the methods described below, which are illustrated in Schemes 1, 2 and 3. The precise method used for the preparation of a given compound may vary depending on its chemical structure. The reactions are performed in a solvent appropriate to the reagents and materials employed and suitable for the transformation being effected. It is understood by those skilled in the art of organic synthesis that the functionalities present on the molecule must be consistent with the chemical transformation proposed. This will frequently necessitate judgement as to the order of synthetic steps, protecting groups required and deprotection conditions. Moreover, some of the methods illustrated below for the preparation of a given class of compounds of formula I may not be readily applicable for the preparation of certain compounds falling into that class; alternative methods described must then be used.

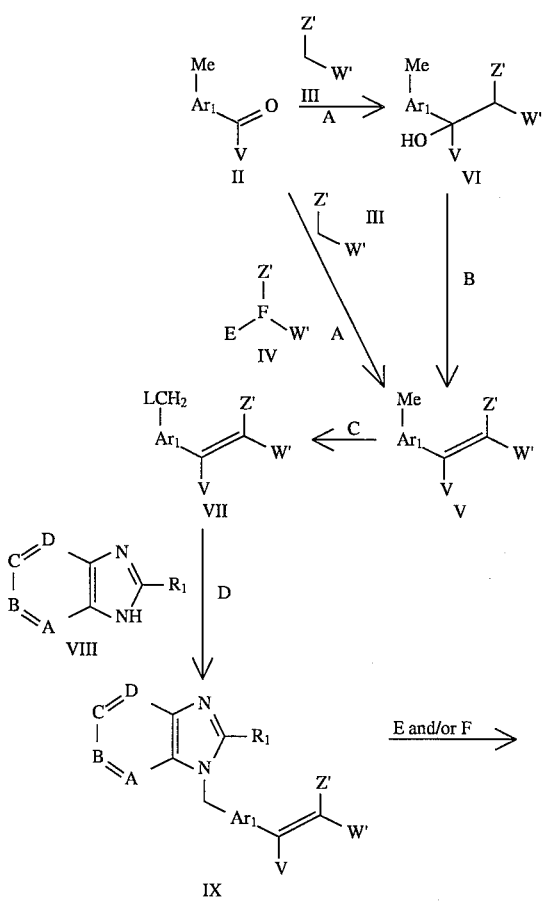

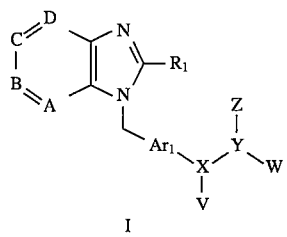

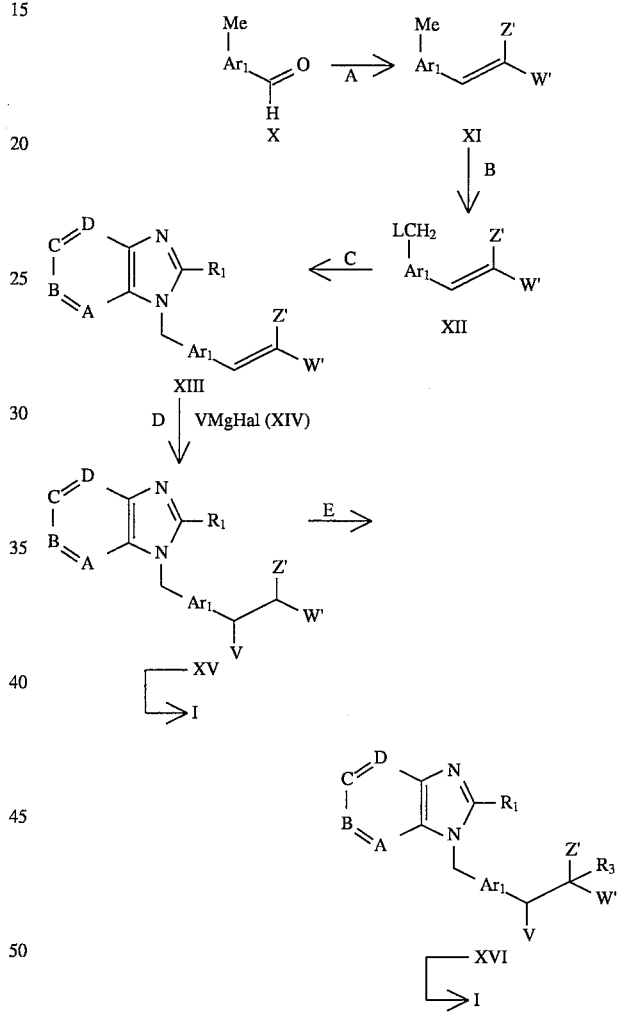

Wherein:
A, B, C, D, $Ar_1$, $R_1$, $R_3$, V, W, X, Y and Z have the previously defined meaning;

W' represents a group W or a group convertible thereto by known chemical reactions;

Z' represents a group Z or a group convertible thereto by known chemical reactions; and L represents a halogen atom, such as chlorine or bromine.

The preparation of the compounds of general formula I starts from the ketones of general formula II or the aldehydes of general formula X, which either are known compounds or, if they have not been described, can be prepared following analogous methods to those disclosed in the literature.

For example, ketones of formula II can be prepared by reaction of an aromatic nitrile or acid chloride with an aromatic magnesium compound.

According to the process disclosed in Scheme 1, ketones II (Step A) are reacted with a compound of general formula Z'—CH$_2$—W' (III, wherein Z' and W' have the previously defined meaning) to give the compounds of general formula V or VI. The reaction can be carried out in the presence of a base such as butyl lithium or lithium diisopropylamidure in a polar solvent such as tetrahydrofuran at a temperature between room temperature and that of the boiling point of the solvent and during a reaction time from 6 to 96 h. When III represents acetonitrile the reaction can be carried out in the presence of potassium hydroxide using acetonitrile itself as the solvent at the temperature of the boiling point of the solvent and during a reaction time between 6 and 96 h. When Z' and W' represent groups derived from carboxylic acid, the reaction can be carried out in the presence of ammonium acetate, piperidine or alanine and an acid such as acetic add in an apolar solvent such as benzene or toluene at the temperature of the boiling point of the solvent and during a reaction time from 6 to 96 h.

The compounds of general formula V may also be obtained by Wittig or Horner-Emmons reaction of a compound of general formula II with a compound of general formula E—F(Z')W'(IV, wherein Z' and W' have the previously defined meaning and E—F represents Ph$_3$P=C, Ph$_3$P$^+$—CH or (R$_6$O)$_2$PO—CH, wherein R$_6$ is an alkyl group) in the presence of a base such as sodium hydride in a polar solvent such as dimethoxyethane at the temperature of the boiling point of the solvent and during a reaction time from 6 to 96 h.

Furthermore, the compounds of general formula V can also be obtained by elimination of water from the compounds of general formula VI (Step B) by treatment with p-toluenesulfonic acid in a suitable solvent such as benzene or toluene in a Dean-Stark water separator, at the temperature of the boiling point of the solvent and during a reaction time enough to distil off one equivalent of water. Alternatively, dehydration can also be carried out by treatment with an acylating agent such as acetic anhydride in the presence of a base such as pyridine at room temperature and during a reaction time from 6 to 96 h, followed by reaction with a base such as 1,8-diazabicyclo[5.4.0]undec-7-ene (DBU) in an apolar solvent such as toluene at the temperature of the boiling point of the solvent and during a reaction time from 30 min to 4 h.

In Step C, a compound of formula V is allowed to react with a halogenating agent such as N-bromosuccinimide or Br$_2$ in an inert solvent such as carbon tetrachloride at the temperature of the boiling point of the solvent and during a reaction time from 3 to 48 h, to give a compound of general formula VII.

In Step D, a compound of formula VII is allowed to react with a compound of formula VIII (prepared according to the procedures described in EP 400974) in the presence of a base such as sodium hydride in a suitable solvent such as dimethylformamide at a temperature between room temperature and that of the boiling point of the solvent and during a reaction time between 3 and 48 h, to give a compound of general formula IX. When Z'=Z and W'=W, the compound of formula IX thus obtained is already a compound of formula I.

The compounds of general formula I, wherein X—Y represents CH—CH can be prepared by reduction (Step E) of a compound of formula IX or I wherein X—Y represents C=C. The reduction can be carried out by hydrogenation in the presence of a catalyst such as palladium on charcoal in a suitable solvent such as an alcohol at a temperature between room temperature and that of the boiling point of the solvent, at a pressure between 1 and 10 atm and during a reaction time from 1 to 48 h, or by reaction with a metallic hydride such as sodium borohydride in a suitable solvent such as methanol at a temperature between room temperature and that of the boiling point of the solvent and during a reaction time from 1 to 96 h.

The conversion of the groups Z' and W' into the groups Z and W can be carried out at any stage of the synthesis or in the final step (Step F). Examples of these transformations are the following: the conversion of a cyano group into a tetrazole group by treatment with one equivalent of azide such as tributyltin azide (previously prepared or formed in situ from sodium azide and tributyltin chloride) in an apolar solvent such as xylene or toluene at a temperature between room temperature and that of the boiling point of the solvent and during a reaction time between 1 and 96 h; the protection of the acid nitrogen atom of a tetrazole group with chlorotriphenylmethane in the presence of a base such as triethylamine in a polar solvent such as acetone at a temperature between room temperature and that of the boiling point of the solvent during a reaction time from 1 to 24 h; the deprotection of a triphenylmethyltetrazole group with an acid such as hydrochloric acid or formic acid in a polar solvent such as dichloromethane, tetrahydrofuran or ethanol at a temperature between room temperature and that of the boiling point of the solvent during a reaction time from 2 to 96 h; the reduction of a cyano group with a metallic hydride such as lithium aluminium hydride in a suitable solvent such as diethyl ether at a temperature between room temperature and that of the boiling point of the solvent and during a reaction time between 1 and 96 h, to give the corresponding amine and subsequent derivatization of this with an acid chloride or sulfonyl chloride.

Other reactions of intermediates include, for instance, the conversion of an intermediate compound in which X—Y represents C=C and W=H into a compound in which X—Y represents C=C and W=halogen; in case the halogen atom is bromine, the reaction can be carried out by treatment with Br$_2$ in a suitable solvent such as dichloromethane or chloroform; in case the halogen atom is chlorine, the reaction can be carried out by treatment with sulfuryl chloride in a suitable solvent such as acetic acid. Furthermore, an intermediate in which X—Y represents C=C and W=H may be converted into a compound in which X—Y represents C=C and W=CO$_2$Et by treatment with a base, such as lithium diisopropylamidure, and diethyl carbonate in a suitable solvent such as tetrahydrofuran.

A second procedure for the preparation of compounds of formula I is disclosed in Scheme 2. In a first step (step A), aldehydes of general formula X are converted into the compounds of general formula XI following an analogous procedure to that described in Scheme 1 for the preparation of compounds of formula V.

In step B, the compounds of formula XI are transformed into the compounds of formula XII following an analogous procedure to that described in step C of Scheme 1.

Next, the compounds of formula XII are reacted with a compound of formula VIII (step C) following the same procedure described above for step D of Scheme 1 to give a compound of general formula XIII.

The reaction of a compound of formula XIII (step D) with a Grignard reagent of formula VMgHal (XIV, wherein V has the previously defined meaning and Hal represents halide, preferably bromide) in the presence of a catalytic amount of CuBr in a suitable aprotic solvent such as benzene or diethyl ether at a temperature between 0° C. and that of the boiling point of the solvent, leads to the compounds of general formula XV. When Z'=Z and W'=W, the compound of formula XV thus obtained is already a compound of formula I. Otherwise, it can be converted into a compound of formula I by transformation of the groups Z' and/or W' into Z and/or W following the procedures described above.

Finally, the alkylation (step E) of a compound of formula XV or I, wherein X—Y represents CH—CH, leads to the compounds of general formula XVI, wherein X—Y represents CH—CR$_3$ and R$_3$ represents C$_{1-4}$ alkyl or aryl(C$_{1-4}$)alkyl. This transformation is carried out by treatment with an equivalent of base such as sodium hydride and an alkylating agent of formula R$_3$—T (wherein T represents a good leaving group such as chlorine, bromine or iodine and R$_3$ represents C$_{1-4}$ alkyl or aryl-(C$_{1-4}$)alkyl) in an inert solvent such as dimethylformamide at a temperature between 0° C. and that of the boiling point of the solvent during a period of time between 6 and 48 h. Again, when Z'=Z and W'=W, the compound of formula XVI thus obtained is already a compound of formula I. Otherwise, it can be converted into a compound of formula I by transformation of the groups Z' and/or W' into Z and/or W following the procedures described above.

As it will be appreciated by those skilled in the art, it is possible to change the order of synthetic steps in the sequence illustrated in Scheme 2. Thus, for instance, compounds of formula XV or XVI may be prepared from compounds of formula XI using the following sequence: reaction of XI with a Grignard reagent of formula XIV following the procedure described above for step D; alkylation of the resulting compound as described in step E (this step is obviously not needed when the desired product is of formula XV); halogenation of the resulting compound as described in step B; and reaction of the resulting compound with a compound of formula VIII as described in step C.

A third procedure for the preparation of compounds of formula I wherein W represents hydrogen, C$_{1-4}$ alkyl or aryl-(C$_{1-4}$)alkyl is shown in Scheme 3:

Scheme 3

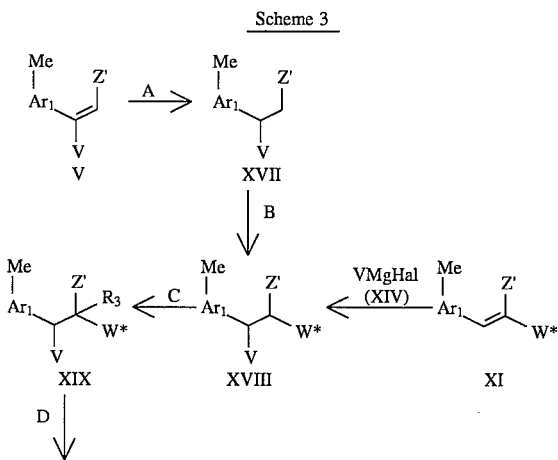

Scheme 3 -continued

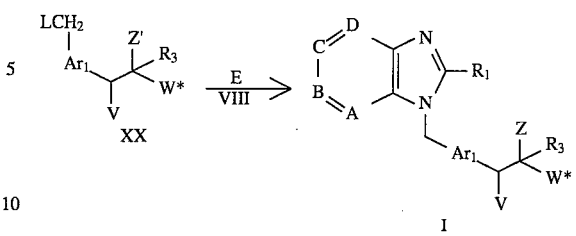

Wherein:

A, B, C, D, Ar$_1$, R$_1$, R$_3$, V, Z, Z' and L have the previously defined meaning; and W* represents hydrogen, C$_{1-4}$ alkyl or aryl-(C$_{1-4}$)alkyl.

In a first step (step A), a compound of formula V (wherein W'=H) is converted into a compound of formula XVII by hydrogenation in the same experimental conditions mentioned above for step E of Scheme 1.

In step B, a compound of formula XVII is allowed to react with an equivalent of base, such as lithium diisopropylamidure, and an alkylating agent of formula W*—T (wherein T represents a good leaving group such as chlorine, bromine or iodine and W* represents C$_{1-4}$ alkyl or aryl-(C$_{1-4}$)alkyl) in an inert solvent such as tetrahydrofuran at a temperature between room temperature and that of the boiling point of the solvent during a period of time from 6 h to 48 h, to give a compound of formula XVIII. When in a compound of formula I W*=H, this alkylation step is obviously not needed and then the compound of formula XVII is already a compound of formula XVIII. Compounds of formula XVIII can also be obtained by reaction of a compound of formula XI (wherein W'=W*, i.e. hydrogen, C$_{1-4}$ alkyl or aryl-(C$_{1-4}$)alkyl) with a Grignard reagent of formula XIV following the conditions previously described for step D of Scheme 2.

The subsequent alkylation of this compound XVIII (step C) with another equivalent of base and an alkylating agent of formula R$_3$—T (wherein T represents a good leaving group such as chlorine, bromine or iodine and R$_3$ represents C$_{1-4}$ alkyl or aryl-(C$_{1-4}$)alkyl) leads to the compounds of general formula XIX. When in the compound of formula I R$_3$=H, this second alkylation step is obviously not needed.

In step D, a compound of formula XIX is transformed into a compound of formula XX following the same procedure described above in step C of Scheme 1. When in the compound of formula I W*50 H and R$_3$=H, step D is carried out directly over compound XVII.

This compound XX is then converted into a compound of formula I (step E) by reaction with a compound of formula VIII following the same procedure described above in step D of Scheme 1 followed, if necessary, by conversion of a group Z' into a group Z using the processes described above.

Furthermore, a compound of formula I may also be prepared by interconversion from another compound of formula I in one or a plurality of steps.

Thus, for instance, a compound of formula I, wherein X—Y represents CH—CH, Z represents COOH and W represents C$_{1-4}$ alkyl or aryl(C$_{1-4}$)alkyl, may be prepared from a compound of formula I, wherein X—Y represents CH—CR$_3$, R$_3$ represents C$_{1-4}$ alkyl or aryl-(C$_{1-4}$)alkyl, and Z and W represent CO$_2$R$_4$, by decarboxylation in the presence of a base such as potassium hydroxide in a polar solvent such as ethanol or ethanol-water mixtures at the temperature of the boiling point of the solvent and during a period of time between 4 h and 5 days.

A compound of formula I may also be converted into another compound of formula I by transformation of the groups Z and/or W into other groups Z and/or W using standard methods of organic synthesis. Examples of these transformations include: the hydrolysis of an ester group to give a carboxy group, in the presence of a base such as potassium hydroxide either in a polar solvent such as ethanol or ethanol-water mixtures or in an apolar solvent such as benzene in the presence of a crown ether such as 18-C-6, at a temperature between room temperature and that of the boiling point of the solvent and during a reaction time between 2 and 24 h; the conversion of a carboxy group into a group —$CONHSO_2R_4$ by reaction with 1,1'-carbonyldi-imidazole in a suitable solvent such as tetrahydrofuran at elevated temperatures, followed by reaction of the intermediate acylimidazole thus obtained with a sulfonamide of formula $NH_2SO_2R_4$ and a base such as DBU; the conversion of a carboxy group into a group —$CONR_4R_5$ by reaction with 1-hydroxybenzotriazole and dicyclohexylcarbodiimide to form in situ an activated ester and subsequent reaction of said ester with an amine of formula $NHR_4R_5$ in an inert solvent such as dimethylformamide at a temperature between 0° C. and 60° C.; the reduction of an ester or cyano group with a metallic hydride such as lithium aluminium hydride in a suitable solvent such as methanol at a temperature between room temperature and that of the boiling point of the solvent and during a reaction time between 1 and 96 h, to give the corresponding alcohol and amine, and subsequent derivatization of the resulting amine with an acid chloride or sulfonyl chloride; the oxidation of a $C_{1-4}$ alkylthio group to a $C_{1-4}$ alkylsulfinyl group by treatment with metachloroperbenzoic acid in a suitable solvent such as dichloromethane; the conversion of a hydrogen atom (i.e. W=H) in a compound of formula I wherein X—Y represents CH—CH into a bromine atom (i.e. W=Br) by treatment with a brominating agent such as $PBr_3$ at elevated temperatures; the conversion of a hydrogen atom (i.e. W=H) in a compound of formula I wherein X—Y represents C=C into a chlorine atom (i.e. W=Cl) by reaction with sulfuryl chloride in a suitable solvent such as acetic acid at a temperature between room temperature and that of the boiling point of the solvent, preferably 60°–85° C.

It will be appreciated by those skilled in the art that apart from the interconversion of one compound of formula I into another, these reactions may also be used in the preparation of suitable intermediates.

The salts of the compounds of formula I may be prepared following standard procedures by treatment for example with hydrochloric acid, sulphuric acid, nitric acid, oxalic acid, or methanesulfonic acid, or with sodium hydroxide, potassium hydroxide, etc.

Compounds of formulae III, IV, XIV, $R_3 13$ T and W*—T are either commercially available or widely described in the literature or can be prepared by methods similar to those described, starting from commercially available products.

Angiotensin II is a potent arterial vasoconstrictor, and it exerts its action by interacting with specific receptors. The compounds disclosed in the present invention act as competitive antagonists of the angiotensin II receptors. In order to determine their efficacy both in vitro and in vivo, the compounds of the present invention were tested in the following pharmacological tests:

Test 1: Angiotensin II receptor binding assay

The membrane fraction used in this assay was prepared from rat adrenal glands. The tissues were collected in 50 mM Tris-HCl buffer, pH 7.5, so that the concentration was 20% (w/v) and were homogenized at 1000×rpm. The homogenate was centrifuged at 1000 g for 10 min and the supernatant further centrifuged at 100,000 g for 1 h. The resulting membrane pellet was then resuspended in the above buffer at a concentration of 10 mg of protein/mL. 100 μL aliquots of the membrane suspension were stored frozen at −70° C. until used.

Aliquots containing 15 μg of protein were incubated at 25° C. for 1 h in incubation buffer containing (final concentrations): NaCl (120 mM), $Mg_2$ (5 mM), 0.05% bovine serum albumin, and Tris (50 mM), adjusted to pH 7.5, with or without dithiothreitol (1 mM) to characterize whether drugs preferentially interact with $AT_1$ or $AT_2$ receptor subtypes. Incubation was initiated by the addition of 10 nM 3H-Angiotensin II. Total incubation volume was 250 μL. Nonspecific binding was measured by incubation in the presence of 0.1 μM $Sar^1,Ile^8$-Angiotensin II. Test compounds were studied in the range of concentrations $10^{-10}M–10^5M$. Binding was terminated by rapid filtration using a Millipore Multiscreen device. Filters were washed three times with 250 μL of the corresponding buffer containing or not 1 mM dithiothreitol. Dry filters were placed into vials containing 3 mL of scintillation fluid and the radioactivity counted in a scintillation counter. The $IC_{50}$ value (concentration for 50% displacement of the specifically bound 3H-angiotensin II) was determined for each test compound. The compounds of the present invention were found to have $IC_{50}$ values at or less than 50 μL.

Test 2—Inhibition of Angiotensin II induced pressor response in anesthetized normotensive rats Male Sprague-Dawley rats (b.w. 250–300 g) were anesthetized with sodium pentobarbital (60 mg/Kg i.p.) and a catheter was implanted into the carotid artery. The catheter was connected to a pressure transducer coupled to a polygraph for monitoring arterial blood pressure. Angiotensin II was administered intravenously through the left femoral artery every 10 min. After two angiotensin II induced responses, test compounds were infused (2 min) through the right femoral artery. One minute later, angiotensin II was administered again. Percent inhibition due to treatment was calculated by comparing the increase in arterial pressure during the third administration of angiotensin II with the mean of the increase in arterial pressure obtained in the first two administrations of angiotensin II.

Test 3—Inhibition of Angiotensin II-induced pressor response in pithed rats

Male Sprague-Dawley rats (b.w. 250 g) were anesthetized with sodium pentobarbital (50 mg/Kg, i.p.). The trachea was cannulated and the rats were pithed through the orbit with a stainless steel pithing rod. The rats were immediately placed on a rodent ventilator (volume −1 mL/100 g b.w.; rate −74 strokes/min). The carotid artery was cannulated and connected to a pressure transducer for arterial pressure measurement. A dose-pressor response curve for angiotensin II was obtained administering intravenously and in a cumulative manner doses of AII (0.01–300 μg/Kg). Then, animals were treated with a dose of the test compound or vehicle 15 minutes before injection of AII. The effective dose of AII required to induce an increase in arterial pressure of 60 mm Hg was calculated for each test compound.

Test 4—Effects on blood pressure in conscious renal hypertensive rats

Male Sprague-Dawley rats were anesthetized with sodium pentobarbital (60 mg/Kg, i.p.) and the left renal artery was completely ligated. After 5 days the animals were dosed orally with the test compound and blood pressure was measured at the animal's tail using a sphigmomanometer. Effects on mean arterial pressure due to treatment were compared to those observed in the control group (animals which had been operated on but whose renal artery had not been ligated).

Using the methodology described above, representative compounds of the present invention were evaluated in vivo and found to be active at a dose of 50 mg/Kg or much less.

Thus, the compounds of the present invention are useful in the treatment of cardiovascular pathologies where the renin-angiotensin system is involved, such as primary or secondary hypertension, renal vascular hypertension, acute and chronic congestive heart failure, left ventricular hypertrophy, vascular hypertrophy, and diseases related with an elevated intraocular pressure such as glaucoma. Likewise, they can also be of value in the management of other pathologies partly related to the above such as primary and secondary hyperaldosteronism, in the treatment of other disorders of renal ethiology such as diabetic nephropathy, glomerulonephritis, scleroderma, glomerular sclerosis, renal failure, renal transplant therapy, diabetic retinopathy, and in the management of other vascular disorders such as migraine.

The application of the compounds of this invention for these and similar disorders will be apparent to those skilled in the art.

Furthermore, angiotensin II antagonists may also be useful for the treatment of cognitive disorders such as dementia, Alzheimer's disease, amnesia, and learning disorders.

According to the activity of the compounds disclosed, the present invention further provides compositions that comprise a compound of the invention together with an excipient and optionally other auxiliary agents, if necessary. The compounds of the present invention can be administered in different pharmaceutical preparations, the precise nature of which will depend, as it is well known, upon the chosen route of administration and the nature of the pathology to be treated.

Thus, solid compositions according to the present invention for oral administration include compressed tablets, dispersible powders, granules and capsules. In tablets, the active component is admixed with at least one inert diluent such as lactose, starch, mannitol, microcrystalline cellulose or calcium phosphate; granulating and disintegrating agents for example corn starch, gelatine, microcrystalline cellulose or polyvinylpyrrolidone; and lubricating agents for example magnesium stearate, stearic acid or talc. The tablets may be coated by known techniques to delay disintegration and absorption in the gastrointestinal tract and, thereby, provide a sustained action over a longer period. Gastric film-coated or enteric film-coated tablets can be made with sugar, gelatin, hydroxypropylcellulose, or acrylic resins. Tablets with a sustained action may also be obtained using an excipient which provides regressive osmosis, such as the galacturonic acid polymers. Formulations for oral use may also be presented as hard capsules of absorbable material, such as gelatin, wherein the active ingredient is mixed with an inert solid diluent and lubricating agents, or pasty materials, such as ethoxylated saturated glycerides. Soft gelatin capsules are also possible, wherein the active ingredient is mixed with water or an oily medium, for example peanut oil, liquid paraffin or olive oil.

Dispersible powders and granules suitable for the preparation of a suspension by the addition of water provide the active ingredient in admixture with dispersing or wetting agents, suspending agents, such as sodium carboxymethylcellulose, methylcellulose, hydroxypropylmethylcellulose, sodium alginate, polyvinylpyrrolidone, gum tragacanth, xantham gum, gum acacia, and one or more preservatives, such as methyl or n-propyl-p-hydroxybenzoate. Additional excipients, for example sweetening, flavoring and coloring agents may also be present.

Liquid compositions for oral administration include emulsions, solutions, suspensions, syrups and elixirs containing commonly used inert diluents, such as distilled water, ethanol, sorbitol, glycerol, or propylene glycol. Such compositions may also comprise adjuvants such as wetting agents, suspending agents, sweetening, flavoring, perfuming, preserving agents and buffers.

Other compositions for oral administration include spray compositions, which may be prepared by known methods. The spray compositions will contain a suitable propellent.

Preparations for injection, according to the present invention, for parenteral administration by bolus injection or continuous infusion include sterile aqueous or non-aqueous solutions, suspensions or emulsions, in a nontoxic parentally-acceptable diluent or solvent. Examples of aqueous solvents or suspending media are distilled water for injection, Ringer's solution, and isotonic sodium chloride solution. Examples of non-aqueous solvents or suspending media are propylene glycol, polyethylene glycol, vegetable oils such as olive oil, or alcohols such as ethanol. These compositions may also include adjuvants such as wetting, preserving, emulsifying and dispersing agents. They may be sterilized by any known method or manufactured in the form of sterile solid compositions which can be dissolved in sterile water or some other sterile injectable medium immediately before use. When all of the components are sterile, the injectables will maintain the sterility if they are manufactured in sterile environment.

A compound of the invention may also administered in the form of suppositories for rectal administration of the drug. Such compositions are prepared following conventional procedures, well known to those skilled in the art. For example, they can be prepared by mixing the active ingredient with a conventional suppository base such as cocoa butter or other glycerides.

The compounds of the present invention can also be administered in combination with other antihypertensives and/or diuretics and/or ACE inhibitors and/or calcium channel blockers and/or potassium channel openers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartrate, methylclothiazide, methyldopa, methyldopa hydrochloride, minoxidil, pargyline hydrochloride, polythiazide, prazosin, propanolol, rauwolfia serpentina, rescinnamine, reserpine, sodium nitroprusside, spironolactone, timolol maleate, trichlormethiazide, trimethopan camsylate, benzothiazide, quinethazone, ticrynafan, triamterene, acetazolamide, aminophylline, cyclothiazide, ethacrynic acid, furosemide, procaine, sodium ethacrynate, captopril, delapril hydrochloride, enalapril, enalaprilat, fosinopril sodium, lisinopril, pentopril, quinapril hydrochloride, ramipril, perindopril, teprotide, zofenopril calcium, diflunisal, diltiazem, felodipine, nicardipine, nifedipine, niludipine, nimodipine, nisoldipine, nitrendipine, amlodipine, isradipine, ketanserine, fenoldopam, ibodopamine, verapamil, nicorandil, pinacidil and the like, as well as mixtures and combinations thereof.

When the compounds of this invention are used for the treatment of elevated intraocular pressure, they can be administered in the form of typical pharmaceutical preparations such as the above mentioned or they can be administered in the form of topical ocular formulations, which include solutions, oinments, gels and the like.

The dosage and frequency of dose may vary depending upon symptoms, age and body weight of the patient, as well as upon the route of administration. In general, the compounds of the present invention may be administered for example orally to human patients in a daily dose from 0.1 to 500 mg for an adult, preferably a dosage from 2 to 150 mg, which may be administered either as a single dose or as divided doses. However, in particular cases, at the discretion of the attending physician, doses outside the broader range may be required.

The pharmaceutical formulations for topical administration will typically contain about 0.1% to 15% by weight of a compound of formula I. This ocular preparations should contain oftalmologically-acceptable excipients.

Following are some representative preparations for tablets, capsules, syrups and injectables. They can be prepared following standard procedures and they are useful in the treatment of diseases related with the regulation of the renin-angiotensin system such as hypertension, congestive heart failure and elevated intraocular pressure.

| Tablets | |
|---|---|
| Compound of formula I | 100 mg |
| Dibasic calcium phosphate | 125 mg |
| Sodium starch glycolate | 10 mg |
| Talc | 12.5 mg |
| Magnesium stearate | 2.5 mg |
| | 250.0 mg |
| Hard gelatin capsules | |
| Compound of formula I | 100 mg |
| Lactose | 197 mg |
| Magnesium stearate | 3 mg |
| | 300 mg |
| Syrup | |
| Compound of formula I | 0.4 g |
| Sucrose | 45 g |
| Flavouring agent | 0.2 g |
| Sweetening agent | 0.1 9 |
| Water to | 100 ml |
| Injectable | |
| Compound of formula I | 100 mg |
| Benzylic alcohol | 0.05 ml |
| Propylene glycol | 1 ml |
| Water to | 5 ml |

The following examples illustrate, but do not limit, the scope of the present invention:

REFERENCE EXAMPLE 1

Ethyl 3-(4-methylphenyl)-3-phenyl-2-propenoate

To a solution of 3.33 g (0.075 mol) of 55% sodium hydride in 112.5 mL of dimethoxyethane, cooled with an ice bath, was slowly added under argon 15.15 mL (0.075 mol) of triethyl phosphonoacetate. After the addition was complete, the resulting mixture was stirred at room temperature for 30 min. Then, 15 g (0.075 mol) of 4-methylbenzophenone was added and the mixture was stirred at reflux for 4 days. Water was added and the resulting solution was extracted with diethyl ether. The organic phase was dried and the solvent was removed, to yield a crude product that was purified by chromatography on silica gel (hexane-$CH_2Cl_2$) to provide 21.4 g of the title compound of the example as a mixture of cis/trans isomers (yield: quantitative).

$^1$H-NMR (80 MHz, $CDCl_3$) δ (TMS): 1.08 (t, J=7 Hz, 0.5×3H, $CH_3$), 1.13 (t, J=7 Hz, 0.5×3H, $CH_3$), 2.32 (s, 0.5×3H, $CH_3$), 2.37 (s, 0.5×3H, $CH_3$), 4.03 (q, J=7 Hz, 0.5×2H, $CH_2$), 4.05 (q, J=7 Hz, 0.5×2H, $CH_2$), 6.31 (s, 0.5×1H, CH=), 6.34 (s, 0.5×1H, CH=), 7.24 (m, 9H, Ar).

REFERENCE EXAMPLE 2

Ethyl [3-(4-bromomethylphenyl)]-3-phenyl-2-propenoate

To a solution of 10 g (37.6 mmol) of the product obtained in reference example 1 in 214 mL of carbon tetrachloride was added 6.8 g (38.3 mmol) of N-bromosuccinimide (NBS) and 0.64 g (2.6 mmol) of benzoyl peroxide and the resulting mixture was stirred at reflux for 5 h. The resulting solution was allowed to cool, and the imide formed was filtered and washed with carbon tetrachloride. The filtrates was evaporated to afford 13 g of the title compound of the example (yield: quantitative).

$^1$H-NMR (80 MHz, $CDCl_3$) δ (TMS): 1.10 (t, J=7 Hz, 0.5×3H, $CH_3$), 1.12 (t, J=7 Hz, 0.5×3H, $CH_3$), 4.05 (q, J=7 Hz, 0.5×2H, $CH_2$), 4.05 (q, J=7 Hz, 0.5×2H, $CH_2$), 4.47 (s, 0.5×2H, $CH_2$), 4.52 (s, 0.5×2H, $CH_2$), 6.37 (s, 1H, CH=), 7.24 (m, 9H, Ar).

REFERENCE EXAMPLE 3

5,7-Dimethyl-3-[[4-(2-ethoxycarbonyl-1-phenylvinyl) phenyl]methyl]-2-ethyl-3H-imidazo[4,5-b]pyridine To a suspension of 2.2 g (46.4 mmol) of 50% sodium hydride in 90 mL of anhydrous dimethylformamide, cooled with an ice bath and under argon, was added dropwise 5.4 g (31 mmol) of 5,7-dimethyl-2-ethylimidazo[4,5-b]pyridine (obtained according to the procedure described in EP 400974) and finally 13 g (38 mmol) of the compound obtained in reference example 2. After the addition was complete, the reaction mixture was stirred at room temperature overnight. Water was added and the solvent was removed. The residue was taken up in ethyl acetate and washed with brine. The organic phase was dried and the solvent was removed to yield 17 g of a crude product. This was chromatographed on silica gel (hexane-ethyl acetate mixtures of increasing polarity) to afford 9.4 g of the title compound of the example (yield: 69%).

¹H-NMR (80 MHz, CDCl₃) δ (TMS): 1.08 (t, J=7 Hz, 3H, CH₃), 1.32 (t, J=7 Hz, 0.5×3H, CH₃), 1.33 (t, J=7 Hz, 0.5×3H, CH₃), 2.57 (s, 0.5×3H, CH₃), 2.59 (s, 0.5×3H, CH₃), 2.62 (s, 3H, CH₃), 2.79 (q, J=7 Hz, 2H, CH₂), 4.03 (q, J=7 Hz, 2H, CH₂), 4.43 (s, 0.5×2H, CH₂), 4.49 (s, 0.5×2H, CH₂), 6.31 (s, 1H, CH=), 6.88 (s, 1H, Pyr), 7.24 (m, 9H, Ar).

REFERENCE EXAMPLE 4

3-(4-Methylphenyl)-3-phenyl-2-propenonitrile

To a solution of 6.5 g (0.114 mol) of KOH in 70 mL of acetonitrile was added dropwise under argon a solution of 4-methylbenzophenone (22.5 g, 0.114 mol) in acetonitrile (45 mL). After the addition was complete, the reaction mixture was heated at reflux overnight. It was then allowed to cool, poured into ice and extracted with dichloromethane. The organic phase was dried and the solvent was removed to afford 30 g of a crude product that was chromatographed on silica gel (hexane-ethyl acetate mixtures of increasing polarity) to give 19.5 g of the desired product (yield: 78%).

¹H-NMR (80 MHz, CDCl₃) δ (TMS): 2.35 (s, 3H, CH₃), 5.64 (s, 1H, CH=), 7.29 (m, 9H, Ar).

REFERENCE EXAMPLE 5

5-[2-(4-Methylphenyl)-2-phenylvinyl]tetrazole

To a solution of 19.3 g (88 mmol) of the compound obtained in reference example 4 in 195 mL of toluene was added under argon 26 mL (96.15 mmol) of tributyltin chloride and 5.8 g (88 mmol) of sodium azide. After heating at reflux for 4 days, it was allowed to cool to room temperature and extracted with 1N NaOH. Water was added, and the resulting solution was washed with ether and acidified with 6N HCl. Then, it was extracted with ether, whereupon a white solid precipitated, which was filtered off and dried. The organic phase was dried and the solvent was removed, yielding more solid. In all, 13 g of the title compound of the example was obtained as a white solid (yield: 52%).

¹H-NMR (80 MHz, CDCl₃) δ (TMS): 2.38 (s, 0.5×3H, CH₃), 2.40 (s, 0.5×3H, CH₃), 6.92 (s, 1H, CH=), 7.20 (m, 10H, Ar+NH).

REFERENCE EXAMPLE 6

5-[2-(4-Methylphenyl)-2-phenylvinyl]-N-triphenylmethyltetrazole

To a suspension of 13 g (49.5 mmol) of the compound obtained in reference example 5 in 130 mL of acetone was added 5.3 mL (52.2 mmol) of triethylamine. Next, 13.4 g (52.2 mmol) of triphenylchloromethane was added and the mixture was stirred at room temperature for 48 h. Upon removal of the solvent, the residue was partitioned between water and dichloromethane, and the aqueous phase was reextracted with dichloromethane. The combined organic phases were dried and the solvent was removed to give a crude product. This was purified by crystallization from diethyl ether to afford 17.8 g of the title compound of the example as a white solid (yield: 71%).

¹H-NMR (80 MHz, CDCl₃) δ (TMS): 2.31 (s, 0.5×3H, CH₃), 2.34 (s, 0.5×3H, CH₃), 6.80–7.40 (m, 25H, Ar).

REFERENCE EXAMPLE 7

5-[2-(4-Bromomethylphenyl)-2-phenylvinyl]-N-triphenylmethyltetrazole

Following the procedure described in reference example 2, but starting from the compound obtained in reference example 6, the title compound of this example was obtained as a yellow solid (yield: quantitative).

¹H-NMR (80 MHz, CDCl₃) δ (TMS): 4.39 (s, 0.5×2H, CH₂), 4.45 (s, 0.5×2H, CH₂), 6.80–7.40 (m, 25H, Ar).

REFERENCE EXAMPLE 8

5,7-Dimethyl-3-[[4-[1-phenyl-2 -(N-triphenylmethyltetrazol-5-yl)vinyl]phenyl]methyl]-2-ethyl-3H-imidazo[4,5-b]pyridine Following the procedure described in reference example 3, but using the compound obtained in reference example 7 instead of the compound obtained in reference example 2, the title compound of the example was obtained as a mixture of the cis/trans isomers, which were separated by chromatography on silica gel (ethyl acetate-hexane) to give a less polar isomer (A, yield: 25%) and a more polar isomer (B, yield: 21%).

Isomer A: ¹H-NMR (80 MHz, CDCl₃) δ (TMS): 1.23 (t, J=7.5 Hz, 3H, CH₃), 2.59 (s, 3H, CH₃), 2.64 (s, 3H, CH₃), 2.70 (q, J=7.5 Hz, 2H, CH₂), 5.38 (s, 2H, CH₂), 6.8–7.4 (m, 26H, Ar).

Isomer B: ¹H-NMR (80 MHz, CDCl₃) δ (TMS): 1.30 (t, J=7.5 Hz, 3H, CH₃), 2.57 (s, 3H, CH₃), 2.62 (s, 3H, CH₃), 2.78 (q, J=7.5 Hz, 2H, CH₂), 5.44 (s, 2H, CH₂), 6.8–7.4 (m, 26H, Ar).

REFERENCE EXAMPLE 9

(4-Methylphenyl)phenylmethylidenemalononitrile

To a solution of 0.85 mL (6 mmol) of diisopropylamine in 11.3 mL of dry tetrahydrofuran, cooled to −78° C., was added 3.5 mL (5.6 mmol) of BuLi and the resulting mixture was stirred for 10 min. Next, 0.34 g (5.1 mmol) of malononitrile dissolved in 1.7 mL of tetrahydrofuran was carefully added and the resulting mixture was stirred for 30 min more. Finally, 1 g (5.1 mmol) of 4-methylbenzophenone in 1.7 mL of tetrahydrofuran was added. The mixture was allowed to warm up to room temperature and then it was heated at reflux for 2 days. Ethyl acetate was added and the resulting solution was washed with water. The aqueous phase was extracted with ethyl acetate and the combined organic phases were dried and the solvent was removed to yield 1.3 g of the desired product as a reddish oil (yield: quantitative).

¹H-NMR (80 MHz, CDCl₃) δ (TMS): 2.43 (s, 3H, CH₃), 7.2–7.9 (m, 9H, Ar).

REFERENCE EXAMPLE 10

5-[1-Cyano-2-(4-methylphenyl)-2-phenylvinyl]tetrazole

Following a similar procedure to that described in reference example 5, but starting from the compound obtained in reference example 9, the title compound of this example was obtained as a mixture of the cis and trans isomers (yield: 66%).

¹H-NMR (80 MHz, CDCl₃) δ (TMS): 2.98 (s, 3H, CH₃), 7.5–8.1 (m, 10H, Ar+NH).

REFERENCE EXAMPLE 11

5-[1-Cyano-2-(4-methylphenyl)-2-phenylvinyl]-N-triphenylmethyltetrazole

Following the procedure described in reference example 6, but starting from the compound obtained in reference example 10, a crude product was obtained which was chromatographed on silica gel (hexane-ethyl acetate, 20%), to give the title compound of this example as a mixture of the cis and trans isomers (yield: 59%).

$^1$H-NMR (80 MHz, CDCl$_3$) δ (TMS): 2.27 (s, 0.5×3H, CH$_3$), 2.39 (s, 0.5×3H, CH$_3$), 6.8–7.5 (m, 24H, Ar).

REFERENCE EXAMPLE 12

5-[2-(4-Bromomethylphenyl) -1-cyano-2-phenylvinyl]-N-triphenylmethyl tetrazole

Following a similar procedure to that described in reference example 2, but starting from the compound obtained in reference example 11, the title compound of this example was obtained as a mixture of the cis and trans isomers (yield: quantitative).

$^1$H-NMR (80 MHz, CDCl$_3$) δ (TMS): 4.34 (s, 0.5×2H, CH$_2$), 4.49 (s, 0.5×2H, CH$_2$), 6.7–7.7 (m, 24H, Ar).

REFERENCE EXAMPLE 13

3-[[4-[2-Cyano-1-phenyl-2-(N-triphenylmethyltetrazole-5-yl)vinyl]phenyl]methyl]-5,7-dimethyl-2-ethyl-3H-imidazo[4,5-b]pyridine Following the procedure described in reference example 3, but starting from the compound obtained in reference example 12, the title compound of the example was obtained as a mixture of the cis and trans isomers (yield: 35%).

$^1$H-NMR (80 MHz, CDCl$_3$) δ (TMS): 1.21 (t, J=7.5 Hz, 3H, CH$_3$), 2.55 (s, 3H, CH$_3$), 2.62 (s, 3H, CH$_3$), 2.70 (q, J=7.5 Hz, 2H, CH$_2$), 5.35 (s, 0.5×2H, CH$_2$), 5.49 (s, 0.5×2H, CH$_2$), 6.7–7.6 (m, 25H, Ar).

REFERENCE EXAMPLE 14

2-(4-Methylbenzoyl)pyridine

In a 250 mL flask were placed 1.425 g (58.5 mmol) of magnesium turnings, 35 mL of anhydrous ether and a iodine crystal. Next, 10 g (58.8 mmol) of 4-bromotoluene dissolved in 70 mL of ether was added dropwise. After the addition was complete, the resulting mixture was heated at reflux for 30 min. Then a solution of 6 g (58.5 mmol) of 2-cyanopyridine in 35 mL of anhydrous tetrahydrofuran was added dropwise and the reaction mixture was stirred at room temperature overnight. The resulting mixture was poured into 1N HCl and extracted several times with ethyl acetate. The organic phase was dried and the solvent was removed, to afford a crude product that was chromatographed on silica gel (hexane-ethyl acetate mixtures of increasing polarity) to give 7.2 g of the desired product (yield: 62%).

$^1$H-NMR (80 MHz, CDCl$_3$) δ (TMS): 2.39 (s, 3H, CH$_3$), 7.1–7.5 (m, 3H, Ar), 7.7–8.1 (m, 4H, Ar), 8.68 (d, J=4 Hz, 1H, Pyr).

REFERENCE EXAMPLE 15

3-(4-Methylphenyl)-3-(2-pyridyl)propenonitrile

Following the procedure described in reference example 4, but using the compound obtained in reference example 14 instead of 4-methylbenzophenone, the title compound of this example was obtained as a mixture of isomers (yield: 15%).

$^1$H-NMR (80 MHz, CDCl$_3$) δ (TMS): 2.42 (s, 3H, CH$_3$), 6.62 (s, 1H, CH=), 7.0–8.0 (m, 7H, Ar), 8.67 (d, J=3.2 Hz, 1H, Pyr).

REFERENCE EXAMPLE 16

5-[2-(4-Methylphenyl)-2-(2-pyridyl)vinyl]tetrazole

Following a similar procedure to that described in reference example 5, but starting from the compound obtained in reference example 15, the title compound of this example was obtained (yield: 70%).

$^1$H-NMR (80 MHz, CDCl$_3$) δ (TMS): 2.48 (s, 3H, CH$_3$), 7.0–7.7 (m, 8H, Ar+NH), 8.05 (s, 1H, CH=), 8.68 (d, J=4 Hz, 1H, Pyr).

REFERENCE EXAMPLE 17

5-[2-(4-Methylphenyl)-2-(2-pyridyl)vinyl]-N-triphenylmethyltetrazole

Following a similar procedure to that described in reference example 6, but starting from the compound obtained in reference example 16, the title compound of the example was obtained (yield: 90%).

$^1$H-NMR (80 MHz, CDCl$_3$) δ (TMS): 2.32 (s, 3H, CH$_3$), 6.7–7.6 (m, 23H, Ar+CH=) 8.64 (d, J=4 Hz, 1 H, Pyr).

REFERENCE EXAMPLE 18

5-[2-(4-Bromomethylphenyl)-2-(2-pyridyl)vinyl]-N-triphenylmethyltetrazole

Following a similar procedure to that described in reference example 2, but starting from the compound obtained in reference example 17, the title compound of this example was obtained (yield: 93%).

$^1$H-NMR (80 MHz, CDCl$_3$) δ (TMS): 4.42 (s, 2H, CH$_2$), 6.7–7.6 (m, 22H, Ar), 8.00 (s, 1H, CH=), 8.66 (d, J=4 Hz, 1H, Pyr).

REFERENCE EXAMPLE 19

5,7- Dimethyl-2-ethyl-3-[[4-[1-(2-pyridyl) -2-(N-triphenylmethyl tetrazol-5-yl)vinyl]phenyl]methyl]-3 H-imidazo[4,5-b]pyridine Following the procedure described in reference example 3, but starting from the compound obtained in reference example 18, the title compound of the example was obtained (yield: 32%).

$^1$H-NMR (80 MHz, CDCl$_3$) δ (TMS): 1.24 (t, J=7.5 Hz, 3H, CH$_3$), 2.59 (s, 3H, CH$_3$), 2.64 (s, 3H, CH$_3$), 2.71 (q, J=7.5 Hz, 2H, CH$_2$), 5.41 (s, 2H, CH$_2$), 6.7–7.6 (m, 23H, Ar), 8.00 (s, 1H, CH=), 8.62 (d, J=4 Hz, 1H, Pyr).

REFERENCE EXAMPLE 20

3-Hydroxy-2-methyl-3-(4-methylphenyl)-3-phenylpropionitrile

Following a similar procedure to that described in reference example 9, but using propionitrile instead of malonitrile, the title compound of this example was obtained (yield: 97%).

$^1$H-NMR (80 MHz, CDCl$_3$) δ (TMS): 1.21 (d d, J=8 Hz, J=1.6 Hz, 3H, CH$_3$), 2.29 (s, 3H, CH$_3$), 3.65 (q, J=8 Hz, 1H, CH), 6.23 (s, 1H, OH), 7.0–7.6 (m,9H,Ar).

REFERENCE EXAMPLE 21

2-Methyl-3-(4-methylphenyl)-3-phenyl-2-propenonitrile

To a solution of 1 g (4 mmol) of the compound obtained in reference example 20 in toluene was added a tip of spatula of p-toluenesulfonic acid and the mixture was stirred at reflux for 2 h using a Dean-Stark water separator. The solvent was removed and the residue was dissolved in ethyl acetate and washed with water. The organic phase was dried and the solvent was removed, to afford 0.8 g of the desired product (yield: 86%).

$^1$H-NMR (80 MHz, CDCl$_3$) δ (TMS): 2.02 (s, 3H, CH$_3$), 2.32 (s, 3H, CH$_3$), 6.9–7.4 (m, 9H, Ar).

REFERENCE EXAMPLE 22

5-[1-Methyl-2-(4-methylphenyl)-2-phenylvinyl]tetrazole

Following a similar procedure to that described in reference example 5, but starting from the compound obtained in reference example 21, the title compound of this example was obtained (yield: 68%).

$^1$H-NMR (80 MHz, CDCl$_3$) δ (TMS): 2.37 (s, 3H, CH$_3$), 2.39 (s, 3H, CH$_3$), 7.0–7.5 (m, 10H, Ar+NH).

REFERENCE EXAMPLE 23

5-[1-Methyl-2-(4-methylphenyl)-2-phenylvinyl]-N-triphenylmethyl

Following the procedure described in reference example 6, but starting from the compound obtained in reference example 22, the title compound of the example was obtained (yield: 80%).

$^1$H-NMR (80 MHz, CDCl$_3$) δ (TMS): 2.19 (s, 0.5×3H, CH$_3$), 2.25 (s, 0.5×3H, CH$_3$), 2.28 (s, 0.5×3H, CH$_3$), 2.34 (s, 0.5×3H, CH$_3$), 6.7–7.5 (m, 24H, Ar).

REFERENCE EXAMPLE 24

5-[2-(4-Bromomethylphenyl)-1-methyl-2-phenylvinyl]-N-triphenylmethyltetrazole

Following the procedure described in reference example 2, but starting from the compound obtained in reference example 23, the title compound of the example was obtained (yield: quantitative).

$^1$H-NMR (80 MHz, CDCl$_3$) δ (TMS): 2.26 (s, 0.5×3H, CH$_3$), 2.35 (s, 0.5×3H, CH$_3$), 4.52 (s, 0.5×2H, CH$_2$), 4.55 (s, 0.5×2H, CH$_2$), 6.7–7.5 (m, 24H, Ar).

REFERENCE EXAMPLE 25

5,7-Dimethyl-2-ethyl-3-[[4-[2-methyl-1-phenyl-2-(N-triphenylmethyltetrazol -5-yl)vinyl]phenyl]methyl]-3H-imidazo[4,5-b]pyridine Following the procedure described in reference example 3, but using the compound obtained in reference example 24 instead of the compound obtained in reference example 2, the title compound of this example was obtained (yield: 49%).

$^1$H-NMR (80 MHz, CDCl$_3$) δ (TMS): 1.26 (t, J=7.5 Hz, 3H, CH$_3$), 2.24 (s, 0.5×3H, CH$_3$), 2.34 (s, 0.5×3H, CH$_3$), 2.42 (s, 3H, CH$_3$), 2.48 (s, 3H, CH$_3$), 2.78 q, J=7.5 Hz, 2H, CH$_2$), 5.33 (s, 0.5×2H, CH$_2$), 5.35 (s, 0.5×2H, CH$_2$), 6.5–7.6 (m, 25H, Ar).

REFERENCE EXAMPLE 26

2,3-Diphenyl-3-(4-methylphenyl)-2-propenonitrile

Following a similar procedure to that described in reference example 9, but using 2-phenylacetonitrile instead of malononitrile, the title compound of the example was obtained (yield: quantitative).

$^1$H-NMR (80 MHz, CDCl$_3$) δ (TMS): 2.28 (s, 0.5×3H, CH$_3$), 2.39 (s, 0.5×3H, CH$_3$), 6.9–7.4 (m, 14H, Ar).

REFERENCE EXAMPLE 27

5-[1,2- Diphenyl-2-(4-methylphenyl)vinyl]tetrazole

Following a similar procedure to that described in reference example 5, but starting from the compound obtained in reference example 26, a crude product was obtained which was chromatographed on silica gel (hexane-ethyl acetate mixtures of increasing polarity) to give 2.56 g of the desired product (yield: 40%).

$^1$H-NMR (80 MHz, CDCl$_3$) δ (TMS): 2.25 (s, 0.5×3H, CH$_3$), 2.35 (s, 0.5×3H, CH$_3$), 6.9–7.4 (m, 15H, Ar+NH).

REFERENCE EXAMPLE 28

5-[1,2-Diphenyl-2-(4-methylphenyl)vinyl]-N-triphenylmethyltetrazole

Following a similar procedure to that described in reference example 6, but starting from the compound obtained in reference example 27, the title compound of this example was obtained (yield: quantitative).

$^1$H-NMR (80 MHz, CDCl$_3$) δ (TMS): 2.20 (s, 0.5×3H, CH$_3$), 2.26 (s, 0.5×3H, CH$_3$), 6.8–7.4 (m, 29H, Ar).

REFERENCE EXAMPLE 29

5-[2-(4-Bromomethylphenyl)-1,2-diphenylvinyl]-N-triphenylmethyltetrazole

Following the procedure described in reference example 2, but starting from the compound obtained in reference example 28, the title compound of this example was obtained (yield: quantitative).

$^1$H-NMR (80 MHz, CDCl$_3$) δ (TMS): 4.36 (s, 0.5×2H, CH$_2$), 4.40 (s, 0.5×2H, CH$_2$), 6.9–7.4 (m, 29H, Ar).

REFERENCE EXAMPLE 30

5,7- Dimethyl-3-[[4-[1,2-diphenyl-2-(N-triphenylmethyltetrazole -5-yl)vinyl]phenyl]methyl]-2-ethyl-3H-imidazo[4,5-b]pyridine Following the procedure described in reference example 3, but using the compound obtained in reference example 29 instead of the compound obtained in reference example 2, the title compound of the example was obtained as a mixture of the cis/trans isomers which were separated by chromatography on silica gel (hexane-ethyl acetate mixtures of increasing polarity), to give a less polar isomer (A, yield: 21%) and a more polar isomer (B, yield: 24%).

Isomer A:
$^1$H-NMR (80 MHz, CDCl$_3$) δ (TMS): 1.20 (t, J=7.5 Hz, 3H, CH$_3$), 2.55 (s, 3H, CH$_3$), 2.62 (s, 3H, CH$_3$), 2.70 (q, J=7.5 Hz, 2H, CH$_2$), 5.34 (s, 2H, CH$_2$), 6.7–7.4 (m, 30H, Ar).

Isomer B:
$^1$H-NMR (80 MHz, CDCl$_3$) δ (TMS): 1.23 (t, J=7.5 Hz, 3H, CH$_3$), 2.55 (s, 3H, CH$_3$), 2.69 (s, 3H, CH$_3$), 2.71 (q, J=7.5 Hz, 2H, CH$_2$), 5.35 (s, 2H, CH$_2$), 6.7–7.4 (m, 30H, Ar).

REFERENCE EXAMPLE 31

2-Ethoxycarbonyl-3-(4-methylphenyl)-3-phenyl-2-propenonitrile

A mixture of 10 g (51 mmol) of 4-methylbenzophenone, 4.9 mL (46 mL (46 mmol) of ethyl cyanoacetate, 0.72 g (9.3 mmol) of ammonium acetate, 2.2 mL (37 mmol) of acetic acid and 8 mL of benzene was heated at reflux for 18 h using a Dean-Stark water separator. Then, 1.1 mL of acetic acid and 0.35 g of ammonium acetate was added and the mixture was heated for 24 h more. The solvent was removed and the residue was dissolved in chloroform and washed with water. The organic phase was dried over magnesium sulfate and the solvent was removed to yield a crude product. This was chromatographed on silica gel (hexane-ethyl acetate mixtures of increasing polarity) to afford 10 g of the title compound of the example as a colourless oil (yield: 67%).

$^1$H-NMR (80 MHz, CDCl$_3$) δ (TMS): 1.10 (t, J=7 Hz, 0.5×3H, CH$_3$), 1.15 (t, J=7 Hz, 0.5×3H, CH$_3$), 2.36 (s, 3H, CH$_3$), 4.10 (q, J=7 Hz, 0.5×2H, CH$_2$), 4.14 (q, J=7 Hz, 0.5×2H, CH$_2$), 7.0–7.5 (m, 9H, Ar).

REFERENCE EXAMPLE 32

3-(4-Bromomethylphenyl)-2-ethoxycarbonyl-3-phenyl-2-propenonitrile

Following the procedure described in reference example 2, but using the compound obtained in reference example 31 instead of the compound obtained in reference example 1, the title compound of this example was obtained (yield: quantitative).

$^1$H-NMR (80 MHz, CDCl$_3$) δ (TMS): 1.15 (t, J=7 Hz, 3H, CH$_3$), 4.15 (q, J=7 Hz, 2H, CH$_2$), 4.46 (s, 2H, CH$_2$), 7.0–7.6 (m, 9H, Ar).

REFERENCE EXAMPLE 33

3-[[4-(2-Cyano-2-ethoxycarbonyl-1-phenylvinyl)phenyl]methyl]-5,7-dimethyl-2-ethyl-3H-imidazo[4,5-b]pyridine Following the procedure described in reference example 3, but using the compound obtained in reference example 32 instead of the compound obtained in reference example 2, the title compound of this example was obtained (yield: 75%).

$^1$H-NMR (80 MHz, CDCl$_3$) δ (TMS): 1.12 (t, J=7.5 Hz, 3H, CH$_3$), 1.31 (t, J=7.5 Hz, 2H, CH$_2$), 4.13 (q, J=7.5 Hz, 2H, CH$_2$), 6.89 (s, 1H, CH=), 7.0–7.5 (m, 10H, Ar).

REFERENCE EXAMPLE 34

4-Toluoyltrifluoromethylbenzene

Following the procedure described in reference example 14, but using 4-trifluoromethylbenzonitrile instead of 2-cyanopyridine, the title compound of this example was obtained (yield: 49%).

$^1$H-NMR (80 MHz, CDCl$_3$) δ (TMS): 2.44 (s, 3H, CH$_3$), 7.1–8.0 (m, 8H, Ar).

REFERENCE EXAMPLE 35

3-Hydroxy-3-(4-methylphenyl)-3-(4-trifluoromethylphenyl)Propionitrile

Following the procedure described in reference example 9, but using the compound obtained in reference example 34 instead of 4-methylbenzophenone and acetonitrile instead of malononitrile, the title compound of this example was obtained (yield: 79%).

$^1$H-NMR (80 MHz, CDCl$_3$) δ (TMS): 2.31 (s, 3H, CH$_3$), 3.20 (s, 2H, CH$_2$), 3.49 (s, 1H, OH), 7.19 (s, 4H, Ar), 7.53 (s, 4H, Ar).

REFERENCE EXAMPLE 36

3-(4-Methylphenyl)-3-(4-trifluoromethylphenyl)propenonitrile

A solution of 6 g (20 mmol) of the compound obtained in reference example 35, 19 mL (0.2 mol) of acetic anhydride and 0.85 g (7 mmol) of 4-dimethylaminopyridine in 54 mL of dichloromethane was stirred at room temperature for 18 h. The resulting mixture was poured into saturated aqueous NaHCO$_3$ and the layers were separated. The aqueous phase was extracted with dichloromethane. The combined organic phases were dried over magnesium sulfate and the solvent was removed, to afford 6.7 g of a crude product.

This crude product was dissolved in 57 mL of toluene, 7.4 mL (49 mmol) of DBU was added and the reaction mixture was heated at reflux for 1 h. It was allowed to cool and was washed with 1N HCl. The organic phase was dried over magnesium sulfate and the solvent was removed, to yield a crude product that was chromatographed on silica gel (hexane-ethyl acetate mixtures of increasing polarity) to afford 3.73 g of the title compound of the example as a colourless oil (yield: 65%).

$^1$H-NMR (80 MHz, CDCl$_3$) δ (TMS): 2.36 (s, 3H, CH$_3$), 5.70 (s, 0.5×1H, CH=), 5.80 (s, 0.5×1H, CH=), 7.10–7.80 (m, 8H, Ar).

REFERENCE EXAMPLE 37

3-(4-Bromomethylphenyl)-3-(4-trifluoromethylphenyl)propenonitrile

Following the procedure described in reference example 2, but using the compound obtained in reference example 36 instead of the compound obtained in reference example 1, the title compound of the example was obtained (yield: quantitative).

$^1$H-NMR (80 MHz, CDCl$_3$) δ (TMS): 4.46 (s, 0.5×2H, CH$_2$), 4.50 (s, 0.5×2H, CH$_2$), 5.76 (s, 0.5×1H, CH=), 5.83 (s, 0.5×1H, CH=), 7.10–7.80 (m, 8H, Ar).

REFERENCE EXAMPLE 38

3-[[4-[2-Cyano-1-(4-trifluoromethylphenyl)vinyl]phenyl]methyl]-5,7-dimethyl-2-ethyl-3H-imidazo[4,5-b]pyridine Following the procedure described in reference example 3, but using the compound obtained in reference example 37 instead of the compound obtained in reference example 2, the title compound of the example was obtained (yield: 76%).

$^1$H-NMR (80 MHz, CDCl$_3$) δ (TMS): 1.33 (t, J=7.5 Hz, 3H, CH$_3$), 2.57 (s, 3H, CH$_3$), 2.62 (s, 3H, CH$_3$), 2.80 (q, J=7.5 Hz, 2H, CH$_2$), 5.47 (s, 0.5×2H, CH$_2$), 5.50 (s, 0.5×2H, CH$_2$), 5.74 (s, 0.5=1H, CH=), 5.79 (s, 0.5×1H, CH=), 6.89 (s, 1H, Pyr), 7.1–7.7 (m, 8H, Ar).

REFERENCE EXAMPLE 39

3-(4-Bromomethylphenyl)-3-phenylpropenonitrile

Following the procedure described in reference example 2, but using the compound obtained in reference example 4 instead of the compound obtained in reference example 1, the title compound of this example was obtained (yield: quantitative).

$^1$H-NMR (80 MHz, CDCl$_3$) δ (TMS): 4.45 (s, 0.5×2H, CH$_2$), 4.50 (s, 0.5×2H, CH$_2$), 5.71 (s, 1H, CH=), 7.10–7.80 (m, 9H, Ar).

REFERENCE EXAMPLE 40

3-[[4-(2-Cyano-1-phenylvinyl)phenyl]methyl]-5,7-dimethyl-2-ethyl-3H-imidazo[4,5-b]pyridine Following the procedure described in reference example 3, but using the compound obtained in reference example 39 instead of the compound obtained in reference example 2, the title compound of the example was obtained (yield: 52%).

$^1$H-NMR (80 MHz, CDCl$_3$) δ (TMS): 1.33 (t, J=7.5 Hz, 3H, CH$_3$), 2.58 (s, 0.5×3H, CH$_3$), 2.59 (s, 0.5×3H, CH$_3$), 2.62 (s, 3H, CH$_3$), 2.79 (q, J=7.5 Hz, 0.5×2H, CH$_2$), 3 2.83 (q, J=7.5 Hz, 0.5×2H, CH$_2$), 5.47 (s, 0.5×2H, CH$_2$), 5.51 (s, 0.5×2H, CH$_2$), 5.51 (s, 0.5×2H, CH$_2$), 5.70 (s, 1H, CH=), 6.90 (s, 1H, Pyr), 7.1–7.7 (m, 9H, Ar).

REFERENCE EXAMPLE 41

3-[[4-(2-Cyano-1-phenylethyl)phenyl]methyl]-5,7-dimethyl-2-ethyl-3H-imidazo[4,5-b]pyridine To a solution of 1.2 g (3 mmol) of the compound obtained in reference example 40 in 6.6 mL of pyridine and 2.2 mL of methanol was slowly added 0.57 g (15 mmol) of sodium borohydride and the mixture was heated at reflux for 24 h. The resulting mixture was poured into 10% HCl and extracted with ethyl acetate. The organic phase was dried over magnesium sulfate and the solvent was removed to afford a crude product. This was chromatographed on silica gel (hexane-ethyl acetate mixtures of increasing polarity) to provide 0.80 g of the title compound of the example as a colourless oil (yield: 68%).

$^1$H-NMR (80 MHz, CDCl$_3$) δ (TMS): 1.28 (t, J=7.5 Hz, 3H, CH$_3$), 2.56 (s, 3H, CH$_3$), 2.61 (s, 3H, CH$_3$), 2.75 (q, J=7.5 Hz, 2H, CH$_2$), 2.95 (d, J=8 Hz, 2H, CH$_2$), 4.30 (t, J=8 Hz, 1H, CH), 5.48 (s, 2H, CH$_2$), 6.86 (s, 1H, Pyr), 7.1–7.4 (m, 9H, Ar).

REFERENCE EXAMPLE 42

3-[[4-[2-Cyano-1-(4-trifluoromethylphenyl)ethyl]phenyl]methyl]-5,7-dimethyl-2-ethyl-3H-imidazo[4,5-b]pyridine Following the procedure described in reference example 41, but using the compound obtained in reference example 38 instead of the compound obtained in reference example 40, the title compound of the example was obtained (yield: 47%).

$^1$H-NMR (80 MHz, CDCl$_3$) δ (TMS): 1.29 (t, J=7.5 Hz, 3H, CH$_3$), 2.56 (s, 3H, CH$_3$), 2.62 (s, 3H, CH$_3$), 2.78 (q, J=7.5 Hz, 2H, CH$_2$), 3.00 (d, J=8 Hz, 2H, CH$_2$), 4.40 (t, J=8 H, 1H, CH), 5.43 (s, 2H, CH$_2$), 6.89 (s, 1H, Pyr), 7.1–7.7 (m, 8H, Ar).

REFERENCE EXAMPLE 43

3-(3-Methylphenyl)-3-phenyl-2-propenonitrile

Following the procedure described in reference example 4, but using 3-methylbenzophenone instead of 4-methylbenzophenone, the title compound of the example was obtained (yield: 75%).

$^1$H-NMR (80 MHz, CDCl$_3$) δ (TMS): 2.35 (s, 3H, CH$_3$), 5.67 (s, 1H, CH=), 7.29 (m, 9H, Ar).

REFERENCE EXAMPLE 44

3-(3-Bromomethylphenyl)-3-phenyl-2-propenonitrile

Following the procedure described in reference example 2, but using the compound obtained in reference example 43 instead of the compound obtained in reference example 1, the title compound of the example was obtained (yield: quantitative).

$^1$H-NMR (80 MHz, CDCl$_3$) δ (TMS): 4.44 (s, 0.5×2H, CH$_2$), 4.49 (s, 0.5×2H, CH$_2$), 5.74 (s, 1H, CH=), 7.10–7.80 (m, 9H, Ar).

REFERENCE EXAMPLE 45

3-[[3-(2-Cyano-1-phenylvinyl)phenyl]methyl]-5,7-dimethyl-2-ethyl-3H-imidazole[4,5-b]pyridine Following the procedure described in reference example 3, but using the compound obtained in reference example 44 instead of the compound obtained in reference example 2, the title compound of the example was obtained (yield: 52%).

$^1$-NMR (80 MHz, CDCl$_3$) δ (TMS): 1.33 (t, J=7.5 Hz, 3H, CH$_3$), 2.54 (s, 3H, CH$_3$), 2.62 (s, 3H, CH$_3$), 2.79 (q, J=7.5 Hz, 0.5×2H, CH$_2$), 2.83 (q, J=7.5 Hz, 0.5×2H, CH$_2$), 5.41 (s, 0.55×2H, CH$_2$), 5.47 (s, 0.5×2H, CH$_2$), 5.65 ((s, 0.5×1H, CH=), 5.72 (s, 0.5×1H, CH=), 6.90 (s, 1H, Pyr), 7.1–7.7 (m, 9H, Ar).

REFERENCE EXAMPLE 46

3-[[3-(2-Cyano-1-phenylvinyl)phenyl]methyl]-5,7-dimethyl-2-ethyl-3H-imidazo[4,5-b]pyridine A mixture of 1.0 g (2.1 mmol) of the product obtained in reference example 33, 0.165 g (4.2 mmol) of sodium borohydride and 10 mL of ethanol was stirred at room temperature for 18 h. Then, 3 mL of water was added and the solvents were removed. The residue was extracted with ethyl acetate. The organic solution was dried over magnesium sulfate and the solvent was removed, to afford a crude product that was chromatographed on silica gel (hexane-ethyl acetate mixtures of increasing polarity) to give a faster-running fraction (isomer A, yield: 33%) and a more polar fraction (isomer B, yield: 26%).

Isomer A:

$^1$H-NMR (80 MHz, CDCl$_3$) δ (TMS): 1.24 (t, J=7 Hz, 3H, CH$_3$), 2.55 (s, 3H, CH$_3$), 2.59 (s, 3H, CH$_3$), 2.73 (q, J=7 Hz, 2H, CH$_2$), 3.40 (m, 1H, CH), 3.63 (m, 2H, CH$_2$), 4.29 (d, J=8 Hz, 1H, CH), 5.40 (s, 2H, CH$_2$), 6.8–7.3 (m, 11H, Ar+OH)

Isomer B:

$^1$H-NMR (80 MHz, CDCl$_3$) δ (TMS): 1.24 (t, J=7 Hz, 3H, CH$_3$), 2.55 (s, 3H, CH$_3$), 2.59 (s, 3H, CH$_3$), 2.73 (q, J=7 Hz, 2H, CH$_2$), 3.40 (m, 1H, CH), 3.60 (m, 2H, CH$_2$), 4.29 (d, J=8 Hz, 1H, CH), 5.39 (s, 2H, CH$_2$), 6.8–7.3 (m, 11H, Ar+OH)

REFERENCE EXAMPLE 47

3-(4-Methyl phenyl)-2-methylthio-3-phenyl-2-propenonitrile

Following the procedure described in reference example 9, but using methylthioacetonitrile instead of malononitrile, the title compound of the example was obtained (yield: 97%).

$^1$H-NMR (80 MHz, CDCl$_3$) δ (TMS): 2.38 (s, 3H, CH$_3$), 2.48 (s, 3H, CH$_3$), 6.9–7.4 (m, 9H, Ar).

REFERENCE EXAMPLE 48

2-Bromo-3-(4-methylphenyl)-3-phenyl-2-propenonitrile

To a solution of 3.5 g (16.1 mmol) of the compound obtained in reference example 4 in 14 mL of chloroform was added 0.84 mL of Br$_2$ (16.1 mmol) and the mixture was stirred at reflux for 1 h. After removal of the solvent, 4.472 g of the desired product was obtained (yield: 94%).

$^1$H-NMR (80 MHz, CDCl$_3$) δ (TMS): 2.38 (s, 3H, CH$_3$), 7.1–7.5 (m, 9H, Ar).

REFERENCE EXAMPLE 49

2-Bromo-3-(4-bromomethylphenyl)-3-phenyl-2-propenonitrile

Following a similar procedure to that described in reference example 2, but starting from the compound obtained in reference example 48, the title compound of this example was obtained (yield: quantitative).

$^1$H-NMR (80 MHz, CDCl$_3$) δ (TMS): 4.47 (s, 0.5×2H, CH$_2$), 4.48 (s, 0.5×2H, CH$_2$), 7.2–7.6 (m, 9H, Ar).

REFERENCE EXAMPLE 50

3-[[4-(2-Bromo-2-cyano-1-phenylvinyl)phenyl]methyl]-5,7-dimethyl-2-ethyl-3H-imidazo[4,5-b]pyridine Following a similar procedure to that described in reference example 3, but starting from the compound obtained in reference example 49, the title compound of this example was obtained (yield: 50%).

$^1$H-NMR (80 MHz, CDCl$_3$) δ (TMS): 1.30 (t, J=7.5 Hz, 3H, CH$_3$), 2.58 (s, 3H, CH$_3$), 2.62 (s, 3H, CH$_3$), 2.78 (q, J=7.5 Hz, 2H, CH$_2$), 5.47 (s, 2H, CH$_2$), 6.89 (s, 1H, Pry), 7.0–7.5 (m, 9H, Ar).

REFERENCE EXAMPLE 51

Ethyl 2-bromo-3-(4-methylphenyl)-3-phenyl-2-propenoate

Following a similar procedure to that described in reference example 48, but starting from the compound obtained in reference example 1, the title compound of this example was obtained.

$^1$H-NMR (80 MHz, CDCl$_3$) δ (TMS): 0.96 (t, J=7.1 Hz, 0.5×3H, CH$_3$), 1.02 (t, J=7.1 Hz, 0.5×3H, CH$_3$), 2.36 (s, 0.5×3H, CH$_3$), 2.36 (s, 0.5×3H, CH$_3$), 4.02 (q, J=7.1 Hz, 0.5×2H, CH$_2$), 4.06 (q, J=7.1 Hz, 0.5×2H, CH$_2$), 7.0–7.5 (m, 9H, Ar).

REFERENCE EXAMPLE 52

Ethyl 2-bromo-3-(4-bromomethylphenyl)-3-phenyl-2-propenoate

Following a similar procedure to that described in reference example 2, but starting from the compound obtained in reference example 51, the title compound of this example was obtained.

$^1$H-NMR (80 MHz, CDCl$_3$) δ (TMS): 0.97 (t, J=7 Hz, 0.5×3H, CH$_3$), 0.99 (t, J=7 Hz 0.5×3H, CH$_3$), 4.04 (q, J=7 Hz, 2H, CH$_2$), 4.44 (s, 0.5×2H, CH$_2$), 4.48 (s, 0.5×2H, CH$_2$, 7.0–7.6 (m, 9H, Ar).

REFERENCE EXAMPLE 53

3-[[4-(2-Chloro-2-cyano-1-phenyl)vinyl)phenyl]methyl]-5,7-dimethyl-2-ethyl-3H-imidazo[4,5-b]pyridine To a solution of 0.4 g (1 mmol) of the compound obtained in reference example 40 in 1.76 mL of acetic acid was added 0.088 mL (1.08 mmol) of sulfuryl chloride and the reaction mixture was heated at 60°–85° C. for 1 h. Next, it was allowed to cool to room temperature and was poured into a cold solution of sodium bicarbonate. The mixture was extracted with ethyl acetate, the organic phase was dried and the solvent was removed to give a crude product, which was purified by chromatography on silica gel (ethyl acetate-hexane mixtures of increasing polarity) to afford the title compound of the example (yield: 82%).

$^1$H-NMR (80 MHz, CDCl$_3$) δ (TMS): 1.31 (t, J=7.4 Hz, 3H, CH$_3$), 2.58 (s, 3H, CH$_3$), 2.63 (s, 3H, CH$_3$), 2.79 (q, J=7.4 Hz, 2H, CH$_2$), 5.47 (s, 2H, CH$_2$), 6.89 (s, 1H, Pry), 7.0–7.5 (m, 9H, Ar).

REFERENCE EXAMPLES 54–59

Following a procedure similar to that described in reference example 14, but using the appropriate nitriles instead of 2-cyanopyridine, the compounds shown in the following table were prepared:

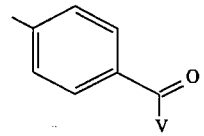

| Example No. | V | $^1$H-NMR(80MHz, CDCl$_3$)δ(TMS) |
|---|---|---|
| 54 | 2-fluorophenyl | 2.42(s, 3H, CH$_3$), 7.0–7.8(m, 8H, Ar) |
| 55 | 2-thienyl | 2.42(s, 3H, CH$_3$), 7.0–7.4(m, 3H, Ar), 7.5–7.8(m, 4H, Ar) |
| 56 | 2-chlorophenyl | 2.42(s, 3H, CH$_3$), 7.1–7.8(m, 8H, Ar) |
| 57 | 4-methoxyphenyl | 2.43(s, 3H, CH$_3$), 3.88(s, 3H, CH$_3$), 6.95(d, J=8.8Hz, 2H, Ar), 7.26(d, J=8Hz, 2H, Ar), 7.68(d, J=8Hz, 2H, Ar), 7.81(d, J=8.8Hz, 2H, Ar). |
| 58 | 4-pyridyl | 2.44(s, 3H, CH$_3$), 7.2–7.8(m, 6H, Ar), 8.82(m, 2H, Pyr) |
| 59 | 2,4-difluorophenyl | 2.39(s, 3H, CH$_3$), 6.7–7.8(m, 7H, Ar) |

REFERENCE EXAMPLES 60–64

Following a procedure similar to that described in reference example 4, but starting from the compounds obtained in reference examples 54–58, the compounds shown in the following table were prepared:

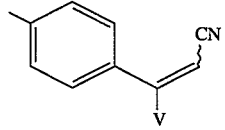

| Example No. | V | $^1$H-NMR(80MHz, CDCl$_3$)δ(TMS): |
|---|---|---|
| 60 | 2-fluorophenyl | 2.34(s, 0.7×3H, CH$_3$), 2.37(s, 0.3×3H, CH$_3$), 5.71(s, 0.3×1H, CH=), 5.89(s, 0.7×1H, CH=), 6.9–7.5(m, 8H, Ar) |
| 61 | 2-thienyl | 2.36(s, 0.5×3H, CH$_3$), 2.41(s, 0.5×3H, CH$_3$), 5.36(s, 0.5×1H, CH=), 5.69(s, 0.5×1H, CH=), 6.9–7.9(m, 7H, Ar) |
| 62 | 2-chlorophenyl | 2.46(s, 3H, CH$_3$), 5.34(s, 1H, CH=), 6.7–7.2(m, 8H, Ar) |
| 63 | 4-methoxyphenyl | 2.38(s, 0.5×3H, CH$_3$), 2.40(s, 0.5×3H, CH$_3$), 3.82(s, 0.5×3H, CH$_3$), 3.85(s, 0.5×3H, CH$_3$), 5.57 (s, 0.5×1H, CH=), 5.60(s, 0.5×1H, CH=), 6.8–7.5(m, 8H, Ar) |
| 64 | 4-pyridyl | 2.37(s, 0.5×3H, CH$_3$), 2.42(s, 0.5×3H, CH$_3$), 5.77(s, 0.5×1H, CH=), 5.84(s, 0.5×1H, CH=), 7.0–7.4(m, 6H, Ar), 8.65(m, 2H, Pyr) |

REFERENCE EXAMPLES 65–69

Following a procedure similar to that described in reference example 2, but starting from the compounds obtained in reference examples 60–64, the compounds shown in the following table were prepared:

| Example No. | V | ¹H-NMR(80MHz, CDCl₃)δ(TMS): |
|---|---|---|
| 65 | 2-fluorophenyl | 4.45(s, 0.3×2H, CH₂), 4.47(s, 0.7×2H, CH₂), 5.79(s, 0.3×1H, CH=), 5.91(s, 0.7×1H, CH=), 7.0–7.6(m, 8H, Ar) |
| 66 | 2-thienyl | 4.53(s, 2H, CH₂), 5.42(s, 0.5×1H, CH=), 5.80(s, 0.5×1H, CH=), 7.0–8.2(m, 7H, Ar) |
| 67 | 2-chlorophenyl | 4.45(s, 2H, CH₂), 6.01(s, 1H, CH=), 7.0–7.6(m, 8H, Ar) |
| 68 | 4-methoxyphenyl | 3.83(s, 0.5×3H, CH₃), 3.85(s, 0.5×3H, CH₃), 4.49(s, 0.5×2H, CH₂), 4.52(s, 0.5×2H, CH₂), 5.67(s, 0.5×1H, CH=), 5.69(s, 0.5×1H, CH=), 6.8–7.8(m, 8H, Ar) |
| 69 | 4-pyridyl | 4.46(s, 0.5×2H, CH₂), 4.52(s, 0.5×2H, CH₂), 6.40(s, 0.5×1H, CH=), 6.43(s, 0.5×1H, CH=), 7.1–7.6(m, 6H, Ar), 8.5–8.9(m, 2H, Pyr) |

REFERENCE EXAMPLES 70–74

Following a procedure similar to that described in reference example 3, but starting from the compounds obtained in reference examples 65–69, the compounds shown in the following table were prepared:

| Example No. | V | ¹H-NMR(80MHz, CDCl₃)δ(TMS): |
|---|---|---|
| 70* | 2-fluorophenyl | isomer A: 1.31(t, J=7.5Hz, 3H, CH₃), 2.58(s, 3H, CH₃), 2.62(s, 3H, CH₃), 2.80(q, J=7.5Hz, 2H, CH₂), 5.49(s, 2H, CH₂), 5.77(s, 1H, CH=), 6.88(s, 1H, Pyr), 7.0–7.5(m, 8H, Ar) isomer B: 1.30(t, J=7.5Hz, 3H, CH₃), 2.56(s, 3H, CH₃), 2.62(s, 3H, CH₃), 2.76(q, J=7.5Hz, 2H, CH₂), 5.46(s, 2H, CH₂), 5.90(s, 1H, CH=), 6.88(s, 1H, Pyr), 7.0–7.5(m, 8H, Ar) |
| 71 | 2-thienyl | 1.32(t, J=7.3Hz, 3H, CH₃), 2.58(s, 3H, CH₃), 2.63(s, 3H, CH₃), 2.73(q, J=7.3Hz, 2H, CH₂), 5.35(s, 0.5×1H, CH=), 5.52(s, 2H, CH₂), 5.72(s, 0.5×1H, CH=), 6.8–7.9(m, 8H, Ar) |
| 72 | 2-chlorophenyl | 1.30(t, J=7.4Hz, 3H, CH₃), 2.56(s, 3H, CH₃), 2.61(s, 3H, CH₃), 2.74(q, J=7.4Hz, 2H, CH₂), 5.46(s, 2H, CH₂), 5.97(s, 1H, CH=), 6.88(s, 1H, Pyr), 7.0–7.5(m, 8H, Ar) |
| 73 | 4-methoxyphenyl | 1.32(t, J=7.5Hz, 3H, CH₃), 2.59(s, 3H, CH₃), 2.63(s, 3H, CH₃), 2.79(q, J=7.5Hz, 0.5×2H, CH₂), 2.82(q, J=7.5Hz, 0.5×2H, CH₂), 3.82(s, 0.5×3H, CH₃), 3.84(s, 0.5×3H, CH₃), 5.47(s, 0.5×2H, CH₂), 5.51(s, 0.5×2H, CH₂), 5.55(s, 0.5×1H, CH=), 5.63(s, 0.5×1H, CH=), 6.8–7.4(m, 9H, Ar) |
| 74 | 4-pyridyl | 1.33(t, J=7.4Hz, 3H, CH₃), 2.57(s, 3H, CH₃), 2.62(s, 3H, CH₃), 2.79(q, J=7.4Hz, 0.5×2H, CH₂), 2.82(q, J=7.4Hz, 0.5×2H, CH₂), 5.47(s, 0.5×2H, CH₂), 5.51(s, 0.5×2H, CH₂), 5.81(s, 0.5×1H, CH=), 5.83(s, 0.5×1H, CH=), 6.89(s, 1H, Pyr), 7.1–7.4(m, 6H, Ar), 8.69(m, 2H, Pyr). |

*The mixture of isomers was separated by chromatography on silica gel (hexane-ethyl acetate mixtures of increasing polarity), to give a less polar isomer (A) and a more polar isomer (B).

REFERENCE EXAMPLES 75–78

Following a procedure similar to that described in reference example 41, but starting from the compounds obtained in reference examples 70 and 72–74, the compounds shown in the following table were prepared:

| Example No. | V | ¹H-NMR(80MHz, CDCl₃)δ(TMS): |
|---|---|---|
| 75 | 2-fluorophenyl | 1.28(t, J=7.5Hz, 3H, CH₃), 2.57(s, 3H, CH₃), 2.61(s, 3H, CH₃), 2.76(q, J=7.5Hz, 2H, CH₂), 3.02(d, J=7.7Hz, 2H, CH₂), 4.62(t, J=7.7Hz, 1H, CH), 5.42(s, 2H, CH₂), 6.8–7.4(m, 9H, Ar) |
| 76 | 2-chlorophenyl | 1.29(t, J=7.4Hz, 3H, CH₃), 2.57(s, 3H, CH₃), 2.62(s, 3H, CH₃), 2.79(q, J=7.4Hz, 2H, CH₂), 2.98(d, J=7.6Hz, 2H, CH₂), 4.85(t, J=7.6Hz, 1H, CH), 5.43(s, 2H, |

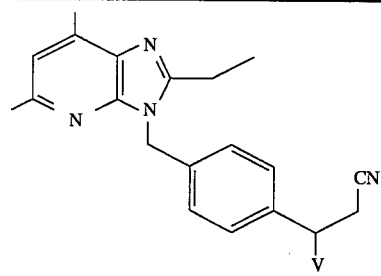

| Example No. | V | $^1$H-NMR(80MHz, CDCl$_3$)δ(TMS): |
|---|---|---|
| 77 | 4-methoxyphenyl | CH$_2$), 6.8–7.5(m, 9H, Ar) *1.28(t, J=7.5Hz, 3H, CH$_3$), 2.63(s, 6H, 2CH$_3$), 3.07(q, J=7.5Hz, 2H, CH$_2$), 3.11(d, J=7.7Hz, 2H, CH$_2$), 3.73(s, 3H, CH$_3$), 4.33(t, J=7.7Hz, 1H, CH), 5.65(s, 2H, CH$_2$), 6.7–7.5 (m, 9H, Ar) |
| 78 | 4-pyridyl | 1.29(t, J=7.5Hz, 3H, CH$_3$), 2.56(s, 3H, CH$_3$), 2.61(s, 3H, CH$_3$), 2.76(q, J=7.5Hz, 2H, CH$_2$), 2.98(d, J=7.5Hz, 2H, CH$_2$), 4.29(t, J=7.5Hz, 1H, CH), 5.42(s, 2H, CH$_2$), 6.8–7.3 (m, 7H, Ar), 8.50(m, 2H, Pyr). |

*CD$_3$OD was used as solvent

REFERENCE EXAMPLES 79–83

Following a procedure similar to that described in reference example 1, but starting from the compounds obtained in reference examples 54 and 56–59, the compounds shown in the following table were prepared:

| Example No. | V | $^1$H-NMR(80MHz, CDCl$_3$)δ(TMS): |
|---|---|---|
| 79 | 2-fluorophenyl | 1.12(t, J=7Hz, 3H, CH$_3$), 2.35(s, 3H, CH$_3$), 4.06(q, J=7Hz, 2H, CH$_2$), 6.48(s, 1H, CH=), 7.0–7.5 (m, 8H, Ar). |
| 80 | 2-chlorophenyl | 1.09(t, J=7.2Hz, 3H, CH$_3$), 2.34(s, 3H, CH$_3$), 4.03(q, J=7.2Hz, 2H, CH$_2$), 6.52(s, 1H, CH=), 7.0–7.5 (m, 8H, Ar). |
| 81 | 4-methoxyphenyl | 1.12(br t, 3H, CH$_3$), 2.34(br s, 3H, CH$_3$), 3.79(s, 3H, CH$_3$), 4.04(br q, 2H, CH$_2$), 6.25(s, 1H, CH=), 6.7–7.4(m, 8H, Ar). |
| 82 | 4-pyridyl | 1.10(t, J=7Hz, 0.5×3H, CH$_3$), 1.14 (t, J=7Hz, 0.5×3H, CH$_3$), 2.33(s, 0.5×3H, CH$_3$), 2.38(s, 0.5×3H, CH$_3$), 4.05(m, 2H, CH$_2$), 6.42(s, 1H, CH=), 7.0–7.6(m, 6H, Ar), 8.5–8.9 (m, 2H, Pyr). |
| 83 | 2,4-difluorophenyl | 1.14(t, J=7Hz, 3H, CH$_3$), 2.32(s, 3H, CH$_3$), 4.07(q, J=7Hz, 0.5×2H, CH$_2$), 4.10(q, J=7Hz, 0.5×2H, CH$_2$), 6.56(s, 1H, CH=), 6.6–7.3 (m, 7H, Ar). |

REFERENCE EXAMPLES 84–88

Following a procedure similar to that described in reference example 2, but starting from the compounds obtained in reference examples 79–83, the compounds shown in the following table were prepared:

| Example No. | V | $^1$H-NMR(80MHz, CDCl$_3$)δ(TMS): |
|---|---|---|
| 84 | 2-fluorophenyl | 1.13(t, J=7.1Hz, 3H, CH$_3$), 4.06(q, J=7.1Hz, 2H, CH$_2$), 4.44(s, 2H, CH$_2$), 6.47(s, 1H, CH=), 7.0–7.6 (m, 8H, Ar). |
| 85 | 2-chlorophenyl | 1.10(t, J=7.1Hz, 3H, CH$_3$), 4.05(q, J=7.1Hz, 2H, CH$_2$), 4.47(s, 2H, CH$_2$), 6.55(s, 1H, CH=), 7.1–7.6 (m, 8H, Ar). |
| 86 | 4-methoxyphenyl | 1.11(t, J=7.3Hz, 0.5×3H, CH$_3$), 1.16(t, J=7.3Hz, 0.5×3H, CH$_3$), 3.81(s, 0.5×3H, CH$_3$), 3.83(s, 0.5×3H, CH$_3$), 4.03(q, J=7.3Hz, 0.5×2H, CH$_2$), 4.07(q, J=7.3Hz, 0.5×2H, CH$_2$), 4.46(s, 0.5×2H, CH$_2$), 4.52(s, 0.5×2H, CH$_2$), 6.25(s, 0.5×1H, CH=), 6.28(s, 0.5×1H, CH=), 6.7–7.6(m, 8H, Ar). |
| 87 | 4-pyridyl | 1.11(t, J=7Hz, 3H, CH$_3$), 4.04(q, J=7Hz, 2H, CH$_2$), 4.44(s, 0.5×2H, CH$_2$), 4.49(s, 0.5×2H, CH$_2$), 6.42(s, 0.5×1H, CH=), 6.45(s, 0.5×1H, CH=), 7.0–8.2(m, 6H, Ar), 8.62(m, 2H, Pyr). |
| 88 | 2,4-difluorophenyl | 1.21(t, J=7.1Hz, 3H, CH$_3$), 4.12(q, J=7.1Hz, 0.5×2H, CH$_2$), 4.15(q, J=7.1Hz, 0.5×2H, CH$_2$), 4.49(s, 2H, CH$_2$), 6.52(s, 1H, CH=), 6.8–7.7(m, 7H, Ar) |

REFERENCE EXAMPLE 89

3-(4-Bromomethylphenyl)-2-methylthio-3-phenyl-2-propenonitrile

Following a similar procedure to that described in reference example 2, but starting from the compound obtained in reference example 47, the title compound of the example was obtained (yield: 48%).

$^1$H-NMR (80 MHz, CDCl$_3$) δ (TMS): 2.46 (s, 3H, CH$_3$), 4.44 (s, 2H, CH$_2$), 7.1–7.5 (m, 9H, Ar).

REFERENCE EXAMPLE 90

3-[[4-[2-Cyano-2-(methylthio)-1-phenylvinyl]phenyl]methyl]-5,7-dimethyl-2-ethyl-3H-imidazo[4,5-b]pyridine Following a similar procedure to that described in reference example 3, but starting from the compound obtained in reference example 89, the title compound of the example was obtained as a mixture of isomers (yield: 78%).

$^1$-HMR (80 MHz, CDCl$_3$) δ (TMS): 1.30 (t, J=7.4 Hz, 3H, CH$_3$), 2.46 (s, 3H, CH$_3$), 2.57 (s, 3H, CH$_3$), 2.62 (s, 3H, CH$_3$), 2.78 (q, J=7.4 Hz, 2H, CH$_2$), 5.26 (s, 2H, CH$_2$), 6.88 (s, 1H, Pyr), 7.1–7.5 (m, 9H, Ar).

REFERENCE EXAMPLE 91

Diethyl (4-methylphenyl)phenylmethylidenemalonate

To a solution of 7.9 mL of diisopropylamine (56.13 mmol) in 100 mL of anhydrous tetrahydrofuran, cooled to −78° C., was added 35 mL of BuLi (56.13 mmol) and the resulting mixture was stirred for 10 min. Next, 5 g (18.79 mmol) of the compound obtained in reference example 1 dissolved in 50 mL of tetrahydrofuran was carefully added and the reaction mixture was stirred for further 15 min. Finally, the reaction mixture was slowly added to a solution of diethyl carbonate (9.1 mL, 74.17 mmol) in diethyl ether (100 mL), cooled with an ice bath. The resulting mixture was allowed to warm up to room temperature, some drops of water were added and the solvents were removed. The residue was taken up in diethyl ether and washed with 1N HCl. The organic phase was dried and the solvent was removed to yield a crude product that was chromatographed on silica gel (hexane-ethyl acetate, 10%) to provide 2.54 g of the desired product (yield: 40%).

$^1$H-NMR (80 MHz, CDCl$_3$) δ (TMS): 1.00 (t, J=7.1 Hz, 3H, CH$_3$), 1.06 (t, J=7.1 Hz), 3H, CH$_3$), 2.34 (s, 3H, CH$_3$), 4.05 (q, J=7.1 Hz, 2H, CH$_2$), 4.10 (q, J=7.1 Hz, 2H, CH$_2$), 7.0–7.5 (, 9H, Ar).

REFERENCE EXAMPLE 92

Diethyl (4-Bromomethylphenyl)phenylmethylidenemalonate

Following a similar procedure to that described in reference example 2, but starting from the compound obtained in reference example 91, the title compound of this example was obtained (yield: 80%)

$^1$H-NMR (80 MHz, CDCl$_3$) δ (TMS): 1.02 (t, J=7.1 Hz, 3H, CH$_3$), 1.03 (t, J=7.1 Hz, 3H, CH$_3$), 4.06 (q, J=7.1 Hz, 4H, 2CH$_2$), 4.46 (s, 2H, CH$_2$), 7.1–7.5 (m, 9H, Ar).

REFERENCE EXAMPLE 93

3-[[4-(3-Amino-1-phenylpropyl)phenyl]methyl]-5,7-dimethyl -2-ethyl-3H-imidazo[4,5-b]pyridine To a solution of 0.2 g (5.2 mmol) of LiAlH$_4$ in 9 mL of diethyl ether, cooled with an ice bath, was added dropwise 0.5 g (1.3 mmol) of the compound obtained in reference example 40 dissolved in 3 mL of diethyl ether and the resulting mixture was stirred under argon at room temperature for 2 h. Tetrahydrofuran was added until complete dissolution of the paste obtained and the resulting solution was stirred at room temperature for 3 h. Then, it was cooled with an ice bath and 0.34 mL of water and 0.68 mL of tetrahydrofuran was added, followed by 0.34 mL of 15% aqueous NaOH and finally 0.9 mL of water. The precipitate formed was filtered, washed with tetrahydrofuran and the solvent was removed. Finally, chloroform was added, and the resulting solution was dried over sodium sulfate and the solvent was removed to afford a crude product. This was purified by chromatography on silica gel (chloroform-methanol-ammonia mixtures of increasing polarity) to give the title compound of the example (yield: 42%).

$^1$H-NMR (80 MHz, CDCl$_3$) δ (TMS): 1.27 (t, J=7.5 Hz, 3H, CH$_3$), 1.4 (br s, NH$_2$), 2.13 (m, 2H, CH$_2$), 2.57 (s, 3H, CH$_3$), 2.61 (s, 3H, CH$_3$), 2.76 (q, J=7.5 Hz, 2H, CH$_2$), 2.5–2.8 (m, 2H, CH$_2$), 3.98 (t, J=7.7 Hz, 1H, CH), 5.39 (s, 2H, CH$_2$), 6.87 (s, 1H, Pry), 7.0–7.4 (m, 9H, Ar).

REFERENCE EXAMPLE 94

Diethyl (4-methylphenyl)methylidenemalonate

A mixture of 19.6 mL (166.4 mmol) of p-tolualdehyde, 23.8 mL (158.8 mmol) of diethyl malonate, 0.5 mL of piperidine and 50 mL of benzene was heated at reflux for 18 h using a Dean-Stark water separator. The mixture was allowed to cool to room temperature, benzene was added and it was washed with water (2×), 1N HCl (2×) and NaHCO$_3$. The aqueous phase was extracted with ethyl acetate, the organic phase was dried and the solvent was removed, to yield 41.2 g of the desired product (yield: 99%).

$^1$H-NMR (80 MHz, CDCl$_3$) δ (TMS): 1.24 (t, J=6.4 Hz, 3H, CH$_3$), 1.27 (t, J=6.4 Hz, 3H, CH$_3$), 2.31 (s, 3H, CH$_3$), 4.22 (q, J=6.4 Hz, 2H, CH$_2$), 4.28 (q, J=6.4 Hz, 2H, CH$_2$), 7.0–7.3 (m, 4H, Ar), 7.88 (s, 1H, CH═).

REFERENCE EXAMPLE 95

Diethyl (4-bromomethylphenyl)methylidenemalonate

Following a similar procedure to that described in reference example 2, but starting from the compound obtained in reference example 94, the title compound of the example was obtained (yield: quantitative).

$^1$H-NMR (80 MHz, CDCl$_3$) δ (TMS): 1.28 (t, J=7 Hz, 3H, CH$_3$), 1.32 (t, J=7 Hz, 3H, CH$_3$), 4.29 (q, J=7 Hz, 4H, 2CH$_2$), 4.43 (s, 2H, CH$_2$), 7.39 (m, 4H, Ar), 7.65 (s, 1H, CH═).

REFERENCE EXAMPLE 96

5,7-Dimethyl-3-[[4-[2,2-bis(ethoxycarbonyl)vinyl]phenyl] methyl]-2-ethyl-3H-imidazo[4,5-b]pyridine 5,7-Dimethyl-3-[[4-[2,2-bis(ethoxycarbonyl)vinyl]phenyl]methyl]-2-ethyl-3H-imidazo[4,5-b]pyridine Following a similar procedure to that described in reference example 3, but starting from the compound obtained in reference example 95, the title compound of this example was obtained (yield: 65%).

$^1$H-NMR (80 MHz, CDCl$_3$) δ (TMS): 1.26 (t, J=7 Hz, 3H, CH$_3$), 1.30 (J=7 Hz, 3H, CH$_3$), 1.32 (t, J=7 Hz, 3H, CH$_3$), 2.54 (s, 3H, CH$_3$), 2.64 (s, 3H, CH$_3$), 2.8 (q, J=7 Hz, 2H, CH$_2$), 4.21 (q, J=7 Hz, 4H, 2CH$_2$), 5.46 (s, 2H, CH$_2$), 6.9 (s, 1H, Pyr), 7.5–7.0 (m, 4H, Ar), 7.67 (s, 1H, CH═).

REFERENCE EXAMPLE 97

2-Ethoxycarbonyl-3-(4-methylphenyl)-2-propenonitrile

Following a similar procedure to that described in reference example 31, but using p-tolualdehyde instead of 4-methylbenzophenone, the title compound of this example was obtained (yield: 65%).

$^1$H-NMR (80 MHz, CDCl$_3$) δ (TMS): 1.41 (t, J=7.2 Hz, 3H, CH$_3$), 2.44 (s, 3H, CH$_3$), 4.39 (q, J=7.2 Hz, 2H, CH$_2$), 7.61 (AX quartet, Δv=0.594, J=8.2 Hz, 4H, Ar), 8.22 (s, 1H, CH═).

REFERENCE EXAMPLE 98

3-(4-Bromomethylphenyl)-2-ethoxycarbonyl-2-propenonitrile

Following a similar procedure to that described in reference example 2, but starting from the compound obtained in reference example 97, the title compound of this example was obtained (yield: quantitative).

$^1$H-NMR (80 MHz, CDCl$_3$) δ (TMS): 1.40 (t, J=7.1 Hz, 3H, CH$_3$), 4.39 (q, J=7.1 Hz, 2H, CH$_2$), 4.50 (s, 2H, CH$_2$), 7.2–8.1 (m, 4H, Ar), 8.33 (s, 1H, CH═).

REFERENCE EXAMPLE 99

3-[[4-(2-Cyano-2-ethoxycarbonylvinyl) phenyl]methyl]-5,7-dimethyl-2-ethyl-3H-imidazo[4,5-b]pyridine Following a similar procedure to that described in reference example 3, but starting from the compound obtained in reference example 98, the title compound of this example was obtained (yield: 18%).

$^1$H-NMR (80 MHz, CDCl$_3$) δ (TMS): 1.1–1.5 (m, 6H, 2CH$_3$), 2.57 (s, 3H, CH$_3$), 2.63 (s, 3H, CH$_3$), 2.77 (q, J=7.4 Hz, 2H, CH$_2$), 4.27 (q, J=7 Hz, 2H, CH$_2$), 5.51 (s, 2H, CH$_2$), 6.9 (s, 1H, Pry), 7.1–8.1 (m, 4H, Ar), 8.18 (s, 1H, CH═).

REFERENCE EXAMPLE 100

Ethyl 3-(4-methylphenyl)-3-phenylpropanoate

To a solution of 10 g (37.6 mmol) of the compound obtained in reference example 1 in 200 mL of ethanol was added 1 g of 10% Pd/C and the mixture was hydrogenated at atmospheric pressure overnight. The mixture was filtered through celite, washed with ethanol and the solvent was removed to afford 8.25 g of the title compound of this example (yield: 82%).

$^1$H-NMR (80 MHz, CDCl$_3$) δ (TMS): 1.10 (t, J=7.1 Hz, 3H, CH$_3$), 2.29 (s, 3H, CH$_3$), 3.02 (d, J=8.1 Hz, 2H, CH$_2$), 4.03 (q, J=7.1 Hz, 2H, CH$_2$), 4.51 (t, J=8.1 Hz, 1H, CH), 7.10 (s, 4H, Ar), 7.23 (s, 5H, Ar).

REFERENCE EXAMPLE 101

Ethyl 2,2-dimethyl-3-(4-methylphenyl)-3-phenylpropanoate a) Ethyl 2-methyl-3-(4-methylphenyl)-3-phenylpropanoate To a solution of 4.4 mL (7.4 mmol) of BuLi in 10 mL of dry tetrahydrofuran, cooled with an ice bath, was added 1 mL of diisopropylamine and the resulting mixture was stirred for 10 min. Next, the mixture was cooled to –40° C., 1 g (3.7 mmol) of the compound obtained in reference example 100 dissolved in 2 mL of tetrahydrofuran was added and the resulting mixture was stirred for some more minutes. Finally, 1.4 mL (22.2 mmol) of methyl iodide was added and the mixture was stirred at room temperature for 2 days. Some drops of water were added, and it was diluted with ethyl acetate and washed with water and 1N HCl. The organic phase was dried and the solvent was removed to afford 1 g of the desired compound.

b) Title compound of the example

Subjecting the compound obtained in section a) to the same alkylation process described in a) above, but using a mixture of tetrahydrofuran and hexamethylphosphoramide as solvent and heating the mixture at reflux, a crude product was obtained, which was chromatographed on silica gel (hexanedichloromethane mixtures of increasing polarity) to afford the title compound of the example (46% overall yield from the compound of ref. example 100).

$^1$H-NMR (80 MHz, DMSO-d$_6$) δ (TMS): 1.00 (t, J=7.2 Hz, 3H, CH$_3$), 1.28 (s, 6H, 2CH$_3$), 2.27 (s, 3H, CH$_3$), 3.95 (q, J=7.2 Hz, 2H, CH$_2$), 4.37 (s, 1H, CH), 7.0–7.4 (m, 9H, Ar).

REFERENCE EXAMPLE 102

Ethyl 3-(4-bromomethylphenyl)-2,2-dimethyl-3-phenylpropanoate

Following a similar procedure to that described in reference example 2, but starting from the compound obtained in reference example 101, the title compound of the example was obtained.

$^1$H-NMR (80 MHz, CDCl$_3$) δ (TMS): 1.01 (t, J=7 Hz, 3H, CH$_3$), 1.28 (s, 6H, 2CH$_3$), 3.96 (q, J=7 Hz, 2H, CH$_2$), 4.43 (m, 3H, CH$_2$+CH), 7.27 (m, 9H, Ar).

REFERENCE EXAMPLE 103

Ethyl 3-phenyl-2-isopropyl-3-(4-methylphenyl)propanoate

Following a similar procedure to that described in reference example 101b, but alkylating the compound obtained in reference example 100 and using isopropyl iodide instead of methyl iodide, the title compound of this example was obtained (yield: 58%).

$^1$H-NMR (80 MHz, CDCl$_3$) δ (TMS): 0.95 (d, J=6.8 Hz, 6H, 2CH$_3$), 0.95 (t, J=7.1 Hz, 0.5×3H, CH$_3$), 0.99 (t, J=7.1 Hz, 0.5×3H, CH$_3$), 1.74 (m, 1H, CH), 2.21 (s, 0.5×3H, CH$_3$), 2.25 (s, 0.5×3H, CH$_3$), 3.30 (dd, J=12 Hz, J=3.8 Hz, 1H, CH), 3.89 (q, J=7.1 Hz, 0.5×2H, CH$_2$), 3.92 (q, J=7.1 Hz, 0.5×2H, CH$_2$), 4.24 (d, J=12 Hz, 1H, CH), 6.9–7.5 (m, 9H, Ar).

REFERENCE EXAMPLE 104

Ethyl 3-(4-bromomethylphenyl)-2-isopropyl-3-phenylpropanoate

Following a similar procedure to that described in reference example 2, but starting from the compound obtained in reference example 103, the title compound of this example was obtained (yield: quantitative).

$^1$H-NMR (80 MHz, CDCl$_3$+CD$_3$OD) δ (TMS): 0.94 (d, J=6.7 Hz, 6H, 2CH$_3$), 1.07 (t, J=7 Hz, 3H, CH$_3$), 1.8 (m, 1H, CH), 3.26 (dd, J=12 Hz, J=3.6 Hz, 1H, CH), 3.90 )q, J=7 Hz, 2H, CH$_2$), 4.24 (d, J=12 Hz, 1H, CH), 4.39 (s, 0.5×2H, CH$_2$), 4.41 (s, 0.5×2H, CH$_2$), 7.25 (m, 9H, Ar).

REFERENCE EXAMPLE 105

Diethyl (4-methylphenyl)(isopropyl)methylmalonate

Magnesium turnings (0.17 g, 7.6 mmol), anhydrous diethyl ether (3.5 mL) and a iodine crystal were placed in a flask. Next, 0.8 mL (7.9 mmol) of isopropyl iodide in 7 mL of diethyl ether was added and the mixture was heated at reflux for 30 min. The resulting solution was cooled to 0° C. and was then added to a cooled solution (0° C.) of the product obtained in reference example 94 (1 g, 3.8 mmol) and CuBr (0.026 g) in benzene (5.4 mL). The resulting mixture was stirred at 0° C. for 10 min, 1N HCl was added and it was extracted with ethyl acetate. The organic phase was dried and the solvent was removed to give a crude product which was chromatographed on silica gel (hexaneethyl acetate mixtures of increasing polarity), to afford the title compound of the example (yield: 89%).

$^1$H-NMR (80 MHz, CDCl$_3$) δ (TMS): 0.78 (d, J=6.4 Hz, 6H, 2CH$_3$), 0.93 (t, J=7.1 Hz, 3H, CH$_3$), 1.28 (t, J=7.1 Hz, 3H, CH$_3$), 1.94 (m, 1H, CH), 2.29 (s, 3H, CH$_3$), 3.30 (m, 1H, CH), 3.92 (d, J=11 Hz, 1H, CH), 3.87 (q, J=7.1 Hz, 2H, CH$_2$), 4.22 (q, J=7.1 Hz, 2H, CH$_2$), 7.0 (s, 4H, Ar).

REFERENCE EXAMPLE 106

Diethyl [(4-methylphenyl)(isopropyl)methyl]methylmalonate

To a suspension of 55% sodium hydride (0.19 mmol) in 14 mL of dimethylformamide, cooled with an ice bath, was added dropwise 1 g (3.4 mmol) of the compound obtained in reference example 105 dissolved in 7 mL of dimethylformamide, followed by 0.6 mL (10.2 mmol) of methyl iodide. After the addition was complete, the reaction mixture was stirred at room temperature overnight. Then, water was added and the solvent was removed. The residue was taken up in ethyl acetate and washed with brine. The organic phase was dried and the solvent was removed to yield 1.3 g of a crude product. This was chromatographed on silica gel (ethyl acetate-hexane mixtures of increasing polarity) to afford 1.0 g of the title compound of the example (yield: 95%).

$^1$H-NMR (80 MHz, CDCl$_3$) δ (TMS): 0.66 (d, J=6.4 Hz, 3H, CH$_3$), 0.99 (d, J=6.4 Hz, 3H, CH$_3$), 1.1 (t, J=7.1 Hz, 3H, CH$_3$), 1.29 (t, J=7.1 Hz, 3H, CH$_3$), 1.35 (s, 3H, CH$_3$), 2.30 (s, 3H, CH$_3$), 2.30 (m, 1H, CH), 3.28 (d, J=11 Hz, 1H, CH), 3.91 (q, J=7.1 Hz, 2H, CH$_2$), 4.23 (q, J=7.1 Hz, 2H, CH$_2$), 7.03 (s, 4H, Ar).

REFERENCE EXAMPLE 107

Diethyl [(4-bromomethylphenyl)(isopropyl)methyl]methylmalonate

Following a similar procedure to that described in reference example 2, but starting from the compound obtained in reference example 106, the title compound of this example was obtained (yield: quantitative).

$^1$H-NMR (80 MHz, CDCl$_3$) δ (TMS): 0.65 (d, J=6.4 Hz, 3H, CH$_3$), 0.99 (d, J=6.4 Hz, 3H, CH$_3$), 1.1 (t, J=7.1 Hz, 3H, CH$_3$), 1.29 (t, J=7.1 Hz, 3H, CH$_3$), 1.35 (s, 3H, CH$_3$), 2.30 (m, 1H, CH), 3.25 (d, J=11 Hz, 1H, CH), 3.90 (q, J=7.1 Hz, 2H, CH$_2$), 4.23 (q, J=7.1 Hz, 2H, CH$_2$), 4.45 (s, 2H, CH$_2$), 7.0–7.2 (m, 4H, Ar).

EXAMPLE 1

3-[[4-(2-Carboxy-1-phenylvinyl)phenyl]methyl]-5,7-dimethyl-2-ethyl-3H-imidazo[4,5-b]pyridine To a solution of 9.4 g (21.4 mmol) of the product obtained in reference example 3 in 470 mL of ethanol was added 17.6 g of KOH dissolved in 96 mL of water. The mixture was heated at reflux for 2 h and then allowed to cool to room temperature. Next, it was acidified with acetic acid to pH=6 and the solvent was removed. Water was added and the resulting solution was extracted with chloroform. The organic phase was dried, the solvent was removed and the residue was washed several times with toluene to afford 8.3 g of the title compound of the example as a mixture of cis and trans isomers, which were separated by chromatography on silica gel (ethyl acetate-acetic acid) (yield: 85%).

Isomer A (faster-running fraction):
mp=97°–101° C.;
$^1$H-NMR (80 MHz, CDCl$_3$) δ (TMS): 1.26 (t, J=7 Hz, 3H, CH$_3$), 2.56 (s, 6H, 2CH$_3$), 2.79 (q, J=7 Hz, 2H, CH$_2$), 5.44 (s, 2H, CH$_2$), 6.31 (s, 1H, CH=), 6.87 (s, 1H, Pry), 7.24 (m, 10H, Ar+H).

Analysis Calcd. for C$_{26}$H$_{25}$N$_3$O$_2$.CH$_3$COOH: C 71.32%, H 6.20%, N 8.91%. Found: C 70.94%, H 6.13%, N 8.86%.

Isomer B (slower-running fraction):
mp=220°–223° C.;
$^1$H-NMR (80 MHz, CDCl$_3$) δ (TMS): 1.04 (t, J=7 Hz, 3H, CH$_3$), 2.57 (s, 6H, 2CH$_3$), 2.70 (q, J=7 Hz, 2H, CH$_2$), 5.46 (s, 2H, CH$_2$), 6.38 (s, 1H, CH=), 6.89 (s, 1H, Pyr), 7.24 (m, 10H, Ar+H).

Analysis Calcd for C$_{26}$H$_{25}$N$_3$O$_2$.0.75H$_2$O: C 73.50%, H 6.24%, N 9.89%. Found: C 73.46%, H 6.04%, N 9.64%.

EXAMPLE 2

5,7-Dimethyl-2-ethyl-3-[[4-[1-phenyl-2-(tetrazol-5-yl)vinyl]phenyl]methyl]-3H-imidazo[4,5-b]pyridine Isomer A:

To a solution of 0.320 g (0.47 mmol) of isomer A obtained in reference example 8 in 2.7 mL of CH$_2$Cl$_2$ was added 4.4 mL of 85% formic acid and the mixture was stirred at room temperature for 1 h. The solvent was removed and the resulting residue was taken up in 19 mL of tetrahydrofuran. 0.63 mL of concentrated HCl was added and the resulting mixture was stirred at room temperature for 2 days. More concentrated HCl was added and the mixture was stirred at room temperature for 3 days more. The solvent was removed and the residue was partitioned between dichloromethane and water. The organic phase was washed with brine. The aqueous phase was extracted with dichloromethane and the combined organic phases were dried and concentrated to a crude product. This was chromatographed on silica gel (ethyl acetate-methanol, 5%) to give 0.210 g of the title compound of the example as a white solid, which was then recrystallized from ethyl acetate (yield: 100%).

mp=193°–195° C.;
$^1$H-NMR (80 MHz, CDCl$_3$) δ (TMS): 1.33 (t, J=7 Hz, 3H, CH$_3$), 2.59 (s, 3H, CH$_3$), 2.62 (s, 3H, CH$_3$), 2.90 (q, J=7 Hz, 2H, CH$_2$), 4.96 (broad s, 1H, NH), 5.51 (s, 2H, CH$_2$), 6.94 (s, 1H, Pyr), 7.24 (m, 10H, Ar+CH).

Analysis Calcd for C$_{26}$H$_{25}$N$_7$.H$_2$O: C 68.87%, H 5.96%, N 21.63%. Found: C 68.86%, H 5.94%, N 21.33%.

Isomer B:

Following the same procedure described above for the preparation of isomer A, but starting from isomer B obtained in reference example 8, isomer B of the title compound of the example was obtained as a white solid (yield: 85%).

mp=226° C.;
$^1$H-NMR (80 MHz, CDCl$_3$) δ (TMS): 1.31 (t, J=7 Hz, 3H, CH$_3$), 2.59 (s, 3H, CH$_3$), 2.62 (s, 3H, CH$_3$), 2.82 (q, J=7 Hz, 2H, CH$_2$), 5.51 (s, 2H, CH$_2$), 6.8–7.6 (m, 12H, Ar+CH+NH).

Analysis Calcd for C$_{26}$H$_{25}$N$_7$.0.75H$_2$O: C 69.56%, H 5.91%, N 21.85%. Found: C 69.76%, H 5.76%, N 21.23%.

EXAMPLE 3

3-[[4-[2-Cyano-1-phenyl-2-(tetrazol-5-yl)vinyl]phenyl]methyl]-5,7-dimethyl-2-ethyl-3H-imidazo[4,5-b]pyridine a) free base To a solution of 0.56 g (0.8 mmol) of the product obtained in reference example 13 in 5 mL of ethanol and 2.5 mL of methanol was added 1 mL of concentrated HCl and it was stirred at room temperature for 4 days. The resulting solution was concentrated, basified to pH=7 and extracted with chloroform. The organic phase was dried and the solvent was removed to give a crude product that was chromatographed on silica gel (ethyl acetatemethanol, 4%) to afford 0.140 g of the title compound of the example as a mixture of isomers (yield: 39%).

$^1$H-NMR (80 MHz, DMSO) δ (TMS): 1.30 (t, J=7 Hz, 3H, CH$_3$), 2.60 (s, 3H, CH$_3$), 2.63 (s, 3H, CH$_3$), 2.84 (q, J=7 Hz, 2H, CH$_2$), 5.63 (m, 2H, CH$_2$), 6.8–7.9 (m, 11H, Ar+NH).

b) hydrochloride

The compound obtained in section a) was dissolved in chloroform and some drops of a solution of diethyl ether saturated with hydrochloric acid gas were added, and the resulting solution was left to stand in the refrigerator overnight. The paste thus obtained was concentrated and redissolved in hot ethyl acetate. Upon addition of some drops of ethanol and some diethyl ether, a solid precipitated. This was filtered off and dried to afford the title compound of the example as the hydrochloride (yield: 51%).

Analysis Calcd for C$_{27}$H$_{24}$N$_8$.HCl.2H$_2$O: C 60.84%, H 5.38%, N 21.02%. Found: C 60.64%, H 5.35%, N 20.47%.

EXAMPLE 4

5,7-Dimethyl-2-ethyl-3-[[4-[1-(2-pyridyl)-2-(tetrazol-5-yl)vinyl]phenyl]methyl]-3H-imidazo[4,5-b]pyridine a) free base Following a similar procedure to that described in example 3a, but starting from the compound obtained in reference example 19, the title compound of the example was obtained as a mixture of isomers (yield: 75%).

$^1$H-NMR (80 MHz, CDCl$_3$) δ (TMS): 1.33 (t, J=7 Hz, 3H, CH$_3$), 2.59 (s, 6H, 2CH$_3$), 2.84 (q, J=7 Hz, 2H, CH$_2$), 5.51 (m, 2H, CH$_2$), 6.5 (broad s, 1H, NH), 6.8–7.8 (m, 8H, Ar), 8.00 (s, 1H, CH=), 8.65 (d, J=4 Hz, 1H, Pyr).

b) dihydrochloride

Following a similar procedure to that described in example 3b, but starting from the compound obtained in example 4a, the title compound of this example was obtained as the dihydrochloride.

Analysis Calcd for $C_{25}H_{24}N_8.2HCl.2H_2O$: C 55.05%, H 5.54%, N 20.54%. Found: C 54.95%, H 5.46%, N 19.27%.

EXAMPLE 5

5,7-Dimethyl-2-ethyl-3-[[4-[2-methyl-1-phenyl-2-(tetrazol-5 -yl)vinyl]phenyl]methyl]-3H-imidazo[4,5-b]pyridine To a solution of 1.13 g (1.63 mmol) of the product obtained in reference example 25 in 11 mL of ethanol and 5.5 mL of methanol was added 2.2 mL of concentrated HCl and the mixture was stirred at room temperature overnight. The solvent was removed to afford the title compound of the example as a white solid (0.465 g, yield: 60%).

mp=256°–257° C.; $^1$H-NMR (80 MHz, CDCl$_3$) δ (TMS): 1.45 (t, J=7 Hz, 3H, CH$_3$), 2.25 (s, 0.5×3H, CH$_3$), 2.42 (s, 0.5×3H, CH$_3$), 2.54 (s, 3H, CH$_3$), 2.67 (s, 3H, CH$_3$), 3.12 (q, J=7 Hz, 2H, CH$_2$), 4.18 (s, 1H, NH), 5.55 (s, 0.5×2H, CH$_2$), 5.58 (s, 0.5×2H, CH$_2$), 6.7–7.5 (m, 10H, Ar).

Analysis Calcd for $C_{27}H_{27}N_7.HCl.0.25H_2O$: C 66.05%, H 5.81%, N 19.98%. Found: C 66.12%, H 5.75%, N 19.66%.

EXAMPLE 6

5,7-Dimethyl-2-ethyl-3-[[4-[1,2-diphenyl-2-(tetrazol-5-yl)vinyl]phenyl]methyl]-3H-imidazo[4,5-b]pyridine Isomer A:

Following a similar procedure to that described in example 3a, but starting from isomer A obtained in reference example 30, a crude product was obtained, which was purified by chromatography on silica gel (ethyl acetate-methanol-acetic acid, 89:10:1) to give the title compound of the example as the free base (yield: 20%).

$^1$H-NMR (80 MHz, CDCl$_3$) δ (TMS): 1.18 (t, J=7 Hz, 3H, CH$_3$), 2.56 (s, 6H, 2CH$_3$), 2.60 (q, J=7 Hz, 2H, CH$_2$), 4.60 (s, 1H, NH), 5.36 (s, 2H, CH$_2$), 6.7–7.5 (m, 15H, Ar).

The hydrochloride was prepared by treatment of a solution of the free base in chloroform with a solution of diethyl ether saturated with HCl gas. The resulting solution was allowed to stand in the refrigerator, concentrated and the white solid formed was filtered.

mp=250°–252° C.;

Analysis Calcd for $C_{32}H_{29}N_7.HCl.H_2O$: C 67.89%, H 5.70%, N 17.32%. Found: C 67.61%, H 5.31%, N 17.43%.

Isomer B:

To a solution of 0.39 g (0.59 mmol) of isomer B obtained in reference example 30 in 4 mL of ethanol and 2 mL of methanol was added 0.8 mL of concentrated HCl and the mixture was stirred at room temperature overnight. The solvent was removed, and the solid thus obtained was purified by recrystallization from ethanol to afford 0.155 g of the title compound of the example as the hydrochloride (yield: 48%).

mp=197°–202° C.;

$^1$H-NMR (80 MHz, CDCl$_3$) δ (TMS): 1.26 (t, J=7 Hz, 3H, CH$_3$), 2.59 (s, 6H, 2CH$_3$), 2.77 (q, J=7 Hz, 2H, CH$_2$), 5.41 (s, 2H, CH$_2$), 6.7–7.5 (m, 16H, Ar+NH).

Analysis Calcd for $C_{32}H_{29}N_7.HCl$: C 70.13%, H 5.52%, N 17.89%. Found: C 70.47%, H 6.02%, N 17.66%.

EXAMPLE 7

5,7-Dimethyl-3-[[4-[2-ethoxycarbonyl-1-phenyl-2-(tetrazol-5-il)vinyl]phenyl]methyl]-2-ethyl-3H-imidazo[4,5-b]pyridine Following a similar procedure to that described in reference example 5, but starting from the compound obtained in reference example 33, the title compound of the example was obtained as a mixture of isomers (yield: 23%).

mp=127°–131° C.;

$^1$H-NMR (80 MHz, CDCl$_3$) δ (TMS): 0.90 (t, J=7.5 Hz, 3H, CH$_3$), 1.15 (t, J=7.5 Hz, 0.5×3H, CH$_3$), 1.26 (t, J=7.5 Hz, 0.5×3H, CH$_3$), 2.50 (s, 3H, CH$_3$), 2.56 (s, 3H, CH$_3$), 2.70 (q, J=7.5 Hz, 2H, CH$_2$), 3.95 (q, J=7.5 Hz, 0.5×2H, CH$_2$), 4.00 (q, J=7.5 Hz, 0.5×2H, CH$_2$), 5.38 (s, 0.5×2H, CH$_2$), 5.44 (s, 0.5×2H, CH$_2$), 5.50 (broad signal, 1H, NH), 6.6–7.5 (m, 10H, Ar).

Analysis Calcd for $C_{29}H_{29}N_7O_2.0.5H_2O$: C 67.44%, H 5.79%, N 18.98%. Found: C 67.48%, H 5.82%, N 18.26%.

EXAMPLE 8

5,7-Dimethyl-2-ethyl-3-[[4-[2 -(tetrazol-5-yl)-1-(4-trifluoromethylphenyl)vinyl]phenyl]methyl]-3H-imidazo[4,5-b]pyridine Following a similar procedure to that described in reference example 4, but starting from the compound obtained in reference example 38, the title compound of the example was obtained as a mixture of isomers (yield: 29%).

mp=124°–129° C.;

$^1$H-NMR (80 MHz, CDCl$_3$) δ (TMS): 1.28 (t, J=7.5 Hz, 0.5×3H, CH$_3$), 1.33 (t, J=7.5 Hz, 0.5×3H, CH$_3$), 2.58 (s, 6H, 2CH$_3$), 2.83 (q, J=7.5 Hz, 0.5×2H, CH$_2$), 2.85 (q, J=7.5 Hz, 0.5×2H, CH$_2$), 4.03 (broad signal, 1H, NH), 5.47 (s, 0.5×2H, CH$_2$), 5.53 (s, 0.5×2H, CH$_2$), 6.92 (s, 1H, Pyr), 7.0–7.7 (m, 9H, Ar+CH).

Analysis Calcd for $C_{27}H_{24}F_3N_7.H_2O$: C 62.18%, H 5.02%, N 18.70%. Found: C 62.29%, H 4.90%, N 18.59%.

EXAMPLE 9

3-[[4-(2-Carboxy-1-phenylethyl)phenyl]methyl]-5,7 -dimethyl-2-ethyl-3H-imidazo[4,5-b]pyridine To a solution of 8.3 g (21.5 mmol) of the compound obtained in example 1 (mixture of isomers) in 276 mL of ethanol and 100 mL of dimethylformamide was added 2.76 g of 10% Pd/C and the mixture was hydrogenated at atmospheric pressure overnight. The resulting solution was filtered through celite, washed with ethanol and the solvent was removed to afford 3 g of the title compound of the example as a white solid (yield: 37%).

mp=208°–209° C.;

$^1$H-NMR (80 MHz, CD$_3$OD) δ (TMS): 1.19 (t, J=7.5 Hz, 3H, CH$_3$), 2.55 (s, 3H, CH$_3$), 2.58 (s, 3H, CH$_3$), 2.80 (q, J=7.5 Hz, 2H, CH$_2$), 3.00 (d, J=8 Hz, 2H, CH$_2$), 4.56 (t, J=8 Hz, 1H, CH), 4.76 (H$_2$O+COOH), 5.48 (s, 2H, CH$_2$), 6.9–7.4 (m, 10H, Ar).

Analysis Calcd for $C_{26}H_{27}N_3O_2$: C 75.52%, H 6.58%, N 10.16%. Found: C 75.33%, H 6.61%, N 10.07%.

EXAMPLE 10

5,7-Dimethyl-2-ethyl-3-[[4-[1-phenyl-2-(tetrazol-5-yl)ethyl]phenyl]methyl]-3H-imidazo[4,5-b]pyridine Following a similar procedure to that described in reference example 5, but starting from the compound obtained in reference example 41, the title compound of the example was obtained as a white solid (yield: 68%). 0.5×2H, CH$_2$), 4.10 (q, J=7.5 Hz, mp=94°104° C. $^1$H-NMR (80 MHz, CDCl$_3$+CD$_3$OD) δ (TMS): 1.29 (t, J=7.5 Hz, 3H, CH$_3$), 2.64 (s, 3H, CH$_3$), 2.66 (s, 3H, CH$_3$), 3.00 (q, J=7.5 Hz, 2H, CH$_2$), 3.63 (d, J=8 Hz, 2H, CH$_2$), 4.00 (H$_2$O+NH), 4.60 (t, J=8 Hz, 1H, CH), 5.55 (s, 2H, CH$_2$), 7.0–7.4 (m, 10H, Ar).

Analysis Calcd for $C_{26}H_{27}N_7 \cdot 0.75CHCl_3$: C 59.60%, H 5.15%, N 18.19%. Found: C 59.52%, H 5.44%, N 18.23%.

EXAMPLE 11

5,7-Dimethyl-2-ethyl-3-[[4-[2-(tetrazol-5-yl)-1 -(4-trifluoromethylphenyl)ethyl]phenyl]methyl]-3H-imidazo[4,5-b]pyridine Following a similar procedure to that described in reference example 5, but starting from the compound obtained in reference example 42, the title compound of the example was obtained as a white solid (yield: 40%).

mp=114°–118° C.; 1H-NMR (80 MHz, CDCl$_3$) δ (TMS): 1.14 (t, J=7.5 Hz, 3H, CH$_3$), 2.60 (s, 6H, 2CH$_3$), 2.85 (q, J=7.5 Hz, 2H, CH$_2$), 3.66 (d, J=8 H, 2H, CH$_2$), 4.79 (t, J=8 Hz, 1H, CH), 5.46 (s, 2H, CH$_2$), 6.7–7.5 (m, 10H, Ar+NH).

Analysis Calcd for $C_{27}H_{26}F_3N_7 \cdot 0.5CHCl_3$: C 58.46%, H 4.69%, N 17.35%. Found: C 58.43%, H 5.04%, N 17.01%.

EXAMPLE 12

5,7-Dimethyl-2-ethyl-3-[[3-[1-phenyl-2-(tetrazol-5-yl)vinyl]phenyl]methyl]-3H-imidazo[4,5-b]pyridine Following a similar procedure to that described in reference example 5, but using the compound obtained in reference example 45 instead of the compound obtained in reference example 4, the title compound of this example was obtained (yield: 40%).

mp=187°–195° C. $^1$H-NMR (80 MHz, CDCl$_3$+CD$_3$OD) δ (TMS): 1.32 (t, J=7 Hz, 0.5×3H, CH$_3$), 1.37 (t, J=7 Hz, 0.5×3H, CH$_3$), 2.63 (s, 3H, CH$_3$), 2.67 (s, 3H, CH$_3$), 3.03 (q, J=7 Hz, 0.5×2H, CH$_2$), 3.07 (q, J=7 Hz, 0.5×2H, CH$_2$), 4.42 (MeOH+NH), 5.60 (s, 0.5>2H, CH$_2$), 5.64 (s, 0.5×2H, CH$_2$), 6.9–7.64 (m, 11H, Ar+CH).

Analysis Calcd for $C_{26}H_{25}N_7 \cdot 0.5H_2O$: C 70.27%, H 5.90%, N 22.06%. Found: C 69.88%, H 5.75%, N 21.14%.

EXAMPLE 13

3-[[4-(2-Carboxy-2-cyano-1-phenylvinyl)phenyl]methyl]-5,7-dimethyl-2-ethyl -3H-imidazo[4,5-b]pyridine A mixture of 1.8 g (3.9 mmol) of the product obtained in reference example 33, 1.16 g (0.2 mol) of powdered potassium hydroxide, 0.414 g of 18-crown-6 and 18 mL of benzene was stirred at room temperature for 18 h. Then, 3 mL of benzene and 5 mL of 1N hydrochloric acid was added and the layers were separated. The aqueous phase was extracted with chloroform and the combined organic phases were dried over magnesium sulfate. The solvent was removed to yield a crude product which was chromatographed on silica gel (ethyl acetate-methanol-acetic acid mixtures of increasing polarity), to afford 0.5 g of the title compound of the example as a white solid (yield: 29%).

mp=192°–192.5° C.; I
$^1$-NMR (80 MHz, CDCl$_3$) δ (TMS): 1.00 (t, J=7 Hz, 0.5×3H, CH$_3$), 1.22 (t, J=7 Hz, 0.5×3H, CH$_3$), 2.57 (s, 6H, 2CH$_3$), 2.82 (q, J=7 Hz, 2H, CH$_2$), 5.48 (s, 2H, CH$_2$), 6.8–7.5 (m, 10H, Ar+CH), 10.46 (s, 1H, COOH).

Analysis Calcd for $C_{27}H_{24}N_4O_2 \cdot 1.75H_2O$: C 69.30%, H 5.88%, N 11.98%. Found: C 69.66%, H 5.50%, N 11.14%.

EXAMPLE 14

3-[[4-[2-Carboxy-1-phenyl-2-(tetrazol-5 -yl)vinyl]phenyl] methyl]-5,7-dimethyl-2-ethyl -3H-imidazo4,5-b]pyridine Following the procedure described in reference example 5, but using the compound obtained in example 13 instead of the compound obtained in reference example 4, the title compound of this example was obtained (yield: 40%).

mp=182°–183° C. $^1$H-NMR (80 MHz, CDCl$_3$+CD$_3$OD) δ (TMS): 1.26 (t, J=7 Hz, 0.5×3H, CH$_3$), 1.32 (t, J=7 Hz, 0.5×3H, CH$_3$), 2.63 (s, 3H, CH$_3$), 2.65 (s, 3H, CH$_3$), 2.95 (q, J=7 Hz, 0.5×2H, CH$_2$), 3.05 (q, J=7 Hz, 0.5×2H, CH$_2$), 3.93 (MeOH+NH+OH), 5.34 (s, 0.5×2H, CH$_2$), 5.63 (s, 0.5×2H, CH$_2$), 6.9–7.4 (m, 10H, Ar).

Analysis Calcd for $C_{27}H_{25}N_7O_2 \cdot 3H_2O \cdot 0.5AcOH$: C 59.68%, H 5.90%, N 17.40%. Found: C 60.06%, H 5.19%, N 17.69%.

EXAMPLE 15

5,7-Dimethyl-2-ethyl-3-[[4-[2-hydroxymethyl -1-phenyl-2-(tetrazol-5-yl)ethyl]phenyl]methyl]-3H-imidazo[4,5-b]pyridine Following the procedure described in reference example 5, but using each of the isomers of the compound obtained in reference example 46 instead of the compound obtained in reference example 4, the isomers A (faster-running fraction, yield: 30%) and B (slower-running fraction, yield: 25%) of the title compound of the example was obtained.

Isomer A:

mp=128°–132° C.;

$^1$H-NMR (80 MHz, CDCl$_3$) δ (TMS): 0.95 (t, J=7 Hz, 3H, CH$_3$), 2.55 (s, 6H, 2CH$_3$), 2.60 (q, J=7 Hz, 2H, CH$_2$), 3.79 (m, 2H, CH$_2$), 4.55 (m, 3H, 2CH+OH), 5.31 (s, 2H, CH$_2$), 6.8–7.3 (m, 11H, Ar+NH).

Analysis Calcd for $C_{27}H_{29}N_7O \cdot H_2O \cdot 0.75CHCl_3$: C 57.91%, H 5.52%, N 17.04%. Found: C 58.33%, H 5.85%, N 15.76%.

Isomer B:

mp=127°–131° C.;

$^1$H-NMR (80 MHz, CDCl$_3$) δ (TMS): 0.95 (t, J=7 Hz, 3H, CH$_3$), 2.55 (s, 6H, 2CH$_3$), 2.60 (q, J=7 Hz, 2H, CH$_2$), 3.79 (m, 2H, CH$_2$), 4.55 (m, 3H, 2CH+OH), 5.31 (s, 2H, CH$_2$), 6.8–7.3 (m, 11H, Ar+NH).

Analysis Calcd for $C_{27}H_{29}N_7O \cdot 0.5H_2O \cdot 0.5CHCl_3$: C 61.60%, H 5.65%, N 18.29%. Found: C 61.58%, H 6.05%, N 17.15%.

EXAMPLE 16

3-[[4-[2-Bromo-1-phenyl-2-(tetrazol-5-yl)vinyl]phenyl]methyl]-5,7-dimethyl-2-ethyl-3H-imidazo[4,5-b]pyridine Following the procedure described in reference example 5, but using the compound obtained in reference example 50 instead of the compound obtained in reference example 4, the title compound of this example was obtained (yield: 75%) as a mixture of isomers which were separated by chromatography on silica gel (ethyl acetate-acetic acid, 0.5% and then ethyl acetate-methanol-acetic acid, 95:5:0.5), to give a less polar isomer (A, 31%) and a more polar isomer (B, 27%).

Isomer A:

mp=149°–151° C.; $^1$H-NMR (80 MHz, CDCl$_3$) δ (TMS): 1.25 (t, J=7 Hz, 3H, CH$_3$), 2.55 (s, 6H, 2CH$_3$), 2.60 (q, J=7 Hz, 2H, CH$_2$), 5.31 (s, 2H, CH$_2$), 6.8–7.3 (m, 11H, Ar+NH).

Analysis Calcd for $C_{26}H_{24}BrN_7 \cdot H_2O$: C 58.65%, H 4.92%, N 18.41%. Found: C 58.97%, H 5.07%, N 18.01%.

Isomer B:

mp=241°–243° C.;

$^1$H-NMR (80 MHz, CDCl$_3$) δ (TMS): 1.25 (t, J=7 Hz, 3H, CH$_3$), 2.55 (s, 6H, 2CH$_3$), 2.60 (q, J=7 Hz, 2H, CH$_2$), 5.31 (s, 2H, CH$_2$), 6.8–7.3 (m, 11H, Ar+NH).

Analysis Calcd for $C_{26}H_{24}BrN_7 \cdot 0.25H_2O$: C 60.17%, H 4.72%, N 18.90%. Found: C 60.17%, H 4.68%, N 18.94%.

EXAMPLE 17

3-[[4-(2-Bromo-2-ethoxycarbonyl-1-phenylvinyl)phenyl]methyl]-5,7-dimethyl-2-ethyl-3H-imidazo[4,5-b]pyridine Following the procedure described in reference example 3, but starting from the compound obtained in reference example 52, the title compound of this example was obtained (yield: 60%).

$^1$H-NMR (80 MHz, CDCl$_3$) δ (TMS): 0.95 (t, J=7.5 Hz, 3H, CH$_3$), 1.30 (t, J=7.5 Hz, 3H, CH$_3$), 2.58 (s, 3H, CH$_3$), 2.62 (s, 3H, CH$_3$), 2.79 (q, J=7.5 Hz, 2H, CH$_2$) 4.01 (q, J=7.5 Hz, 2H, CH$_2$), 5.42 (s, 0.5×2H, CH$_2$), 5.44 (s, 0.5×2H, CH$_2$), 6.8–7.4 (m, 10H, Ar).

EXAMPLE 18

3-[[4-(2-Bromo-2-carboxy-1-phenylvinyl)phenyl]methyl]-5,7-dimethyl-2-ethyl-3H-imidazo[4,5-b]pyridine Following the procedure described in example 13, but starting from the compound obtained in example 17, the title compound of the example was obtained (yield: 61%).

mp=125°–129° C.;

$^1$H-NMR (80 MHz, CD$_3$OD) δ (TMS): 1.26 (t, J=7.5 Hz, 0.5×3H, CH$_3$), 1.28 (t, J=7.5 Hz, 0.5×3H, CH$_3$), 2.60 (s, 3H, CH$_3$), 2.63 (s, 3H, CH$_3$), 2.90 (q, J=7.5 Hz, 3.93 (s, COOH+MeOH), 5.49 (s, 0.5×2H, CH$_2$), 5.53 (s, 0.5×2H, CH$_2$), 6.8–7.4 (m, 10H, Ar).

Analysis Calcd for C$_{26}$H$_{24}$BrN$_3$O$_2$0.7CHCl$_3$: C 55.88%, H 4.34%, N 7.32%, Br: 13.92%. Found: C 56.26%, H 4.47%, N 7.41%, Br 13.23%.

EXAMPLE 19

3-[[4-[2-Chloro-1-phenyl-2-(tetrazol-5-yl)vinyl]phenyl]methyl]-5,7-dimethyl-2-ethyl-3H-imidazo[4,5-b]pyridine Following the procedure described in reference example 5, but starting from the compound obtained in reference example 53, the title compound of this example was obtained (yield: 31%).

mp=119°–132° C.;

$^1$-NMR (80 MHz, CDCl$_3$) δ (TMS): 1.10 (t, J=7.5 Hz, 0.5×3H, CH$_3$), 1.20 (t, J=7.5 Hz, 0.5×3H, CH$_3$), 2.45 (s, 0.5×3H, CH$_3$), 2.52 (s, 0.5×3H, CH$_3$), 2.57 (s, 0.5×3H, CH$_3$), 2.63 (s, 0.5×3H, CH$_3$), 2.78 (q, J=7.5 Hz, 2H, CH$_2$), 5.37 (s, 0.5×2H, CH$_2$), 5.46 (s, 0.5×2H, CH$_2$), 6.09 (m, 1H, NH), 6.8–7.4 (m, 10H, Ar).

Analysis Calcd for C$_{26}$H$_{24}$ClN$_7$0.5CHCl$_3$: C 60.09%, H 4.70%, N 18.50%. Found: C 59.69%, H 4.98%, N 18.61%.

EXAMPLE 20

3-[[4-(2-Chloro-2-ethoxycarbonyl-1-phenylvinyl)phenyl]methyl]-5,7-dimethyl-2-ethyl-3H-imidazo[4,5-b]pyridine Following the procedure described in reference example 53, but starting from the compound obtained in reference example 3, the title compound of this example was obtained (yield: 80%).

$^1$H-NMR (80 MHz, CDCl$_3$) δ (TMS): 1.01 (t, J=7.5 Hz, 3H, CH$_3$), 1.30 (t, J=7.5 Hz), 3H, CH$_3$), 2.57 (s, 3H, CH$_3$), 2.61 (s, 3H, CH$_3$), 2.79 (q, J=7.5 Hz, 2H, CH$_2$), 4.01 (q, J=7.5 Hz, 2H, CH$_2$), 5.44 (s, 2H, CH$_2$), 6.8–7.4 (m, 10H, Ar).

EXAMPLE 21

3-[[4-(2-Carboxy-2-chloro-1-phenylvinyl)phenyl]methyl]-5,7-dimethyl-2-ethyl-3H-imidazo[4,5-b]pyridine Following the procedure described in example 13, but starting from the compound obtained in example 20, the title compound of this example was obtained (yield: 62%).

mp=120°–125° C.;

$^1$-NMR (80 MHz, CD$_3$OD) δ (TMS): 1.26 (t, J=7.5 Hz, 3H, CH$_3$), 2.60 (s, 3H, CH$_3$), 2.63 (s, 3H, CH$_3$), 2.90 (q, J=7.5 Hz, 2H, CH$_2$), 3.98 (s, COOH+MeOH), 5.52 (s, 2H, CH$_2$), 6.8–7.4 (m, 10H, Ar).

Analysis Calcd for C$_{26}$H$_{24}$ClN$_7$.0.6CHCl$_3$: C 61.73%, H 4.79%, N 8.12%. Found: C 61.52%, H 4.95%, N 8.04%.

EXAMPLE 22

5,7-Dimethyl-2-ethyl-3-[[4-[1-(2-fluorophenyl)-2-(tetrazol-5-yl)vinyl]phenyl]methyl-3H-imidazo[4,5-b]pyridine Isomer A: Following a similar procedure to that described in reference example 5, but using isomer A obtained in reference example 70 instead of the compound obtained in reference example 4, the title compound of this example was obtained (yield: 24%).

mp=120°–125° C.;

$^1$H-NMR (80 MHz, CDCl$_3$) δ (TMS): 1.25 (t, J=7.5 Hz, 3H, CH$_3$), 2.49 (s, 3H, CH$_3$), 2.57 (s, 3H, CH$_3$), 2.77 (q, J=7.5 Hz, 2H, CH$_2$), 5.45 (s, 2H, CH$_2$), 5.98 (m, 1H, NH), 6.8–7.4 (m, 10H, Ar).

Analysis Calcd for C$_{26}$H$_{24}$FN$_7$.1.5H$_2$O: C 65.00%, H 5.62%, N 20.42%. Found: C 64.73%, H 5.30%, N 20.11%.

Isomer B: Following the same procedure described for the preparation of isomer A, but starting from isomer B obtained in reference example 70, isomer B of the title compound of this example was obtained (yield: 25%).

mp=118°–124° C.;

$^1$H-NMR (80 MHz, CDCl$_3$) δ (TMS): 1.27 (t, J=7.5 Hz, 3H, CH$_3$), 2.56 (s, 3H, CH$_3$), 2.59 (s, 3H, CH$_3$), 2.78 (q, J=7.5 Hz, 2H, CH$_2$), 4.91 (m, 1H, NH), 5.44 (s, 2, CH$_2$), 6.8–7.4 (m, 10H, Ar).

Analysis Calcd for C$_{26}$H$_{24}$FN$_7$.1.5H$_2$O: C 65.00%, H 5.62%, N 20.42%. Found: C 64.68%, H 5.32%, N 20.15%.

EXAMPLE 23

5,7-Dimethyl-2-ethyl-3-[[4-[2-(tetrazol-5-yl)-1-(2-thienyl)vinyl]phenyl]methyl]-3H-imidazo[4,5-b]pyridine Following a similar procedure to that described in reference example 5, but starting from the compound obtained in reference example 71, the title compound of the example was obtained as a mixture of isomers (yield: 40%).

$^1$H-NMR (80 MHz, CDCl$_3$) δ (TMS): 1.28 (t, J=7.5 Hz, 0.5×3H, CH$_3$), 1.32 (t, J=7.5 Hz, 0.5×3H, CH$_3$), 2.59 (s, 6H, 2CH$_3$), 2.78 (q, J=7.5 Hz, 2H, CH$_2$), 5.47 (s, 0.5×2H, CH$_2$), 5.52 (s, 0.5×2H, CH$_2$), 6.12 (m, 1H, NH), 6.6–7.4 (m, 9H, Ar).

Analysis Calcd for C$_{24}$H$_{23}$N$_7$S.0.5CHCl$_3$: C 58.70%, H 4.73%, N 19.56%, S 6.40%. Found: C 58.79%, H 4.88%, N 19.46%. S 6.04%.

EXAMPLE 24

3-[[4-[1-(2-Chlorophenyl)-2-(tetrazol-5-yl)vinyl]phenyl]methyl]-5.7-dimethyl-2-ethyl-3H-imidazo-[4,5-b]pyridine Following a similar procedure to that described in reference example 5, but starting from the compound obtained in reference example 72, the title compound of the example was obtained as a mixture of isomers (yield: 23%).

mp=28° C. $^1$H-NMR (80 MHz, CDCl$_3$) δ (TMS): 1.26 (t, J=7.5 Hz, 3H, CH$_3$), 2.54 (s, 3H, CH$_3$), 2.57 (s, 3H, CH$_3$), 2.78 (q, J=7.5 Hz, 2H, CH$_2$), 3.4 (m, 1H, NH), 5.46 (s, 2H, CH$_2$), 6.89 (s, 1H, CH), 6.8–7.4 (m 9H, Ar).

Analysis Calcd for C$_{26}$H$_{24}$ClN$_7$.H$_2$O: 63.99%, H 5.37%, N 20.09%. Found: C 64.24%, H 5.17%, N 20.25%.

EXAMPLE 25

5,7-Dimethyl-2-ethyl-3-[[4-[1-(2-fluorophenyl)-2-(tetrazol-5-yl)ethyl]phenyl]methyl]-3H-imidazo[4,5-b]pyridine Following a similar procedure to that described in reference example 5, but starting from the compound obtained in reference example 75, the title compound of this example was obtained as a white solid (yield: 44%).

mp=94°–102° C.;

$^1$H-NMR (80 MHz, CD$_3$OD) δ (TMS): 1.14 (t, J=7.5 Hz, 3H, CH$_3$), 2.44 (s, 3H, CH$_3$), 2.56 (s, 3H, CH$_3$), 2.75 (q, J=7.5 Hz, 2H, CH$_2$), 3.57 (d, J=8 Hz, 2H, CH$_2$), 3.71 (s, NH +MeOH), 4.75 (t, J=8 Hz, 1H, CH), 5.37 (s, 2H, CH$_2$), 6.8–7.4 (m, 9H, Ar).

Analysis Calcd for C$_{26}$H$_{26}$FN$_7$.0.05H$_2$O: C 67.24%, H 5.81%, N 21.12%. Found: C 67.21%, H 5.79%, N 20.11%.

EXAMPLE 26

3-[[4-[1-(2-Chlorophenyl)-2-(tetrazol-5-yl)ethyl]phenyl]methyl]-5,7-dimethyl-2-ethyl-3H-imidazo[4,5-b]pyridine Following a similar procedure to that described in reference example 5, but starting from the compound obtained in reference example 76, the title compound of this example was obtained (yield: 25%).

mp=217°–221° C. $^1$H-NMR (80 MHz, CD$_3$OD) δ (TMS): 1.23 (t, J=7.5 Hz, 3H, CH$_3$), 2.57 (s, 3H, CH$_3$), 2.61 (s, 3H, CH$_3$), 2.75 (q, J=7.5 Hz, 2H, CH$_2$), 3.57 (d, J=8 Hz, 2H, CH$_2$), 3.71 (s, NH+MeOH), 5.01 (t, J=8 Hz, 1H, CH), 5.40 (s, 2H, CH$_2$), 6.8–7.4 (m, 9H, Ar).

Analysis Calcd for C$_{26}$H$_{26}$ClN$_7$: C 66.16%, H 5.55%, N 20.77%. Found: C 65.80%,

EXAMPLE 27

5,7-Dimethyl-2-ethyl-3-[[4-[1-(4-methoxyphenyl)-2-(tetrazol-5-yl)ethyl]phenyl]methyl]-3H-imidazo[4,5-b]pyridine Following a similar procedure to that described in reference example 5, but starting from the compound obtained in reference example 77, the title compound of the example was obtained (yield: 24%).

mp=96°–99° C.;

$^1$H-NMR (80 MHz, CDCl$_3$) (TMS): 1.16 (t, J=7.5 Hz, 3H, CH$_3$), 2.50(s, 3H, CH$_3$), 2.57 (s, 3H, CH$_3$), 2.68 (q, J=7.5 Hz, 2H, CH$_2$), 3.51 (d, J=8 Hz, 2H, CH$_2$), 3.68 (s, 3H, CH$_3$), 4.40 (t, J=8 Hz, 1H, CH), 4.89 (m, 1H, NH), 5.39 (s, 2H, CH$_2$), 6.8–7.4 (m, 9H, Ar).

Analysis Calcd for C$_{27}$H$_{29}$N$_7$O.0.04CHCl$_3$: C 63.80%, H 5.71%, N 19.01%. Found: C 63.92%, H 5.77%, N 18.95%.

EXAMPLE 28

5,7-Dimethyl-2-ethyl-3-[[4-[1-(4-pyridyl)-2-(tetrazol-5-yl)ethyl]phenyl]methyl]-3H-imidazo[4,5-b]pyridine Following a similar procedure to that described in reference example 5, but starting from the compound obtained in reference example 78, the title compound of this example was obtained (yield: 43%).

$^1$H-NMR (80 MHz, CD$_3$OD) δ (TMS): 1.06 (t, J=7.5 Hz, 3H, CH$_3$), 2.58 (s, 6H, 2CH$_3$), 2.68 (q, J=7.5 Hz, 2H, CH$_2$), 3.63 (d, J=8 Hz, 2H, CH$_2$), 3.5 (H$_2$O+NH), 4.62 (t, J=8 Hz, 1H, CH), 5.40 (s, 2H, CH$_2$), 6.8–7.1 (m, 7H, Ar), 8.38 (m, 2H, Pyr).

Analysis Calcd for C$_{25}$H$_{26}$N$_8$2.5H$_2$O: C 62.11%, H 6.42%, N 23.19%. Found: C 62.19%, H 6.22%, N 23.41%.

EXAMPLE 29

5,7-Dimethyl-3-[[4-[2-ethoxycarbonyl-1-(2-fluorophenyl)vinyl]phenyl]methyl]-2-ethyl-3H-imidazo[4,5-b]pyridine Following a similar procedure to that described in reference example 3, but starting from the compound obtained in reference example 84, the title compound of this example was obtained as a mixture of isomers (yield: 63%).

$^1$H-NMR (80 MHz, CD$_3$OD) δ (TMS): 1.10 (T, J=7.5 Hz, 3, CH$_3$), 1.25 (t, J=7.5 Hz, 0.5×3H, CH$_3$), 1.30 (t, J=7.5 Hz, 0.5×3H, 2.57 (s, 3H, CH$_3$), 2.62 (s, 3H, CH$_3$), 2.77 (q, J=7.5 Hz, 2H, CH$_2$), 4.03 (q, J=7.5 Hz, 0.5×2H, CH$_2$), 4.12 (q, J=7.5 Hz, 0.5×2H, CH$_2$), 5.44 (s, 2H, CH$_2$), 6.47 (s, 1H, =CH), 6.6–7.3 (m, 9H, Ar).

The following compounds were obtained by the same procedure described for the preparation of example 29, but starting from the compounds obtained in reference examples 85–88, respectively:

EXAMPLE 30

4-[[4-[1-(2-Chlorophenyl)-2-ethoxycarbonylvinyl]phenyl]methyl]-5,7-dimethyl-2-ethyl-3H-imidazo[4,5-b]pyridine $^1$H-NMR (80 MHz, CD$_3$OD) δ (TMS): 1.07 (t, J=7.5 Hz, 3H, CH$_3$), 1.26 (t, J=7.5 Hz, 0.5×3H, CH$_3$), 1.30 (t, J=7.5 Hz, 0.5×3H, CH$_3$), 2.59 (s, 3H, CH$_3$), 2.63 (s, 3H, CH$_3$), 2.77 (q, J=7.5 Hz, 2, CH$_2$), 4.03 (q, J=7.5 Hz, 0.5×2H, CH$_2$), 4.12 (q, J=7.5 Hz, 0.5×2H, CH$_2$), 5.44 (s, 2H, CH$_2$), 6.49 (s, 1H, =CH), 6.6–7.3 (m, 9H, Ar).

EXAMPLE 31

5,7-Dimethyl-3-[[4-[2-ethoxycarbonyl-1-(4-methoxyphenyl)vinyl]phenyl]methyl]-2-ethyl-3H-imidazo[4,5-b]pyridine $^1$H-NMR (80 MHz, CD$_3$OD) δ (TMS): 1.00 (t, J=7.5 Hz, 3H, CH$_3$), 1.24 (t, J=7.5 Hz, 0.5×3H, CH$_3$), 1.31 (t, J=7.5 Hz, 0.5×3H, CH$_3$), 2.59 (s, 3H, CH$_3$), 2.63 (s, 3H, CH$_3$), 2.75 (q, J=7.5 Hz, 2, CH$_2$), 3.79 (s, 0.5×3H, CH$_3$), 3.81 (s, 0.5×3H, CH$_3$), 4.05 (q, J=7.5 Hz, 0.5×2H, CH$_2$), 4.09 (q, J=7.5 Hz, 0.5×2H, CH$_2$), 5.45 (s, 2H, CH$_2$), 5.49 (s, 0.5×2H, CH$_2$), 6.23 (s, 0.5×1H, =CH), 6.27 (s, 0.5×1H, =CH), 6.6–7.3 (m, 9H, Ar).

EXAMPLE 32

5,7-Dimethyl-3-[[4-[2-ethoxycarbonyl-1-(4-pyridyl)vinyl]phenyl]methyl]-2-ethyl-3H-imidazo[4,5-b]pyridine $^1$H-NMR (80 MHz, CD$_3$OD) δ (TMS): 1.00 (t, J=7.5 Hz, 3H, CH$_3$), 1.24 (t, J=7.5 Hz, 0.5×3H, CH$_3$), 1.31 (t, J=7.5 Hz, 0.5×3H, CH$_3$), 2.56 (s, 3H, CH$_3$), 2.61 (s, 3H, CH$_3$), 2.75 (q, J=7.5 Hz, 2H, CH$_2$), 4.05 (q, J=7.5 Hz, 2H, CH$_2$), 5.44 (s, 0.5×2H, CH$_2$), 5.49 (s, 0.5×2H, CH$_2$), 6.39 (s, 0.5×1H, =CH), 6.42 (s, 0.5×1H, =CH), 6.6–7.3 (m, 7H, Ar), 8.6 (m, 2H, Pyr).

EXAMPLE 33

5,7-Dimethyl-3-[[4-[2-(ethoxycarbonyl-1-(2,4-difluorophenyl) vinyl]phenyl]methyl]-2-ethyl-3H-imidazo[4,5-b]pyridine 2.75 (q, J=7.5 Hz, 2H, CH$_2$), 4.06 (q, J=7.5 Hz, 0.5×2H, CH$_2$), 4.10 (q, J=7.5 Hz, 0.5×2H, CH$_2$), 5.44 (s, 2H, CH$_2$), 6.44 (s, 1H, =CH), 6.6–7.3 (m, 8H, Ar).

EXAMPLE 34

5,7-Dimethyl-3-[[4-[2-ethoxycarbonyl-1-(2-fluorophenyl)ethyl]phenyl]methyl]-2-ethyl-3H-imidazo[4,5-b]pyridine Following a similar procedure to that described in example 9, but starting from the compound obtained in example 29, the title compound of this example was obtained (yield: 40%).

¹H-NMR (80 MHz, CD₃OD) δ (TMS): 1.08 (t, J=7.5 Hz, 3H, CH₃), 1.26 (t, J=7.5 Hz, 3H, CH₃), 2.57 (s, 3H, CH₃), 2.61 (s, 3H, CH₃), 2.75 (q, J=7.5 Hz, 2H, CH₂), 3.01 (d, J=8 Hz, 2H, CH₂), 4.00 (q, J=7.5 Hz, 2H, CH₂), 4.79 (t, J=8 Hz, 1H, CH), 5.39 (s, 2H, CH₂), 6.8–7.2 (m, 9H, Ar).

The following compounds were obtained by the same procedure described for the preparation of example 34, but starting from the compounds obtained in examples 30–33, respectively:

EXAMPLE 35

3-[[4-[1-(2-Chlorophenyl)-2-ethoxycarbonylethyl]phenyl]methyl]-5,7-dimethyl-2-ethyl-3H-imidazo[4,5-b]pyridine ¹H-NMR (80 MHz, CD₃OD) δ (TMS): 1.08 (t, J=7.5 Hz, 3H, CH₃), 1.29 (t, J=7.5 Hz, 3H, CH₃), 2.57 (s, 3H, CH₃), 2.61 (s, 3, CH₃), 2.75 (q, J=7.5 Hz, 2H, CH₂), 2.98 (d, J=8 Hz, 2H, CH₂), 4.02 (q, J=7.5 Hz, 2H, CH₂), 5.02 (t, J=8 Hz, 1H, CH), 5.40 (s, 2H, CH₂), 6.6–7.3 (m, 9H, Ar).

EXAMPLE 36

5,7-Dimethyl-3-[[4-[2-ethoxycarbonyl-1-(4-methoxyphenyl)ethyl]phenyl]methyl]-2-ethyl-3H-imidazo[4,5-b]pyridine ¹H-NMR (80 MHz, CD₃OD) δ (TMS): 1.09 (t, J=7.5 Hz, 3H, CH₃), 1.27 (t, J=7.5 Hz, 3H, CH₃), 2.57 (s, 3H, CH₃), 2.61 (s, 3H, CH₃), 2.75 (q, J=7.5 Hz, 2H, CH₂), 2.95 (d, J=8 Hz, 2h, CH₂), 3.75 (s, 3H, CH₃), 4.01 (q, J=7.5 Hz, 2H, CH₂), 4.45 (t, J=8 Hz, 1H, CH), 5.39 (s, 2H, CH₂), 6.6–7.3 (m, 9H, Ar).

EXAMPLE 37

5,7-Dimethyl-3-[[4-[2-ethoxycarbonyl-1-(4-pyridyl)ethyl]phenyl]methyl]-2-ethyl-3H-imidazo[4,5-b]pyridine ¹H-NMR (80 MHz, CD₃OD) δ (TMS): 1.00 (t, J=7.5 Hz, 3H, CH₃), 1.27 (t, J=7.5 Hz, 3H, CH₃), 2.57 (s, 3H, CH₃), 2.61 (s, 3H, CH₃), 2.75 (q, J=7.5 Hz, 2H, CH₂), 3.01 (d, J=8 Hz, 2H, CH₂), 4.02 (q, J=7.5 Hz, 2H, CH₂), 4.48 (t, J=8 Hz, 1H, CH), 5.40 (s, 2H, CH₂), 6.6–7.3 (m, 9H, Ar).

EXAMPLE 38

3-[[4-[1-(2,4-Difluorophenyl)-2-ethoxycarbonylethyl]phenyl]methyl]-5,7-dimethyl-2-ethyl-3H-imidazo[4,5-b]pyridine ¹H-NMR (80 MHz, CD₃OD) δ (TMS): 1.09 (t, J=7.5 Hz, 3H, CH₃), 1.27 (t, J=7.5 Hz, 3H, CH₃), 2.57 (s, 3H, CH₃), 2.60 (s, 3H, CH₃), 2.75 (q, J=7.5 Hz, 2H, CH₂), 3.01 (d, J=8 Hz, 2H, CH₂), 4.17 (q, J=7.5 Hz, 2H, CH₂), 4.74 (t, J=8 Hz, 1H, CH), 5.40 (s, 2H, CH₂), 6.6–7.3 (m, 8H, Ar).

EXAMPLE 39

3-[[4-[2-Carboxy-1-(2-fluorophenyl)ethyl phenyl]methyl]-5,7-dimethyl-2-ethyl-3H-imidazo[4,5-b]pyridine Following a similar procedure to that described in example 1, but starting from the compound obtained in example 34, the title compound of this example was obtained (yield: 64%).

mp=222° C.;

¹H-NMR (80 MHz, CD₃OD) δ (TMS): 1.27 (t, J=7.5 Hz, 3H, CH₃), 2.57 (s, 3H, CH₃), 2.60 (s, 3H, CH₃), 2.68 (q, J=7.5 Hz, 2H, CH₂), 3.05 (d, J=8 Hz, 2H, CH₂), 3.5 (HO+COOH), 4.79 (t, J=8 Hz, 1H, CH), 5.38 (s, 2H, CH₂), 6.8–7.4 (m, 9H, Ar).

Analysis Calcd for C₂₆H₂₆FN₃O₂: C 72.37%, H 6.07%, N 9.74%. Found: C 72.67%, H 6.42%, N 10.07%.

The following compounds were obtained by the same procedure described for the preparation of example 39, but starting from the compounds obtained in examples 35–38, respectively:

EXAMPLE 40

3-[[4-[2-Carboxy-1-(2-chlorophenyl)ethyl]phenyl]methyl]-5,7-dimethyl-2-ethyl-3H-imidazo[4,5-b]pyridine mp=97°–101° C.;

¹H-NMR (80 MHz, CD₃OD) δ (TMS): 1.07 (t, J=7.5 Hz, 3H, CH₃), 2.57 (s, 3H, CH₃), 2.60 (s, 3H, CH₃), 2.68 (q, J=7.5 Hz, 2H, CH₂), 3.01 (d, J=8 Hz, 2H, CH₂), 3.5 (H₂O+COOH), 5.1 (t, J=8 Hz, 1H, CH), 5.38 (s, 2H, CH₂), 6.8–7.4 (m, 9H, Ar).

Analysis Calcd for C₂₆H₂₆ClN₃O₂.0.25H₂O: C 69.03%, H 5.90%, N 9.29%. Found: C 69.19%, H 5.95%, N 8.98%.

EXAMPLE 41

3-[[4-[2-Carboxy-1-(4-methoxyphenyl)ethyl]phenyl]methyl]-5,7-dimethyl-2-ethyl-3H-imidazo(4,5-d]pyridine mp=201° C. ¹H-NMR (80 MHz, CD₃OD) δ (TMS): 1.25 (t, J=7.5 Hz, 3H, CH₃), 2.57 (s, 3H, CH₃), 2.60 (s, 3H, CH₃), 2.78 (q, J=7.5 Hz, 2H, CH₂), 2.96 (d, J=8 Hz, 2H, CH₂), 2.96 (d, J=8 Hz, 2H, CH₂), 3.75 (s, 3H, CH₃), 4.45 (t, J=8 Hz, 1H, CH), 4.76 (H₂O+COOH), 5.42 (s, 2H, CH₂), 6.6–7.3 (m, 9H, Ar).

Analysis Calcd for C₂₇H₂₉N₃O₃: C 73.28%, H 6.38%, N 9.50%. Found: C 73.34%, H 6.58%, N 9.62%.

EXAMPLE 42

3-[[4-[2-Carboxy-1-(4-pyridyl)ethyl]phenyl]methyl]-5,7-dimethyl-2-ethyl-3H-imidazo[4,5-b]pyridine ¹H-NMR (80 MHz, CD₃OD) δ (TMS): 1.26 (t, J=7.5 Hz, 3H, CH₃), 2.57 (s, 3H, CH₃), 2.60 (s, 3H, CH₃), 2.78 (q, J=7.5 Hz, 2H, CH₂), 3.00 (d, J=8 Hz, 2H, CH₂), 4.50 (t, J=8 Hz, 1H, CH), 4.76 (H₂O+COOH), 5.44 (s, 2H, CH₂), 6.9–7.4 (m, 7H, Ar), 8.4 (m, 2H, Pyr).

Analysis Calcd for C₂₅H₂₆N₄O₂.H₂O: C 69.42%, H 6.53%, N 12.95%. Found: C 69.56%, H 6.21%, N 12.33%.

EXAMPLE 43

3-[[4-[2-Carboxy-1-(2,4-difluorophenyl)ethyl] phenyl] methyl]-5,7-dimethyl -2-ethyl-3H-imidazo[4,5-b]pyridine mp=198° C. ¹H-NMR (80 MHz, CD₃OD) δ (TMS): 1.25 (t, J=7.5 Hz, 3H, CH₃), 2.57 (s, 3H, CH₃), 2.60 (s, 3H, CH₃), 2.77 (q, J=7.5 Hz, 2H, CH₂), 3.00 (d, J=8 Hz, 2H, CH₂), 4.73 (t, J=8 Hz, 1H, CH), 4.76 (H₂O+COOH), 5.42 (s, 2H, CH₂), 6.5–7.4 (m, 8H, Ar).

Analysis Calcd for C₂₆H₂₅F₂N₃O₂: C69.47%, H 5.61%, N 9.35%. Found: C 69.21%, H 5.62%, N 9.23%.

EXAMPLE 44

2-Butyl-5,7-dimethyl-3-[[4-(2-ethoxycarbonyl-1-phenylvinyl)phenyl]methyl]-3H-imidazo[4,5-d]pyridine Following a similar procedure to that described in reference example 3, but using 2-butyl-5,7-dimethylimidazo[4,5-b]pyridine (obtained according to the procedure described in EP 400974) instead of 5,7-dimethyl-2-ethylimidazo[4,5b]pyridine, the title compound of this example was obtained in 66% yield.

$^1$H-NMR (80 MHz, CDCl$_3$) δ (TMS): 0.87 (t, J=6.4 Hz, 3H, CH$_3$), 1.08 (t, J=8 Hz, 0.5×3H, CH$_3$), 1.28 (t, J=8 Hz, 0.5×3H, CH$_3$), 1.3 (m, 4H, 2CH$_2$), 2.58 (s, 3H, CH$_3$), 2.63 (s, 3H, CH$_3$), 2.73 (m, 2H, CH$_2$), 4.01 (q, J=8 Hz, 2H, CH$_2$), 5.49 (s, 0.5×2H, CH$_2$), 5.51 (s, 0.5×2H, CH$_2$), 6.33 (s, 1H, =CH), 6.7–7.2 (m, 10H, Ar).

EXAMPLE 45

2-Butyl-5,7-dimethyl-3-[[4-(2-ethoxycarbonyl-1-phenylethyl)phenyl]methyl]-3H-imidazo[4,5-b]pyridine Following a similar procedure to that described in example 9, but starting from the compound obtained in example 44, the title compound of the example was obtained in 71% yield.

$^1$H-NMR (80 MHz, CDCl$_3$) δ (TMS): 0.83 (t, J=6.4 Hz, 3H, CH$_3$), 1.08 (t, J=8 Hz, 3H, CH$_3$), 1.3 (m, 4H, 2CH$_2$), 2.57 (s, 6H, 2CH$_3$), 2.73 (m, 2H, CH$_2$), 2.99 (d, J=8 Hz, 2H, CH$_2$), 4.01 (q, J=8 Hz, 2H, CH$_2$), 4.50 (t, J=8 Hz, 1H, CH), 5.39 (s, 2H, CH$_2$), 6.7–7.2 (m, 10H, Ar).

EXAMPLE 46

2-Butyl-3-[[4-(2-carboxy-1-phenylethyl)phenyl]methyl]-5,7-dimethyl-3H-imidazo[4,5-b]pyridine Following a similar procedure to that described in example 1, but starting from the compound obtained in example 45, the title compound of the example was obtained (yield: 96%).

mp=183° C.;

$^1$H-NMR (80 MHz, CDCl$_3$) δ (TMS): 0.72 (t, J=6.4 Hz, 3H, CH$_3$), 1.3 (m, 4H, 2CH$_2$), 2.52 (s, 3H, CH$_3$), 2.54 (s, 3H, CH$_3$), 2.69 (m, 2H, CH$_2$), 3.01 (d, J=8 Hz, 2H, CH$_2$), 4.52 (t, J=8 Hz, 1H, CH), 5.36 (s, 2H, CH$_2$), 6.7–7.2 (m, 11H, Ar+COOH).

Analysis Calcd for C$_{28}$H$_{31}$N$_3$O$_2$: C 76.16%, H 7.08%, N 9.52%. Found: C 76.22%, H 7.21%, N 9.55%.

EXAMPLE 47

2-Cyclopropyl-5,7-dimethyl-3-[[4-(2-ethoxycarbonyl-1-phenylvinyl)phenyl]methyl]-3H-imidazo[4,5-b]pyridine Following a similar procedure to that described in reference example 3, but using 2-cyclopropyl-5,7-dimethylimidazo[4,5-b]pyridine (obtained analogously to the procedure described in EP 400974) instead of 5,7-dimethyl-2-ethylimidazo[4,5-b]pyridine, the title compound of the example was obtained in 47% yield.

$^1$H-NMR (80 MHz, CDCl$_3$) δ (TMS): 0.9 (m, 4H, 2CH$_2$), 1.07 (t, J=8 Hz, 3H, CH$_3$), 1.7 (m, 1H, CH), 2.57 (s, 6H, 2CH$_3$), 4.07 (q, J=8 Hz, 2H, CH$_2$), 5.54 (s, 0.5×2H, CH$_2$), 5.59 (s, 0.5×2H, CH$_2$), 6.32 (s, 1H, =CH), 6.7–7.2 (m, 10H, Ar).

EXAMPLE 48

2-Cyclopropyl-5,7-dimethyl-3-[[4-(2-ethoxycarbonyl-1phenylethyl)phenyl]methyl]-3H-imidazo[4,5-b]pyridine Following a similar procedure to that described in example 9, but starting from the compound obtained in example 47, the title compound of this example was obtained (yield: 57%).

$^1$H-NMR (80 MHz, CDCl$_3$) δ (TMS): 0.9 (m, 4H, 2CH$_2$), 1.08 (t, J=8 Hz, 3H, CH$_3$), 1.7 (m, 1H, CH), 2.56 (s, 6H, 2CH$_3$), 2.99 (d, J=8 Hz, 2H, CH$_2$), 4.01 (q, J=8 Hz, 2H, CH$_2$), 4.50 (t, J=8 Hz, 1H, CH), 5.49 (s, 2H, CH$_2$), 6.7–7.2 (m, 10H, Ar).

EXAMPLE 49

3-[[4-(2-Carboxy-1-phenylethyl)phenyl]methyl]-2-cyclopropyl-5,7-dimethyl-3H-imidazo[4,5-b]pyridine Following a similar procedure to that described in example 1, but starting from the compound obtained in example 48, the title compound of this example was obtained (yield: 57%).

mp=189°–190° C. $^1$H-NMR (80 MHz, CDCl$_3$) δ (TMS): 0.9 (m, 4H, 2CH$_2$), 1.7 (m, 1H, CH), 2.47 (s, 3H, CH$_3$), 2.53 (s, 3H, CH$_3$), 3.01 (d, J=8 Hz, 2H, CH$_2$), 4.51 (t, J=8 Hz, 1H, CH), 5.46 (s, 2H, CH$_2$), 6.7–7.2 (m, 11H, Ar+COOH).

Analysis Calcd for C$_{27}$H$_{27}$N$_3$O$_2$: C 76.21%, H 6.40%, N 9.87%. Found: C 76.12%, H 6.42%, N 9.77%.

EXAMPLE 50

5,7-Dimethyl-2-ethyl-3-[[4-[2-methylthio-1-phenyl-2 -(tetrazol-5-yl)vinyl]phenyl]methyl]-3H-imidazo[4,5-b]pyridine Following a similar procedure to that described in reference example 5, but starting from the compound obtained in reference example 90, the title compound of this example was obtained (yield: 24%).

mp=116°–119° C.;

$^1$H-NMR (80 MHz, CDCl$_3$) δ (TMS): 1.03 (t, J=7.2 Hz, 0.5×3H, CH$_3$), 1.12 (t, J=7.2 Hz, 0.5×3H, CH$_3$), 1.96 (s, 0.5×3H, CH$_3$), 1.99 (s, 0.5×3H, CH$_3$), 2.39 (s, 0.5×H, CH$_3$), 2.51 (s, 0.5×3H, CH$_3$), 2.59 (s, 0.5×3H, CH$_3$), 2.61 (s, 0.5×3H, CH$_3$), 2.6 (m, H, CH$_2$), 4.88 (s, 1H, NH), 5.28 (s, 0.5×2H, CH$_2$), 5.41 (s, 0.5×2H, CH$_2$), 6.7–7.2 (m, 10H, Ar).

Analysis Calcd for C$_{27}$H$_{27}$N$_7$S.1.5H$_2$O: C 63.76%, H 5.88%, N 19.28%, S 6.30%. Found: C 63.33%, H 5.94%, N 18.85%, S 5.94%.

EXAMPLE 51

5,7-Dimethyl-2-ethyl-3-[[4-[2-methylsulfinyl-1-phenyl-2-(tetrazol-5-yl)vinyl]phenyl]methyl]-3H-imidazo[4,5-b]pyridine To a solution of 0.43 g (0.9 mmol) of the compound obtained in example 50 in 1.5 mL of dichloromethane, cooled to −78° C., was carefully added a solution of 0.27 g (0.81 mmol) of metachloroperbenzoic acid in 1.2 mL of dichloromethane. The cooling bath was removed, the reaction mixture was allowed to warm up to room temperature and was then heated at 30° C. for 90 min. Finally, it was allowed to cool to room temperature, water was added and it was extracted with dichloromethane. The organic phase was dried and the solvent was removed to afford a crude product that was chromatographed on silica gel (ethyl acetate-methanol-acetic acid mixtures of increasing polarity), to give the title compound of the example (yield: 37%).

mp=141°–144° C.;

$^1$H-NMR (80 MHz, CDCl$_3$) δ (TMS): 1.12 (t, J=7.2 Hz, 0.5×3H, CH$_3$), 1.23 (t, J=7.2 Hz, 0.5×3H, CH$_3$), 2.47 (s, 3H, CH$_3$), 2.51 (s, 3H, CH$_3$), 2.57 (s, 3H, CH$_3$), 2.75 (q, J=7.2 Hz, 2H, CH$_2$), 4.19 (s, 1H, NH+MeOH), 5.33 (s, 0.5×2H, CH$_2$), 5.48 (s, 0.5×2H, CH$_2$), 6.7–7.2 (m, 10H, Ar).

Analysis Calcd for C$_{27}$H$_{27}$N$_7$OS.0.5CHCl$_3$: C 59.27%, H 4.98%, N 17.59%, S 5.75%. Found: C 59.35%, H 5.09%, N 17.26%, S 5.42%.

EXAMPLE 52

5,7-Dimethyl-3-[[4-[2,2-bis(ethoxycarbonyl)-1-phenyl vinyl]phenyl]methyl]-2-ethyl-3H-imidazo[4,5-b]pyridine Following a similar procedure to that described in reference example 3, but starting from the compound obtained in reference example 92, the title compound of this example was obtained (yield: 34%).

$^1$H-NMR (80 MHz, CDCl$_3$) δ (TMS): 0.98 (t, J=7.2 Hz, 3H, CH$_3$), 1.25 (t, J=7.2 Hz, 6H, 2CH$_3$), 2.55 (s, 3H, CH$_3$), 2.63 (s, 3H, CH$_3$), 2.72 (q, J=7.2 Hz, 2H, CH$_2$), 3.97 (q, J=7.2 Hz, 4H, 2CH$_2$), 5.37 (s, 2H, CH$_2$), 6.7–7.2 (m, 10H, Ar).

EXAMPLE 53

3-[[4-[2,2-Bis(carboxy)-1-phenyl]vinyl]phenyl]methyl]-5,7-dimethyl-2-ethyl-3H-imidazo[4,5-b]pyridine Following a similar procedure to that described in example 13, but starting from the compound obtained in example 52, the title compound of this example was obtained (yield: 70%).

mp=231° C. $^1$H-NMR (80 MHz, CD$_3$OD) δ (TMS): 1.26 (t, J=7.2 Hz, 3H, CH$_3$), 2.59 (s, 3H, CH$_3$), 2.61 (s, 3H, CH$_3$), 2.81 (m, 2H, CH$_2$), 3.65 (broad signal 2H, 2COOH+MeOH), 5.48 (s, 2H, CH$_2$), 6.4–7.4 (m, 10H, Ar).

Analysis Calcd for C$_{27}$H$_{25}$N$_3$O$_4$.0.5H$_2$O: C 69.83%, H 5.62%, N 9.07%. Found: C 70.14%, H 5.62%, N 8.89%.

EXAMPLE 54

5,7-Dimethyl-2-ethyl-3-[[4-[1-phenyl-2-(phenylaminocarbonyl)-2 -(tetrazol-5-yl)vinyl]phenyl]methyl]-3H-imidazo[4,5-b]pyridine a) 3-[[4-[2-Cyano-1-phenyl-2-(phenylaminocarbonyl)vinyl]phenyl]-methyl]-5,7-dimethyl-2-ethyl-3H-imidazo[4,5-b]pyridine To a mixture of 0.32 g (0.7 mmol) of the product obtained in example 13, 0.094 g (0.7 mmol) of 1-hydroxybenzotriazole and 0.144 g (0.7 mmol) of dicyclohexylcarbodiimide dissolved in 2.5 mL of dimethylformamide was added under a nitrogen atmosphere 0.065 g (0.7 mmol) of phenylamine and the mixture was stirred at room temperature overnight. Then, 20 mL ethyl acetate was added and the solid formed was filtered off. The organic solution was washed with saturated aqueous NaHCO$_3$ and water, dried over sodium sulfate and the solvent was removed to afford 0.420 g of a crude product. This was chromatographed on silica gel (ethyl acetate-hexane mixtures of increasing polarity) to yield 0.190 g of the desired product (yield: 53%).

$^1$H-NMR (80 MHz, CDCl$_3$) δ (TMS): 1.25 (t, J=7.2 Hz, 3H, CH$_3$), 2.59 (s, 3H, CH$_3$), 2.62 (s, 3H, CH$_3$), 2.76 (m, 2H, CH$_2$), 5.40 (s, 0.5×2H, CH$_2$), 5.43 (s, 0.5×2H, CH$_2$), 6.4–7.4 (m, 16H, Ar).

b) Title compound of the example

Following a similar procedure to that described in reference example 5, but starting from the compound obtained in section a), the title compound of this example was obtained (yield: 74%).

mp=172°–176° C.;

$^1$H-NMR (80 MHz, CD$_3$OD) δ (TMS): 1.26 (t, J=7.2 Hz, 3H, CH$_3$), 2.59 (s, 3H, CH$_3$), 2.61 (s, 3H, CH$_3$), 2.76 (m, 2H, CH$_2$), 3.0 (broad signal, 2H, 2NH), 5.49 (s, 2H, CH$_2$), 6.4–7.4 (m, 15H, Ar).

Analysis Calcd for C$_{33}$H$_{30}$N$_8$O.1.5CHCl$_3$: C 57.29%, H 4.39%, N 15.26%. Found: C 56.89%, H 5.77%, N 15.20%.

EXAMPLE 55

5,7-Dimethyl-2-ethyl-3-[[4-[1-phenyl -2-(phenylsulfonylaminocarbonyl)ethyl]phenyl]methyl]-3H-imidazo[4,5-b]pyridine To a mixture of 0.3 g (0.69 mmol) of the compound obtained in example 9 in 13 mL of tetrahydrofuran was added 0.111 g (0.69 mmol) of 1,1'-carbonyldiimidazole and the mixture was heated at reflux for 3 hr. Next, it was allowed to cool and a mixture consisting of 0.133 g (0.87 mmol) of benzenesulfonamide and 1.29 mL (0.87 mmol) of DBU was added. The resulting mixture was heated at 40° C. overnight, and was then allowed to cool and concentrated. The residue was taken up in water and was acidifed with 10% NaH$_2$PO$_4$ solution (pH=5). The resulting solution was then extracted with chloroform and ethyl acetate. The combined organic phases were dried and the solvents were removed to afford a crude product. This was purified by chromatography on silica gel (chloroform-methanol, 2%), to give the title compound of the example (yield: 42%).

mp=81°–86° C.; $^1$H-NMR (80 MHz, CDCl$_3$) δ (TMS): 1.21 (t, J=7.2 Hz, 3H, CH$_3$), 2.53 (s, 3H, CH$_3$), 2.55 (s, 3H, CH$_3$), 2.59 (q, J=7.2 Hz, 2H, CH$_2$), 2.77 (d, J=7.2 Hz, 2H, CH$_2$), 3.4 (broad signal 1H, COOH), 4.37 (t, J=7.2 Hz, 1H, CH), 5.34 (s, 2H, CH$_2$), 7.0–7.2 (m, 15H, Ar).

Analysis Calcd for C$_{32}$H$_{32}$N$_4$O$_3$S.1.5H$_2$O: C 66.30%, H 6.09%, N 9.66%, S 5.53%. Found: C 66.15%, H 5.81%, N 9.90%, S 6.08%.

EXAMPLE 56

5,7-Dimethyl-2-ethyl-3-[[4-[2-(methylsulfonylaminocarbonyl) -1-phenylethyl]phenyl]methyl]-3H-imidazo[4,5-b]pyridine Following a similar procedure to that described in example 55, but using methylsulfonamide instead of benzenesulfonamide and using sodium hydride as the base instead of DBU, the title compound of this example was obtained (yield: 65%).

mp=118°–123° C.;

$^1$H-NMR (80 MHz, CDCl$_3$) δ (TMS): 1.25 (t, J=7.2 Hz, 3H, CH$_3$), 2.55 (s, 3H, CH$_3$), 2.59 (s, 3H, CH$_3$), 2.76 (q, J=7.2 Hz, 2H, CH$_2$), 2.85 (d, J=7.2 Hz, 2H, CH$_2$), 2.99 (s, 3H, CH$_3$), 3.4 (broad signal 1H, COOH), 4.51 (t, J=7.2 Hz, 1H, CH), 5.41 (s, 2H, CH$_2$), 6.87 (s, 1H, Pyr), 7.0–7.2 (m, 9H, Ar).

Analysis Calcd for C$_{27}$H$_{30}$N$_4$O$_3$S: C 66.10%, H 6.16%, N 11.42%, S 6.53%. Found: C 66.15%, H 6.18%, N 11.58%, S 6.42%.

EXAMPLE 57

5,7-Dimethyl-2-ethyl-3-[[4-[1-phenyl-3 -(trifluoromethylsulfonylamino)propyl]phenyl]methyl]-3H-imidazo[4,5-b]pyridine To a solution for 0.243 (0.61 mmol) of the compound obtained in reference example 93 in 3.4 mL of dichloromethane was added 0.17 mL (1.22 mmol) of triethylamine. The resulting mixture was cooled with an ice bath, and 0.06 mL (0.37 mmol) of trifluoromethanesulfonic anhydride was added. The reaction mixture was stirred at room temperature for 1 h and another 0.06 mL of trifluoromethanesulfonic anhydride was added. It was stirred at room temperature for 1 h more, and was then diluted with dichloromethane and washed with water. The aqueous phase was extracted with ethyl acetate and the combined organic phases were dried and concentrated. The crude product thus obtained was chromatographed on silica gel (chloroform-methanol-ammonia, 89:10:1) to give the title compound of the example (yield: 35%).

mp=64°–69° C.;

$^1$H-NMR (80 MHz, CDCl$_3$) δ (TMS): 1.27 (t, J=7.2 Hz, 3H, CH$_3$), 1.87 (s, 1H, NH), 2.35 (m, 2H, CH$_2$), 2.56 (s, 3H, CH$_3$), 2.61 (s, 3H, CH$_3$), 2.76 (q, J=7.2 Hz, 2H, CH$_2$), 3.24 (t, J=7.2 Hz, 2H, CH$_2$), 3.93 (t, J=7.2 Hz, 1H, CH), 5.40 (s, 2H, CH$_2$), 6.87 (s, 1H, Pyr), 7.0–7.5 (m, 9H, Ar).

Analysis Calcd for $C_{27}H_{29}F_3N_4O_2S.0.5Et_2O$: C 61.36%, H 5.59%, N 9.86%, S 5.64%. Found: C 61.75%, H 5.72%, N 10.08%, S 5.05%.

EXAMPLE 58

3-[[4-(2-Bromo-2-carboxy-1-phenylethyl)phenyl]methyl]-5,7-dimethyl-2-ethyl-3H-imidazo[4,5-b]pyridine To a mixture of 0.3 g (0.72 mmol) of the compound obtained in example 9 and 0.028 g (0.92 mmol) of red phosphorous, cooled with an ice bath, was added 0.14 mL (2.7 mmol) of $Br_2$ and the mixture was heated at 90° C. for 5 h. 5 mL of water was added and it was extracted with ethyl acetate. The aqueous phase was reextracted with ethyl acetate and the combined organic phases were dried and concentrated. The crude product thus obtained was chromatographed on silica gel (chloroform-methanol, 2%) to give the title compound of the example (yield: 56%).

mp=117°–126° C.;

$^1$H-NMR (80 MHz, $CD_3OD$) δ (TMS): 1.26 (m, 3H, $CH_3$), 2.63 (s, 0.5×3H, $CH_3$), 2.73 (s, 0.5×3H, $CH_3$), 2.76 (s, 0.5×3H, $CH_3$), 2.84 (s, 0.5×3H, $CH_3$), 2.96 (m, 2H, $CH_2$), 3.8 (m, 1H, COOH+MeOH), 4.54 (d, J=11 Hz, 1H, CH), 4.85 (dd, J=11 Hz, 1H, CH), 5.46 (s, 0.5×2H, $CH_2$), 5.46 (s, 0.5×2H, $CH_2$), 7.0–7.5 (m, 10H, Ar).

Analysis Calcd for $C_{26}H_{26}BrN_3O_2.02CHCl_3$: C 46.00%, H 3.86%, N 5.75%. Found: C 45.97%, H 3.87%, N 6.02%.

EXAMPLE 59

5,7-Dimethyl-3-[[4-[2,2-bis(ethoxycarbonyl)-1-phenylethyl]phenyl]methyl]-2-ethyl-3H-imidazo[4,5-b]pyridine Magnesium turnings (1.4 g, 59.6 mmol), anhydrous diethyl ether (28 mL) and a iodine crystal were placed in a flask. Next, 6.56 mL (62 mmol) of bromobenzene in 56 mL of diethyl ether was added and the mixture was heated at reflux for 30 min. The resulting solution was cooled to 0° C. and was then added to a cooled solution (0° C.) of the product obtained in reference example 96 (13 g, 29.8 mmol) and CuBr (0.21 g) in benzene (42.5 mL). The resulting mixture was stirred at 0° C. for 10 min, 1N HCl was added and it was extracted with ethyl acetate. The organic phase was dried and the solvent was removed to give a crude product which was chromatographed on silica gel (hexane-ethyl acetate mixtures of increasing polarity), to afford the title compound of the example (yield: 85%).

$^1$H-NMR (80 MHz, $CDCl_3$) δ (TMS): 0.98 (t, J=7.2 Hz, 3H, $CH_3$), 1.25 (t, J=7.2 Hz, 6H, 2$CH_3$), 2.55 (s, 3H, $CH_3$), 2.63 (s, 3H, $CH_3$), 2.72 (q, J=7.2 Hz, 2H, $CH_2$), 3.97 (q, J=7.2 Hz, 4H, 2$CH_2$), 4.24 (d, J=11 Hz, 1H, CH), 4.69 (d, J=11Hz, 1H, CH), 5.37 (s, 2H, $CH_2$), 6.7–7.2 (m, 10H, Ar).

EXAMPLE 60

3-[[4-[2,2-Bis(carboxy)-1-phenylethyl]phenyl]methyl]-5,7-dimethyl-2-ethyl-3H-imidazo[4,5-b]pyridine Following a similar procedure to that described in example 1, but starting from the compound obtained in example 59, the title compound of this example was obtained (yield: 60%).

mp=137°–142° C. $^1$H-NMR (80 MHz, $CD_3OD$) δ (TMS): 1.23 (t, J=7.2 Hz, 3H, $CH_3$), 2.55 (s, 3H, $CH_3$), 2.63 (s, 3H, $CH_3$), 2.96 (q, J=7.2 Hz, 2H, $CH_2$), 3.4 (m, 2H, 2COOH+MeOH), 4.24 (d, J=11 Hz, 1H, CH), 4.69 (d, J=11 Hz, 1H, CH), 5.50 (s, 2H, $CH_2$), 7.0–7.5 (m, 10H, Ar).

Analysis Calcd for $C_{27}H_{27}N_3O_4.0.75CHCl_3$: C 60.93%, H 5.11%, N 7.68%. Found: C 60.53%, H 5.59%, N 7.73%.

EXAMPLE 61

5,7-Dimethyl-3-[[4-[2,2-bis(ethoxycarbonyl)-1-(4-methylphenyl)ethyl]phenyl]methyl]-2-ethyl-3H-imidazo[4,5-b]pyridine Following a similar procedure to that described in example 59, but using 4-bromotoluene instead of bromobenzene, the title compound of this example was obtained (yield: 70%).

$^1$H-NMR (80 MHz, $CDCl_3$) δ (TMS): 0.98 (t, J=7.2 Hz, 3H, $CH_3$), 1.02 (t, J=7.2 Hz, 3H, $CH_3$), 1.25 (t, J=7.2 Hz, 3H, $CH_3$), 2.25 (s, 3H, $CH_3$), 2.55 (s, 3H, $CH_3$), 2.61 (s, 3H, $CH_3$), 2.72 (q, J=7.2 Hz, 2H, $CH_2$), 3.96 (q, J=7.2 Hz, 2H, $CH_2$), 3.98 (q, J=7.2 Hz, 2H, $CH_2$), 4.22 (d, J=11 Hz, 1H, CH), 4.68 (d, J=11 Hz, 1H, CH), 5.36 (s, 2H, $CH_2$), 6.7–7.2 (m, 9H, Ar).

EXAMPLE 62

3-[[4-[2,2-Bis(carboxy)-1-(4-methylphenyl)ethyl]phenyl]methyl]-5,7-dimethyl-2-ethyl-3H-imidazo[4,5-b]pyridine Following a similar procedure to that described in example 1, but starting from the compound obtained in example 61, the title compound of this example was obtained (yield: 54%).

mp=140°–141° C.;

$^1$H-NMR (80 MHz, $CD_3OD$) δ (TMS): 1.21 (t, J=7.2 Hz, 3H, $CH_3$), 2.24 (s, 3H, $CH_3$), 2.55 (s, 3H, $CH_3$), 2.59 (s, 3H, $CH_3$), 2.67 (q, J=7.2 Hz, 2H, $CH_2$), 3.84 (m, 2H, 2COOH+MeOH), 4.1 (d, J=11 Hz, 1H, CH), 4.6 (d, J=11 Hz, 1H, CH), 5.42 (s, 2H, $CH_2$), 7.0–7.5 (m, 9H, Ar).

Analysis Calcd for $C_{28}H_{29}N_3O_4.2H_2O$: C 66.27%, H 6.51%, N 8.28%. Found: C 66.63%, H 6.65%, N 7.87%.

EXAMPLE 63

5,7-Dimethyl-3-[[4-[2,2-bis(ethoxycarbonyl)-1-(3-methylphenyl)ethyl]phenyl]methyl]-2-ethyl-3H-imidazo[4,5-b]pyridine Following a similar procedure to that described in example 59, but using 3-bromotoluene instead of bromobenzene, the title compound of this example was obtained (yield: 72%).

$^1$H-NMR (80 MHz, $CDCl_3$) δ (TMS): 0.97 (t, J=7.2 Hz, 3H, $CH_3$), 0.99 (t, J=7.2 Hz, 3H, $CH_3$), 1.25 (t, J=7.2 Hz, 3H, $CH_3$), 2.25 (s, 3H, $CH_3$), 2.55 (s, 3H, $CH_3$), 2.61 (s, 3H, $CH_3$), 2.72 (q, J=7.2 Hz, 2H, $CH_2$), 3.96 (q, J=7.2 Hz, 2H, $CH_2$), 3.98 (q, J=7.2 Hz, 2H, $CH_2$), 4.23 (d, J=11 Hz, 1H, CH), 4.67 (d, J=11 Hz, 1H, CH), 5.36 (s, 2H, $CH_2$), 6.7–7.2 (m, 9H, Ar).

EXAMPLE 64

3-[[4-[2,2-Bis(carboxy)-1-(3-methylphenyl)ethyl]phenyl]methyl]-5,7-dimethyl-2-ethyl-3H-imidazo[4,5-b]pyridine Following a similar procedure to that described in example 1, but starting from the compound obtained in example 63, the title compound of this example was obtained (yield: 60%).

mp=141°14 143° C. $^1$H-NMR (80 MHz, $CD_3OD$) δ (TMS): 1.21 (t, J=7.2 Hz, 3H, $CH_3$), 2.24 (s, 3H, $CH_3$), 2.55 (s, 3H, $CH_3$), 2.59 (s, 3, $CH_3$), 2.67 (q, J=7.2 Hz, 2H, $CH_2$), 3.84 (m, 2H, 2COOH+MeOH), 4.1 (m, 1H, CH), 4.6 (m, 1h, CH), 5.39 (s, 2H, $CH_2$), 7.0–7.5 (m, 9H, Ar).

Analysis Calcd for $C_{28}H_{29}N_3O_4.2H_2O$: C 66.27%, H 6.51%, N 8.28%. Found: C 6.54%, H 6.32%, N 8.20%.

EXAMPLE 65

5,7-Dimethyl-3-[[4-[2,2-bis(ethoxycarbonyl)-1-(2-methylphenyl)ethyl]phenyl]methyl]-2-ethyl-3H-imidazo[4,5-b]pyridine Following a similar procedure to that described in example 59, but using 2-bromotoluene instead of bromobenzene, the title compound of this example was obtained (yield: 62%).

$^1$H-NMR (80 MHz, CDCl$_3$) δ (TMS): 0.97 (t, J=7.2 Hz, 3H, CH$_3$), 1.25 (t, J=7.2 Hz, 6H, 2CH$_3$), 2.33 (s, 3H, CH$_3$), 2.55 (s, 3H, CH$_3$), 2.61 (s, 3H, CH$_3$), 2.71 (q, J=7.2 Hz, 2H, CH$_2$), 3.94 (q, J=7.2 Hz, 2H, CH$_2$), 3.96 (q, J=7.2 Hz, 2H, CH$_2$), 4.26 (d, J=11 Hz, 1H, CH), 4.95 (d, J=11 Hz, 1H, CH), 5.36 (s, 2H, CH$_2$), 6.7–7.2 (m, 9H, Ar).

EXAMPLE 66

3-[[4-[2,2-Bis(carboxy)-1-(2-methylphenyl)ethyl]phenyl]methyl]-5,7-dimethyl-2-ethyl-3H-imidazo[4,5-b]pyridine Following a similar procedure to that described in example 1, but starting from the compound obtained in example 65, the title compound of this example was obtained (yield: 71%).

mp=160°–161° C. $^1$H-NMR (80 MHz, CD$_3$OD) δ (TMS): 1.25 (t, J=7.2 Hz, 3H, CH$_3$), 2.30 (s, 3H, CH$_3$), 2.55 (s, 3H, CH$_3$), 2.59 (s, 3H, CH$_3$), 2.67 (q, J=7.2 Hz, 2H, CH$_2$), 3.60 (m, 2H, 2COOH+MeOH), 4.1 (m, 1H, CH), 4.8 (m, 1H, CH), 5.39 (s, 2H, CH$_2$), 7.0–7.5 (m, 9H, Ar).

Analysis Calcd for C$_{28}$H$_{29}$N$_3$O$_4$.2H$_2$O: C 66.27%, H 6.51%, N 8.28%. Found: C 6.35%, H 6.43%, N 8.01%.

EXAMPLE 67

3-[[4-[1-Benzyl-2,2-bis(ethoxycarbonyl)ethyl]phenyl]methyl]-5,7-dimethyl -2-ethyl-3H-imidazo[4,5-b]pyridine Following a similar procedure to that described in example 59, but using benzyl bromide instead of bromobenzene, the title compound of this example was obtained (yield: 66%).

$^1$H-NMR (80 MHz, CDCl$_3$) δ (TMS): 0.91 (t, J=7.2 Hz, 3H, CH$_3$), 1.19 (t, J=7.2 Hz, 3H, CH$_3$), 1.29 (t, J=7.2 Hz, 3H, CH$_3$), 2.58 (s, 3H, CH$_3$), 2.62 (s, 3H, CH$_3$), 2.64 (q, J=7.2 Hz, 2H, CH$_2$), 2.9 (m, 3H, CH+CH$_2$), 3.63 (m, 1H, CH), 3.85 (q, J=7.2 Hz, 2H, CH$_2$), 4.24 (q, J=7.2 Hz, 2H, CH$_2$), 5.35 (s, 2H, CH$_2$), 6.7–7.2 (m, 10H, Ar)

EXAMPLE 68

3-[[4-[1- Benzyl-2,2 -bis(carboxy)ethyl]phenyl]methyl]-5,7-dimethyl-2-ethyl-3H-imidazo[4,5-b]pyridine Following a similar procedure to that described in example 1, but starting from the compound obtained in example 67, the title compound of this example was obtained (yield: 87%).

mp=127°–128° C. $^1$H-NMR (80 MHz, CD$_3$OD) δ (TMS): 1.22 (t, J=7.2 Hz, 3H, CH$_3$), 2.59 (s, 3H, CH$_3$), 2.61 (s, 3H, CH$_3$), 2.64 (q, J=7.2 Hz, 2H, CH$_2$), 3.4 (m, 1H, CH), 3.78 (m, 5H, CH, CH$_2$, 2COOH+MeOH), 5.41 (s, 2H, CH$_2$), 7.0–7.5 (m, 10H, Ar).

Analysis Calcd for C$_{28}$H$_{29}$N$_3$O$_4$.2H$_2$O: 66.27%, H 6.51%, N 8.28%. Found: C 66.28%, H 6.09%, N 8.23%.

EXAMPLE 69

3-[[4-(2-Cyano-2-ethoxycarbonyl-1-phenyl ethyl)phenyl]methyl]-5,7-dimethyl -2-ethyl-3H-imidazo[4,5-b]pyridine Following a similar procedure to that described in example 59, but starting from the compound obtained in reference example 99, the title compound of this example was obtained (yield: 74%).

$^1$H-NMR (80 MHz, CDCl$_3$) δ (TMS): 1.05 (t, J=7.2 Hz, 3H, CH$_3$), 1.26 (t, J=7.2 Hz, 3H, CH$_3$), 2.55 (s, 3H, CH$_3$), 2.60 (s, 3H, CH$_3$), 2.74 (q, J=7.2 Hz, 2H, CH$_2$), 4.1 (m, 3H, CH$_2$+CH), 4.67 (d, J=11 Hz, 1H, CH), 5.40 (s, 2H, CH$_2$), 6.85 (s, 1H, Pry), 7.0–7.5 (m, 9H, Ar).

EXAMPLE 70

3-[[4-(2-Carboxy-2-cyano-1-phenylethyl)phenyl]methyl]-5,7-dimethyl-2-ethyl-3H-imidazo[4,5-b]pyridine, hydrochloride Following a similar procedure to that described in example 1, but starting from the compound obtained in example 69, the title compound of this example was obtained (yield: 31%).

mp=123°–127° C. $^1$H-NMR (80 MHz, CD$_3$OD) δ (TMS): 1.2 (t, J=7.2 Hz, 3H, CH$_3$), 2.57 (s, 3H, CH$_3$), 2.60 (s, 3H, CH$_3$), 2.74 (q, J=7.2 Hz, 2H, CH$_2$), 4.0 (s, COOH+MeOH), 4.15 (d, J=11 Hz, 1H, CH), 4.67 (d, J=11 Hz, 1H, CH), 5.41 (s, 2H, CH$_2$), 6.85 (s, 1H, Pyr), 7.0–7.5 (m, 9H, Ar).

Analysis Calcd for C$_{27}$H$_{26}$N$_4$O$_2$.HCl.H$_2$O: C 65.68%, H 5.93%, N 11.36%. Found: C 65.41%, H 5.75%, N 10.92%.

EXAMPLE 71

5,7-Dimethyl-3-[[4-[2,2-bis(ethoxycarbonyl)-2-methyl -1-phenylethyl]phenyl]methyl]-2-ethyl-3H-imidazo[4,5-b]pyridine To a suspension of 55% sodium hydride in 103 mL of dimethylformamide, cooled with an ice bath, was added dropwise 13 g (25.3 mmol) of the compound obtained in example 59 dissolved in 51 mL of dimethylformamide, followed by 4.6 mL (75.9 mmol) of methyl iodide. After the addition was complete, the reaction mixture was stirred at room temperature overnight. Then, water was added and the solvent was removed. The residue was taken up in ethyl acetate and washed with brine. The organic phase was dried and the solvent was removed to yield 13 g of a crude product. This was chromatographed on silica gel (ethyl acetate-hexane mixtures of increasing polarity) to afford 10.2 g of the title compound of the example (yield: 76%).

$^1$H-NMR (80 MHz, CDCl$_3$) δ (TMS): 1.03 (t, J=7.2 Hz, 3H, CH$_3$), 1.24 (t, J=7.2 Hz, 6H, 2CH$_3$), 1.54 (s, 3H, CH$_3$), 2.56 (s, 3H, CH$_3$), 2.61 (s, 3H, CH$_3$), 2.74 (q, J=7.2 Hz, 2H, CH$_2$), 4.01 (q, J=7.5 Hz, 4H, 2CH$_2$), 5.05 (s, 1H, CH), 5.38 (s, 2H, CH$_2$), 6.85 (s, 1H, Pyr), 7.0–7.5 (m, 9H, Ar).

EXAMPLE 72

3-[[4-[2-Carboxy-2-methyl-1-phenylethyl]phenyl]methyl]-5,7-dimethyl-2-ethyl-3H-imidazo[4,5b]pyridine To a solution of 10.2 g (19.3 mmol) of the compound obtained in example 71 in 1.26 L of ethanol was added 46 g of KOH dissolved in 264 mL of water. The reaction mixture was heated at reflux for 4 h and was then allowed to cool to room temperature. Most of the solvent was evaporated, water was added and the resulting solution was extracted with ethyl acetate. The aqueous phase was washed with ethyl acetate, acidified to pH=4 and extracted again with ethyl acetate. The combined organic phases were dried and the solvent was removed to yield 8.7 g of the title compound of the example as a mixture of diastereoisomers, which were separated by chromatography on silica gel (ethyl acetate-hexane mixtures of increasing polarity).

Isomer A (faster-running fraction): 2.7 g, yield: 33%;

mp=218° C.; $^1$H-NMR (80 MHz, CDCl$_3$) δ (TMS): 1.11 (t, J=7.2 Hz, 3H, CH$_3$), 1.07 (d, J=6.4 Hz, 3H, CH$_3$), 2.50 (s, 3H, CH$_3$), 2.53 (s, 3H, CH$_3$), 2.69 (q, J=7.5 Hz, 2H, CH$_2$), 3.25 (m, 1H, CH), 4.05 (d, J=11 Hz, 1H, CH), 5.35 (s, 2H, CH$_2$), 6.0 (broad signal, 1H, COOH), 6.85 (s, 1H, Pyr), 7.0–7.5 (m, 9H, Ar).

Analysis Calcd for $C_{27}H_{29}N_3O_2$: C 75.85%, H 6.84%, N 9.83%. Found: C 75.79%, H 6.81%, N 9.79%.

Isomer B (slower-running fraction): 2.9 g, yield: 35%; mp=217°–221° C.;

$^1$H-NMR (80 MHz, CDCl$_3$) δ (TMS): 0.88 (t, J=7.2 Hz, 3H, CH$_3$), 1.15 (d, J=6.4 Hz, 3H, CH$_3$), 2.53 (m, 8H, 2CH$_3$+CH$_2$), 3.25 (m, 1H, CH), 4.08 (d, J=11 Hz, 1H, CH), 5.32 (s, 2H, CH$_2$), 6.0 (broad signal, 1H, COOH), 6.8–7.5 (m, 10H, Ar).

Analysis Calcd for $C_{27}H_{29}N_3O_2 \cdot 0.25H_2O$: C 75.07%, H 6.85%, N 9.72%. Found: C 75.03%, H 6.87%, N 9.86%.

The enantiomers of each of the isomers A and B were separated as follows:

(−)-Isomer A: 1 g (2.3 mmol) of isomer A was dissolved in 10 mL of hot ethyl acetate and to this solution 0.29 mL (2.3 mmol) of L(−)-α-methylbenzylamine was added. The mixture was allowed to crystallize at low temperature overnight and the solid formed was filtered. This solid was recrystallized from ethyl acetate/methanol until a constant α value was obtained in two successive recrystallizations. 0.160 g of the salt was obtained as a white solid:

$^1$H-NMR (80 MHz, CD$_3$OD) δ (TMS): 0.99 (d, J=7.2 Hz, 3H, CH$_3$), 1.17 (t, J=8 Hz, 3H, CH$_3$), 1.54 (d, J=6.4 Hz, 3H, CH$_3$), 2.55 (s, 3H, CH$_3$), 2.59 (s, 3H, CH$_3$), 2.79 (q, J=7.5 Hz, 2H, CH$_2$), 3.25 (m, 1H, CH), 4.04 (d, J=11 Hz, 1H, CH), 4.32 (q, J=8 Hz, 1H, CHN), 4.75 (3H+MeOH), 5.47 (s, 2H, CH$_2$), 6.7–7.5 (m, 15H, Ar).

The solid was dissolved in a mixture of 1N NaOH and ethyl acetate and the layers were separated. The aqueous phase was acidified with 1N HCl to pH =6 and was then extracted with ethyl acetate. The combined organic extracts were dried over anhydrous sodium sulfate and the solvent was removed to afford 0.065 g of the (−) enantiomer of isomer A as a white solid: mp=218°–219° C.;

Analysis Calcd for $C_{27}H_{29}N_3O_2 \cdot 0.5H_2O$: C 74.28%, H 6.93%, N 9.62%. Found: C 74.60%, H 7.09%, N 9.59%.

(+)-Isomer A: The mother liquor from the successive recrystallizations was concentrated. The resulting residue was dissolved in a mixture of 1N NaOH and ethyl acetate and the layers were separated. The aqueous phase was acidified with 1N HCl to pH=6 and was then extracted with ethyl acetate. The combined organic extracts were dried over anhydrous sodium sulfate and the solvent was removed to yield 0.720 g of a solid. This solid was dissolved in 20 mL of hot ethyl acetate and was then treated with 0.2 mL of D(+)-α-methylbenzylamine. The mixture was allowed to crystallize at low temperature overnight and the solid formed was filtered. This solid was recrystallized from ethyl acetate/methanol until a constant α value was obtained in two successive recrystallizations. 0.120 g of the salt was obtained as a white solid:

The salt was dissolved in a mixture of 1N NaOH and ethyl acetate and the layers were separated. The aqueous phase was acidified with 1N HCl to pH =6 and was then extracted with ethyl acetate. The combined organic extracts were dried over anhydrous sodium sulfate and the solvent was removed to afford 0.065 g of the (+) enantiomer of isomer A as a white solid:

mp=217°–218° C.;

Analysis Calcd for $C_{27}H_{29}N_3O_2 \cdot 0.05H_2O$: C 75.06%, H 6.88%, N 9.72%. Found: C 75.20%, H 7.06%, N 9.70%.

Following a similar procedure to that described for isomer A, the two enantiomers of isomer B were obtained:

(−)-Isomer B:

$[\alpha]_D^{20}=-47.0$ (5, MeOH).

mp=208°–210° C.

Analysis Calcd for $C_{27}H_{29}N_3O_2 \cdot 1.25H_2O$: C 72.06%, H 7.05%, N 9.33%. Found: C 72.26%, H 6.72%, N 9.31%.

(+)-Isomer B:

$[\alpha]_D^{20}=-48.0$ (5, MeOH).

mp=212°–214° C.;

Analysis Calcd for $C_{27}H_{29}N_3O_2 \cdot 1.25H_2O$: C 72.06%, H 7.05%, N 9.33%. Found: C 72.00%, H 6.71%, N 9.19%.

EXAMPLE 73

5,7-Dimethyl-3-[[4-[2,2-bis(ethoxycarbonyl)-2-ethyl-1-phenylethyl]phenyl]methyl]-2-ethyl-3H-imidazo[4,5-b]pyridine Following a similar procedure to that described in example 71, but using ethyl iodide instead of methyl iodide, the title compound of the example was obtained (yield: 76%).

$^1$H-NMR (80 MHz, CDCl$_3$) δ (TMS): 0.59 (t, J=6.4 Hz, 3H, CH$_3$), 0.90 (t, J=7.2 Hz, 3H, CH$_3$), 1.25 (t, J=7.2 Hz, 6H, 2CH$_3$), 2.09 (q, J=6.4 Hz, 2H, CH$_2$), 2.56 (s, 3H, CH$_3$), 2.61 (s, 3H, CH$_3$), 2.74 (q, J=7.5 Hz, 2H, CH$_2$), 3.89 (q, J=7.5 Hz, 4H, 2CH$_2$), 4.82 (s, 1H, CH), 5.35 (s, 2H, CH$_2$), 6.83 (s, 1H, CHPir), 7.0–7.5 (m, 9H, Ar).

EXAMPLE 74

3-[[4-[2-Carboxy-2-ethyl-1-phenylethyl]phenyl]methyl]-5,7-dimethyl-2-ethyl-3H-imidazo[4,5-b]pyridine Following a similar procedure to that described in example 72, but starting from the compound obtained in example 73 and extending the reaction time, the two diastereoisomers of the title compound of the example were obtained.

Isomer A (faster-running fraction, 17%):

mp=227°–229° C.;

$^1$H-NMR (80 MHz, CDCl$_3$) δ (TMS): 0.87 (t, J=7.2 Hz, 3H, CH$_3$), 1.19 (t, J=7.2 Hz, 3H, CH$_3$), 1.4 (m, 2H, CH$_2$), 2.55 (s, 6H, 2CH$_3$), 2.73 (q, J=7.5 Hz, 2H, CH$_2$), 3.10 (m, 2H, CH+COOH), 4.06 (d, J=11 Hz, 1H, CH), 5.36 (s, 2H, CH$_2$), 6.8–7.5 (m, 10H, Ar).

Analysis Calcd for $C_{28}H_{31}N_3O_2 \cdot 0.5H_2O$: C 74.68%, H 7.16%, N 9.32%. Found: C 74.43%, H 7.23%, N 9.07%.

Isomer B (slower-running fraction, 17%):

mp=251° C.;

$^1$H-NMR (80 MHz, CDCl$_3$) δ (TMS): 0.89 (t, J=7.2 Hz, 3H, CH$_3$), 1.21 (t, J=7.2 Hz, 3H, CH$_3$), 1.4 (m, 2H, CH$_2$), 2.56 (s, 3H, CH$_3$), 2.61 (s, 3H, CH$_3$), 2.73 (q, J=7.5 Hz, 2H, CH$_2$), 3.25 (m, 1H, CH), 4.06 (d, J=11 Hz, 1H, CH), 5.38 (s, 2H, CH$_2$), 6.0 (broad signal, 1H, COOH), 6.8–7.5 (m, 10H, Ar).

Analysis Calcd for $C_{28}H_{31}N_3O_2 \cdot 0.25H_2O$: C 75.39%, H 7.12%, N 9.42%. Found: C 5.15%, H 7.19%, N 9.45%.

EXAMPLE 75

3-[[4-[2-Benzyl-2,2-bis(ethoxycarbonyl)-1-phenylethyl]phenyl]methyl]-5,7-dimethyl-2-ethyl-3H-imidazo[4,5-b]pyridinedimethyl-2-ethyl-3H-imidazo[4,5-b] pyridine Following a similar procedure to that described in example 71, but using benzyl bromide instead of methyl iodide, the title compound of the example was obtained.

$^1$H-NMR (80 MHz, CDCl$_3$) δ (TMS): 0.90 (t, J=7.2 Hz, 3H, CH$_3$), 1.25 (t, J=7.2 Hz, 6H, 2CH$_3$), 2.56 (s, 3H, CH$_3$), 2.61 (s, 3H, CH$_3$), 2.74 (q, J=7.5 Hz, 2H, CH$_2$), 3.33 (s, 2H, CH$_2$), 3.89 (q, J=7.5 Hz, 4H, 2CH$_2$), 4.85 (s, 1H, CH), 5.39 (s, 2H, CH$_2$), 6.85 (s, 1H, Pyr), 7.0–7.5 (m, 14H, Ar).

EXAMPLE 76

3-[[4-(2-Benzyl-2-carboxy-1-phenylethyl)phenyl]methyl]-5,7-dimethyl-2 ethyl-3H-imidazo[4,5-b]pyridine Following a similar procedure to that described in example 72, but starting from the compound obtained in example 75 and extending the reaction time, the title compound of the example was obtained as a mixture of isomers (yield: 19%).

$^1$H-NMR (80 MHz, CDCl$_3$) δ (TMS): 0.85 (t, j=7.2 Hz, 0.5×3H, CH$_3$), 1.25 (t, J=6.4 Hz, 0.5×3H, CH$_3$), 2.53 (m, 10H, 2CH$_3$+2CH$_2$), 3.5 (m, 2H, CH+COOH), 4.18 (d, J=11 Hz, 1H, CH), 5.26 (s, 0.5×2H, CH$_2$), 5.36 (s, 0.5×2H, CH$_2$), 6.8–7.5 (m, 15, Ar).

Analysis Calcd for C$_{33}$H$_{33}$N$_3$O$_2$.0.75H$_2$O: C 76.64%, H 6.72%, N 8.12%. Found: C 76.45%, H 6.58%, N 7.73%.

EXAMPLE 77

5,7-Dimethyl-3-[[4-(2,2-dimethyl-2-ethoxycarbonyl-1-phenylethyl)phenyl]methyl]-2-ethyl-3H- imidazo[4,5-b]pyridine Following a similar procedure to that described in reference example 3, but starting from the compound obtained in reference example 102, the title compound of the example was obtained (yield: 24%).

$^1$H-NMR (80 MHz, CDCl$_3$) δ (TMS): 1.05 (t, J=8 Hz, 3H, CH$_3$), 1.24 (t, J=8 Hz, 3H, CH$_3$), 1.24 (s, 6H, 2CH$_3$), 2.57 (s, 3H, CH$_3$), 2.61 (s, 3h, CH$_3$), 2.75 (q, J=8 Hz, 2H, CH$_2$), 3.94 (q, J=8 Hz, 2, CH$_2$), 4.52 (s, 1H, CH), 5.39 (s, 2H, CH$_2$), 6.88 (s, 1H, Pyr), 6.8–7.2 (m, 9H, Ar).

EXAMPLE 78

3-[[4-(2-Carboxy-2,2-dimethyl-1-phenylethyl)phenyl]methyl]-5,7-dimethyl-2 -2-ethyl-3H-imidazo-[4,5-b]pyridine Following a similar procedure to that described in example 1, but starting from the compound obtained in example 77, the title compound of this example was obtained (yield: 37%).

mp=103°–106° C. $^1$H-NMR (80 MHz, CDCl$_3$) δ (TMS): 1.05 (t, J=8 Hz, 3H, CH$_3$), 1.27 (s, 6H, 2CH$_3$), 2.54 (s, 6H, 2CH$_3$), 2.65 (q, J=8 Hz, 2H, CH$_2$), 4.45 (s, 1H, CH), 5.53 (s, 2H, CH$_2$), 5.71 (broad signal, 1H, COOH), 6.88 (s, 1H, Pyr), 6.8–7.2 (m, 9H, Ar).

Analysis Calcd for C$_{28}$H$_{31}$N$_3$O$_2$.0.05H$_2$O: C 74.68%, H 7.16%, N 9.32%. Found: C 4.75%, H 6.94%, N 9.14%.

EXAMPLE 79

5,7-Dimethyl-3-[[4-(2-ethoxycarbonyl-2-isopropyl-1-phenylethyl)phenyl]methyl]-2-ethyl-3H-imidazo[4,5-b]pyridine Following a similar procedure to that described in reference example 3, but starting from the compound obtained in reference example 104, the title compound of this example was obtained (yield: 52%).

$^1$H-NMR (80 MHz, CDCl$_3$) δ (TMS): 0.92 (d, J=6.4 Hz, 6H, 2CH$_3$), 1.24 (t, J=7.2 Hz, 3H, CH$_3$), 1.25 (t, J=7.2 Hz, 3H, CH$_3$), 1.70 (m, 1H, CH), 2.57 (s, 3H, CH$_3$), 2.61 (s, 3H, CH$_3$), 2.69 (m, 2H, CH$_2$), 3.23 (dd, J=11 Hz, J=3.2 Hz, 1H, CH), 3.89 (q, J=7.2 Hz, 2H, CH$_2$), 4.22 (d, J=11 Hz, 1H, CH), 5.36 (s, 2H, CH$_2$), 6.88 (s, 1H, Pyr), 6.8–7.2 (m, 9H, Ar).

EXAMPLE 80

5,7-Dimethyl-2-ethyl-3-[[4-(2-methyl-2-(methylsulfonylaminocarbonyl) -1-phenylethyl)phenyl]methyl]-3H-imidazo[4,5-b]pyridine Following a similar procedure to that described in example 56, but starting from isomer A of the compound obtained in example 72, the title compound of this example was obtained (yield: 65%).

mp=117°–120° C.;

$^1$H-NMR (80 MHz, CDCl$_3$) δ (TMS): 1.13 (t, J=7.2 Hz, 3H, CH$_3$), 1.15 (d, J=6.4 Hz, 3H, CH$_3$), 2.57 (s, 6H, 2CH$_3$), 2.73 (s, 3H, CH$_3$), 3.0 (m, 3H, CH$_2$+NH), 3.3 (m, 1H, CH), 4.02 (d, J=11 Hz, 1H, CH), 5.40 (s, 2H, CH$_2$), 6.88 (s, 1H, Pyr), 6.8–7.2 (m, 9H, Ar).

Analysis Calcd for C$_{28}$H$_{32}$N$_4$O$_3$S.0.05H$_2$O: C 65.50%, H 6.43%, N 10.92%, S 6.24%. Found: C 65.77%, H 6.70%, N 10.34%, S 5.85%.

EXAMPLE 81

5,7-Dimethyl-3-[[4-[2,2-bis(ethoxycarbonyl)-1-methylethyl]phenyl]methyl]-2-ethyl-3H-imidazo-[4,5-b]pyridine Following a similar procedure to that described in example 59, but using methyl iodide instead of bromobenzene, the title compound of this example was obtained (yield: 53%).

$^1$H-NMR (80 MHz, CDCl$_3$) δ (TMS): 0.98 (t, J=7.2 Hz, 3H, CH$_3$), 1.0–1.4 (m, 9H), 2.64 (s, 3H, CH$_3$), 2.72 (s, 3H, CH$_3$), 3.11 (q, J=7.5 Hz, 2H, CH$_2$), 3.51 (m, 2H, 2CH), 3.92 (q, J=8 Hz, 2H, CH$_2$), 4.18 (q, J=8 Hz, 2H, CH$_2$), 5.57 (s, 2H, CH$_2$), 7.0–7.4 (m, 5H, Ar).

EXAMPLE 82

5,7-Dimethyl-3-[[4-[2,2-bis(ethoxycarbonyl)-1,2-dimethyl ethyl]phenyl]methyl]-2-ethyl-3H-imidazo[4,5-b]pyridine.

Following a similar procedure to that described in example 71, but starting from the compound obtained in example 81, the title compound of the example was obtained (yield: 59%).

$^1$H-NMR (80 MHz, CDCl$_3$) δ (TMS): 1.12 (t, J=7.2 Hz, 3H, CH$_3$), 1.0–1.4 (m, 12H), 2.58 (s, 3H, CH$_3$), 2.62 (s, 3H, CH$_3$), 2.76 (q, J=7.5 Hz, 2H, CH$_2$), 3.64 (q, J=7 Hz, 1H, CH), 3.92 (q, J=8 Hz, 2H, CH$_2$), 4.19 (q, J=8 Hz, 2H, CH$_2$), 5.41 (s, 2H, CH$_2$), 6.9–7.4 (m, 5H, Ar).

EXAMPLE 83

3-[[4-[2-Carboxy-1,2-dimethylethyl]phenyl]methyl]-5,7-dimethyl-2-ethyl-3H -imidazo[4,5b]pyridine Following a similar procedure to that described in example 72, but starting from the compound obtained in example 82, the title compound of the example was obtained (17%) together with the title compound of example 84 (16%).

mp=78°–81° C. $^1$H-NMR (80 MHz, CDCl$_3$) δ (TMS): 0.8–1.5 (m, 9H), 2.58 (s, 6H, 2CH$_3$), 2.70 (m, 4H, CH$_2$+2CH), 3.5–4.1 (broad signal, 1H, COOH), 5.42 (s, 2H, CH$_2$), 6.8–7.3 (m, 5H, Ar).

Analysis Calcd for C$_{22}$H$_{27}$N$_3$O$_2$.0.25H$_2$O: C 71.45%, H 7.44%, N 11.37%. Found: C 1.48%, H 7.47%, N 10.88%.

EXAMPLE 84

3-[[4-[2-Carboxy-1,2-dimethyl-2-ethoxycarbonylethyl]phenyl]methyl]-5,7-dimethyl-2-ethyl-3H-imidazo[4,5-b]pyiridine mp=77°–81° C. $^1$H-NMR (80 MHz, CDCl$_3$) δ (TMS): 0.8–1.5 (m, 12H), 2.58 (s, 6H, 2CH$_3$), 2.70 (m, 2H, CH$_2$), 3.5 (m, 1H, CH), 3.9 (m, 1H, COOH), 4.04 (q, J=8 Hz, 2H, CH$_2$), 5.42 (s, 2H, CH$_2$), 6.8–7.3 (m, 5H, Ar).

Analysis Calcd for $C_{25}H_{31}N_3O_4$: C 68.63%, H 7.14%, N 9.60%. Found: C 69.16%, H 7.27%, N 9.52%.

EXAMPLE 85

5,7-Dimethyl3-[[4-[2,2-bis(ethoxycarbonyl)-1-ethylethyl] phenyl]methyl]-2-ethyl-3H-imidazo[4,5-b]pyridine Following a similar procedure to that described in example 59, but using ethyl iodide instead of bromobenzene, the title compound of this example was obtained (yield: 88%).

$^1$H-NMR (80 MHz, CDCl$_3$) δ (TMS): 0.68 (t, J=7.2 Hz, 3H, CH$_3$), 0.95 (t, J=7.2 Hz, 3H, CH$_3$), 1.1–1.9 (m, 9H), 2.69 (s, 3H, CH$_3$), 2.80 (s, 3H, CH$_3$), 3.20 (m, 3H, CH$_3$+CH), 3.86 (q, J=8 Hz, 2H, CH$_2$), 4.23 (q, J=8 Hz, 2H, CH$_2$), 5.65 (s, 2H, CH$_2$), 7.2 (m, 5H, Ar).

EXAMPLE 86

5,7-Dimethyl-3-[[4-[2,2-bis(ethoxycarbonyl)-1-ethyl -2-methylethyl]phenyl]methyl]-2-ethyl-3H-imidazo[4,5-b]pyridine Following a similar procedure to that described in example 71, but starting from the compound obtained in example 85, the title compound of this example was obtained (yield: 61%).

$^1$H-NMR (80 MHz, CDCl$_3$) δ (TMS): 0.68 (t, J=7.2 Hz, 3H, CH$_3$), 1.0–1.4 (m, 12H), 1.78 (m, 2H, CH$_2$), 2.59 (s, 3H, CH$_3$), 2.63 (s, 3H, CH$_3$), 2.66 (q, J=7.5 Hz, 2H, CH$_2$), 3.27 (t, J=8 Hz, 1H, CH), 3.95 (q, J=8 Hz, 2H, CH$_2$), 4.18 (q, J=8 Hz, 2H, CH$_2$), 5.41 (s, 2H, CH$_2$), 6.9–7.4 (m, 5H, Ar).

EXAMPLE 87

3-[[4-[2-Carboxy-1-ethyl-2-methylethyl]phenyl]methyl]-5,7-dimethyl-2-ethyl-3H-imidazo[4,5-b]pyridine Following a similar procedure to that described in example 72, but starting from the compound obtained in example 86, the title compound of this example was obtained together with the compound of example 88.

mp=76°81° C. $^1$H-NMR (80 MHz, CDCl$_3$) δ (TMS): 0.65 (t, J=6.4 Hz, 3H, CH$_3$), 0.85 (d, J=5.6Hz, 3H, CH$_3$), 1.21 (t, J=6.4 Hz, 3H, CH$_3$), 1.6 (m, 2H, CH$_2$), 2.58 (s, 6H, 2CH$_3$), 2.50–2.9 (m, 5H, CH$_2$+2CH+COOH), 5.43 (s, 2H, CH$_2$), 6.8–7.3 (m, 5H, Ar).

Analysis Calcd for $C_{23}H_{29}N_3O_2 \cdot 0.75H_2O$: C 70.29%, H 7.82%, N 10.69%. Found: C 70.35%, H 7.69%, N 10.12%.

EXAMPLE 88

3-[[4-[2-Carboxy-2-ethoxycarbonyl-1-ethyl-2-methylethyl] phenyl]methyl]-5,7-dimethyl-2-ethyl-3H-imidazo[4,5-b]piridine mp=87°–90° C. $^1$H-RMN (80 MHz, CDCl$_3$), δ (TMS): 0.66 (t, J=6.4 Hz, 3H, CH$_3$), 0.8–1.5 (m, 9H), 1.8 (m, 2H, CH$_2$), 2.58 (s, 6H, 2CH$_3$), 2.70 (m, 2H, CH$_2$), 3.5 (m, 1H, CH), 3.9 (m, 1H, COOH), 4.10 (q, J=8 Hz, 2H, CH$_2$), 5.39 (s, 2H, CH$_2$), 6.8–7.3 (m, 5H, Ar).

Analysis calcd for $C_{26}H_{33}N_3O_4 \cdot 0.75H_2O$: C 67.17%, H 7.43%, N 9.04%. Found: C 67.34%, H 7.22%, N 8.86%.

EXAMPLE 89

6-Chloro-5,7-dimethyl-3-[[4-[2,2-bis(ethoxycarbonyl)-1 -phenylethyl]phenyl]methyl]-2-ethyl-3H-imidazo[4,5-b]piridine Following a similar procedure to that described in reference example 53, but starting from the compound obtained in example 59, the title compound of this example was obtained.

$^1$H-RMN (80 MHz, CDCl$_3$) δ (TMS): 0.99 (t, J=8 Hz, 6H, 2CH$_3$), 1.26 (t, J=8 Hz, 3H, CH$_3$), 2.67 (s, 6H, 2CH$_3$), 2.75 (q, J=8 Hz, 2H, CH$_2$), 4.24 (d, J=11 Hz, 1H, CH), 4.72 (d, J=11 Hz, 1H, CH), 5.34 (s, 2H, CH$_2$), 6.9–7.4 (m, 9H, Ar).

EXAMPLE 90

6-Chloro-3-[[4-[2,2-bis(carboxy)-1-phenylethyl]phenyl] methyl]-5,7-dimethyl -2-ethyl-3H-imidazo[4,5-b]piridine Following a similar procedure to that described in example 1, but starting from the compound obtained in example 89, the title compound of this example was obtained.

mp: 157°–158° C.; $^1$H-RMN (80 MHz, CDCl$_3$) δ (TMS): 1.21 (t, J=8 Hz, 3H, CH$_3$), 2.67 (s, 6H, 2CH$_3$), 2.75 (q, J=8 Hz, 2H, CH$_2$), 4.28 (d, J=11 Hz, 1H, CH), 4.75 (d, J=11 Hz, 1H, COOH), 5.36 (s, 2H, CH$_2$), 7/0–7.9 (m, 9H, Ar).

Analysis calcd for $C_{27}H_{26}ClN_3O_4 \cdot 0.5H_2O$: C 64.86%, H 5.44%, N 8.40%. Found: C 64.48%, H 5.21%, N 8.29%.

EXAMPLE 91

5,7-Dimethyl-3-[[4-[2,2-bis(ethoxycarbonyl)-1-isopropyl -2-methylethyl]phenyl]methyl]-2-ethyl-3H-imidazo[4,5-b]pyridine Following a similar procedure to that described in reference example 3, but starting from the compound obtained in reference example 107, the title compound of this example was obtained (yield: 62%).

$^1$H-NMR (80 MHz, CDCl$_3$) δ (TMS): 0.60 (d, J=6.4 Hz, 3H, CH$_3$), 1.1 (m, 9H, 3CH$_3$), 1.59 (s, 3H, CH$_3$), 2.1 (m, 1H, CHMe$_2$), 2.59 (s, 3H, CH$_3$), 2.63 (s, 3H, CH$_3$), 2.74 (q, J=7.1 Hz, 2H, CH$_2$), 3.28 (d, J=11 Hz, 1H, CH), 3.88 (q, J=7.1 Hz, 2H, CH$_2$), 4.21 (q, J=7.1 Hz, 2H, CH$_2$), 5.41 (s, 2H, CH$_2$), 6.89 (s, 1H, pyr), 7.04 (s, 4H, Ar).

EXAMPLE 92

3-[[4-[2-Carboxy-1-isopropyl-2-methylethyl]phenyl]methyl]-5,7-dimethyl-2-ethyl-3H-imidazo[4,5-b]pyridine Following a similar procedure to that described in example 72, but starting from the compound obtained in example 91, the title compound of this example was obtained as a mixture of diastereoisomers (yield: 62%).

mp: 84°–90° C.; $^1$H-NMR (80 MHz, CDCl$_3$) δ (TMS): 0.7–1.3 (m, 12H, 4CH$_3$), 1.9 (m, 1, CHMe$_2$), 2.58 (s, 6H, 2CH$_3$), 2.50–2.9 (m, 4H, CH$_2$3O 2CH) 4.5 (br. s., 1H, COOH), 5.38 (s, 0.5×2H, CH$_2$), 5.41 (s, 0.5×2H, CH$_2$), 6.88 (s, 1H, pyr), 7.02 (s, 4H, Ar).

Analysis Calcd for $C_{24}H_{31}N_3O_2 \cdot 0.5H_2O$: C 71.61%, H 8.01%, N 10.43%. Found: C 71.77%, H 7.85%, N 10.18%.

EXAMPLE 93

5,7-Dimethyl-3-[[4-[2-ethoxycarbonyl-1-phenyl-2-trifluoromethylethyl]phenyl]methyl]-2-ethyl-3H-imidazo[4,5-b]pyridine a) 5,7-Dimethyl-3-[[4-[2,2-bis(ethoxycarbonyl)-2-bromodifluoromethyl-1 -phenylethyl]phenyl]methyl]-2-ethyl-3H-imidazo[4,5-b]pyridine To a suspension of 0.05 g (1.16 mmol) of sodium hydride in 5 mL of tetrahydrofuran was added 0.5 g (0.97 mmol) of the compound obtained in example 59 and the mixture was stirred for 1.5 h under argon. Then, 0.09 mL (0.97 mmol) of dibromodifluoromethane was added and the mixture was stirred for 7 days at room temperature. The solvent was removed and the residue dissolved in diethyl ether and washed with water. The organic phase was dried and concentrated to give 0.37 g of the title compound which was used in the next step without further purification.

b) Title compound of the example

To a solution of the compound obtained in example 93a) in 1.5 mL of dimethylsulfoxide was added 0.112 g (1.94 mmol) of potassium fluoride and the mixture was stirred for 2 h at 170° C. under argon. The suspension thus obtained was allowed to cool, water was added and it was extracted with diethyl ether. The organic phase was dried and concentrated to give 0.4 g of a residue which was chromatographed on silica gel to yield 0.115 g of the title compound of the example as an oil (yield: 23%).

$^1$H-NMR (80 MHz, CDCl$_3$) δ (TMS): 0.92 (t, J=7.1 Hz, 3H, CH$_3$), 1.24 (t, J=7.1 Hz, 3H, CH$_3$), 2.55 (s, 3H, CH$_3$), 2.57 (s, 3H, CH$_3$), 2.65 (q, J=7.1 Hz, 2H, CH$_2$), 3.97 (q, J=7.1 Hz, 2H, CH$_2$), 4.24 (d, J=11 Hz, 1H, CH), 4.72 (d, J=11 Hz, 1H, CH), 5.36 (s, 2H, CH$_2$), 6.8–7.6 (m, 10H, Ar).

EXAMPLE 94

3-[[4-[2-Carboxy-1-phenyl-2-trifluoromethylethyl]phenyl]methyl]-5,7-dimethyl-2-ethyl-3H-imidazo[4,5-b]pyridine Following a similar procedure to that described in example 72, but starting from the compound obtained in example 93, the title compound of this example was obtained (yield: 62%).

mp: 136°138° C. $^1$H-NMR (80 MHz, CD$_3$OD+CDCl$_3$) δ (TMS): 0.92 (t, J=7.1Hz, 3H, CH$_3$), 2.55 (s, 6H, 2CH$_3$), 2.65 (q, J=7.1 Hz, 2H, CH$_2$), 4.0 (s, 1H, COOH+MeOH), 4.28 (d, J=11 Hz, 1H, CH), 4.75 (d, J=11 Hz, 1H, CH), 5.36 (s, 2H, CH$_2$), 6.8–7.6 (m, 10H, Ar).

Analysis calcd for $C_{27}H_{26}F_3N_3O_2$: C 67.35%, H 5.44%, N 8.73%. Found: C 67.34%, H 5.83%, N 8.61%.

What is claimed is:

1. A compound of formula I:

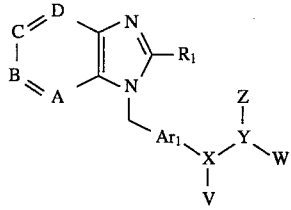

wherein:
one of A, B, C and D is N and the other are CR, wherein each R independently represents hydrogen, $C_{1-4}$ alkyl, COOH or halogen;

$R_1$ represents $C_{1-4}$ alkyl or $C_{3-7}$ cycloalkyl;

$Ar_1$ represents phenyl or pyridyl which can be optionally substituted with a group $C_{1-4}$ alkyl, $C_{1-4}$ alkoxy, halogen, nitro, amino, $C_{1-4}$ alkylamino or $C_{1-4}$ dialkylamino;

V represents $C_{1-4}$ alkyl, $C_{3-7}$ cycloalkyl, aryl, aryl-($C_{1-4}$)alkyl or a 5- or 6-membered aromatic heterocycle, in which from 1 to 3 of the ring atoms are nitrogen and/or oxygen and/or sulphur, said heterocycle being unsubstituted or having one or more substituents $R_2$;

aryl represents phenyl or phenyl substituted with one or more groups $R_2$;

$R_2$ represents $C_{1-4}$ alkyl, $C_{1-4}$ haloalkyl, $C_{1-4}$ alkoxy, $C_{1-4}$ haloalkoxy, halogen, nitro, cyano, hydroxy, amino, $C_{1-4}$ alkylamino, $C_{1-4}$ dialkylamino;

the group X—Y represents C=C or CH—CR$_3$;

$R_3$ represents hydrogen, $C_{1-4}$ alkyl or aryl-($C_{1-4}$)alkyl;

Z represents —CO$_2$R$_4$; -tetrazol-5-yl; tetrazol-5-ylmethyl; —CONH(tetrazol-5-yl); —CONHSO$_2$R$_4$; —CONHSO$_2$-Het; —CONHOR$_4$; —CONR$_4$R$_5$; —COCH$_2$COR$_4$; —COCH$_2$CO$_2$R$_4$; —CONHNHSO$_2$R$_4$; —CONHNHCONH$_2$; —CH$_2$NHSO$_2$R$_4$; —CH$_2$CO$_2$R$_4$; —CH$_2$SO$_2$NHCOR$_4$; —CH$_2$SO$_2$NHCONHR$_4$; —CH$_2$CONHSO$_2$R$_4$; —CH$_2$SO$_2$NH-Het; —CH$_2$NHCOR$_4$; —NHSO$_2$R$_4$; —NHCOR$_4$; —NHCONHSO$_2$R$_4$; —NHSO$_2$NHCOR$_4$; —NHCONR$_4$SO$_2$CH$_2$R$_4$; —SO$_3$H; —SO$_2$NHR$_4$; —SO$_2$NHCONR$_4$R$_5$; —SO$_2$NHCO$_2$R$_4$; —SO$_2$N(CO$_2$R$_4$)$_2$; —SO$_2$NHCOR$_4$; —SO$_2$NH—Het; —SO$_2$NHCO-Het; —PO(OH)$_2$; —PO(OR$_4$)$_2$; —PO(OH)(OR$_4$); 3-(trifluoromethyl)-1,2,4-triazol-5-yl; or a group of formula

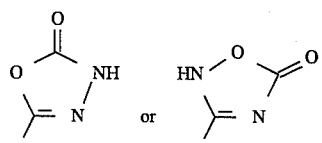

wherein Het represents a 5- or 6-membered aromatic heterocycle in which from 1 to 3 of the ring atoms are nitrogen and/or oxygen and/or sulphur and which can be optionally substituted with one or two groups chosen from hydroxy, mercapto, $C_{1-4}$ alkyl, $C_{1-4}$ alkoxy, halogen, nitro, CO$_2$H, CO$_2C_{1-4}$ alkyl, amino, $C_{1-4}$ alkylamino and $C_{1-4}$ dialkylamino; and $R_4$ and $R_5$ independently represent hydrogen, $C_{1-4}$ alkyl, aryl, aryl-($C_{1-4}$)alkyl or perfluoro-($C_{1-4}$)alkyl;

W represents hydrogen, cyano, $C_{1-4}$ alkyl, $C_{1-4}$ haloalkyl, $C_{3-7}$ cycloalkyl, aryl, aryl-($C_{1-4}$)alkyl, $C_{1-4}$ alkylsulfonyl, $C_{1-4}$ alkylsulfinyl, $C_{1-4}$ alkylthio, $C_{1-4}$ alkoxy, $C_{1-4}$ alkylcarbonyl, halogen, hydroxymethyl or $C_{1-4}$ alkoxymethyl, or W can have any of the meanings disclosed for Z;

or a salt or solvate thereof.

2. A compound according to claim 1 of formula I wherein:

$Ar_1$ represents phenyl which can be optionally substituted with a group $C_{1-4}$ alkyl, $C_{1-4}$ alkoxy, halogen, nitro, amino, $C_{1-4}$ alkylamino or $C_{1-4}$ dialkylamino;

the radical —X(V)—Y(Z)W is in the para position of the $AR_1$ ring; and

A, B, C, D, $R_1$, V, W, X, Y and Z have the previously defined meaning.

3. A compound according to claim 1 of formula I wherein:

$AR_1$ represents phenyl which can be optionally substituted with a group $C_{1-4}$ alkyl, $C_{1-4}$ alkoxy, halogen, nitro, amino, $C_{1-4}$ alkylamino or $C_{1-4}$ dialkylamino;

the radical —X(V)—Y(Z)W is in the para position of the $Ar_1$ ring;

A is N;

B, C and D are each CR; and

R, $R_1$, V, W, X, Y and Z have the previously defined meaning.

4. A compound according to claim 1 of formula I wherein:

$AR_1$ represents phenyl which can be optionally substituted with a group $C_{1-4}$ alkyl, $C_{1-4}$ alkoxy, halogen, nitro, amino, $C_{1-4}$ alkylamino or $C_{1-4}$ dialkylamino;

the radical —X(V)—Y(Z)W is in the para position of the $Ar_1$ ring;

A is N;

C is CH and B and D are each CR;

R represents hydrogen or $C_{1-4}$ alkyl; and $R_1$, V, W, X, Y and Z have the previously defined meaning.

5. A compound according to claim 1 of formula I wherein:
Ar$_1$ represents phenyl which can be optionally substituted with a group $C_{1-4}$ alkyl or halogen;
the radical —X(V)—Y(Z)W is in the para position of the Ar$_1$ ring;
A is N;
C is CH and B and D are each CR;
R represents hydrogen or $C_{1-4}$ alkyl;
V represents $C_{1-4}$ alkyl, $C_{3-7}$ cycloalkyl, aryl, or aryl-($C_{1-4}$)alkyl; and
$R_1$, W, X, Y and Z have the previously defined meaning.

6. A compound according to claim 1 of formula I wherein:
Ar$_1$ represents phenyl which can be optionally substituted with a group $C_{1-4}$ alkyl or halogen;
the radical —X(V)—Y(Z)W is in the para position of the Ar$_1$ ring;
A is N;
C is CH and B and D are each CR;
R represents hydrogen or $C_{1-4}$ alkyl;
V represents $C_{1-4}$ alkyl, $C_{3-7}$ cycloalkyl, aryl, or aryl-($C_{1-4}$)alkyl;
Z represents —CO$_2$R$_4$; -tetrazol-5-yl, —CONHSO$_2$R$_4$, —CONR$_4$R$_5$, —CH$_2$NHSO$_2$R$_4$, —SO$_2$NHR$_4$ or —SO$_2$NHCOR$_4$; and
$R_1$, $R_4$, $R_5$, W, X and Y have the previously defined meaning.

7. A compound according to claim 1 of formula I wherein:
Ar$_1$ represents phenyl which can be optionally substituted with a group $C_{1-4}$ alkyl or halogen;
the radical —X(V)—Y(Z)W is in the para position of the Ar$_1$ ring;
A is N;
C is CH and B and D are each CR;
R represents hydrogen or $C_{1-4}$ alkyl;
V represents $C_{1-4}$ alkyl, $C_{3-7}$ cycloalkyl, aryl, or aryl-($C_{1-4}$)alkyl;
Z represents —CO$_2$R$_4$; -tetrazol-5-yl, —CONHSO$_2$R$_4$, —CONR$_4$R$_5$, —CH$_2$NHSO$_2$R$_4$, —SO$_2$NHR$_4$ or —SO$_2$NHCOR$_4$;
the group X—Y represents C=C;
W represents cyano, $C_{1-4}$ alkyl, aryl, aryl-($C_{1-4}$)alkyl, $C_{1-4}$ alkylsulfonyl, $C_{1-4}$ alkylsulfinyl, $C_{1-4}$ alkylthio, or halogen, or W can have any of the meanings disclosed for Z; and
$R_1$, $R_4$ and $R_5$ have the previously defined meaning.

8. A compound according to claim 1 of formula I wherein:
Ar$_1$ represents phenyl which can be optionally substituted with a group $C_{1-4}$ alkyl or halogen;
the radical —X(V)—Y(Z)W is in the para position of the Ar$_1$ ring;
A is N;
C is CH and B and D are each CR;
R represents hydrogen or $C_{1-4}$ alkyl;
V represents $C_{1-4}$ alkyl, $C_{3-7}$ cycloalkyl, aryl, or aryl-($C_{1-4}$)alkyl;
Z represents —CO$_2$R$_4$; -tetrazol-5-yl, —CONHSO$_2$R$_4$, —CONR$_4$R$_5$, —CH$_2$NHSO$_2$R$_4$, —SO$_2$NHR$_4$ or —SO$_2$NHCOR$_4$;
the group X—Y represents CH—CH;
W represents hydrogen, $C_{1-4}$ alkyl, aryl, aryl-($C_{1-4}$)alkyl or halogen, or W can have any of the meanings disclosed for Z; and
$R_1$, $R_4$ and $R_5$ have the previously defined meaning.

9. A compound according to claim 1 of formula I wherein:
Ar$_1$ represents phenyl which can be optionally substituted with a group $C_{1-4}$ alkyl or halogen;
the radical —X(V)—Y(Z)W is in the para position of the Ar$_1$ ring;
A is N;
C is CH and B and D are each CR;
R represents hydrogen or $C_{1-4}$ alkyl;
V represents $C_{1-4}$ alkyl, $C_{3-7}$ cycloalkyl, aryl, or aryl-($C_{1-4}$)alkyl;
Z represents —CO$_2$R$_4$; -tetrazol-5-yl, —CONHSO$_2$R$_4$, —CONR$_4$R$_5$, —CH$_2$NHSO$_2$R$_4$, —SO$_2$NHR$_4$ or —SO$_2$NHCOR$_4$;
the group X—Y represents CH—CH;
W represents $C_{1-4}$ alkyl, aryl, aryl-($C_{1-4}$)alkyl or halogen, or W can have any of the meanings disclosed for Z; and
$R_1$, $R_4$ and $R_5$ have the previously defined meaning.

10. A compound according to claim 1 which is 3-[[4-[2-carboxy-2-methyl-1-phenylethyl]phenyl]methyl]-5,7-dimethyl-2-ethyl-3H-imidazo[4,5-b]pyridine as a racemate, a diastereomer mixture or in optically active form, or a salt or solvate thereof.

11. A compound according to claim 1 which is 3-[[4-[2-carboxy-2-ethyl-1phenylethyl]phenyl]methyl]-5,7-dimethyl-2-ethyl-3H-imidazo[4,5b-]pyridine as a racemate, a diastereomer mixture or in optically active form, or a salt or solvate thereof.

12. A compound according to claim 1 which is 3-[[4-[2,2-bis(carboxy)-1-phenylethyl]phenyl]methyl]-5,7-dimethyl-2-ethyl-3H-imidazo[4,5b-]pyridine as a racemate or in optically active form, or a salt or solvate thereof.

13. A pharmaceutical composition which comprises an effective amount of a compound of formula I as defined in claim 1 or a pharmaceutically acceptable salt or solvate thereof in admixture with a pharmaceutically acceptable excipient.

14. A method of inhibiting the effects of angiotensin II in a mammal which comprises administering to said mammal an angiotensin II-inhibiting amount of a compound of formula I according to claim 1 or a pharmaceutically acceptable salt or solvate thereof.

15. A method of treating or preventing hypertension in a mammal which comprises administering to said mammal a therapeutically effective amount of a compound of formula I according to claim 1 or a pharmaceutically acceptable salt or solvate thereof.

16. A method of treating or preventing congestive heart failure in a mammal which comprises administering to said mammal a therapeutically effective amount of a compound of formula I according to claim 1 or a pharmaceutically acceptable salt or solvate thereof.

17. A method of treating or preventing elevated intraocular pressure in a mammal which comprises administering to said mammal a therapeutically effective amount of a compound of formula I according to claim 1 or a pharmaceutically acceptable salt or solvate thereof.

18. A composition according to claim 13, wherein said amount is between about 0.1 and 500 mg.

19. A composition according to claim 18, wherein said amount is between about 2 and 150 mg.

20. A method according to claim 14, wherein said amount is between about 0.1 and 500 mg.

21. A method according to claim 20, wherein said amount is between about 2 and 150 mg.

* * * * *

UNITED STATES PATENT AND TRADEMARK OFFICE
CERTIFICATE OF CORRECTION

PATENT NO. : 5,554,624

DATED : September 10, 1996

INVENTOR(S) : Carmen Almansa, et al.

It is certified that error appears in the above-indentified patent and that said Letters Patent is hereby corrected as shown below:

Column 2, line 48, delete "$SO_2NHCHO$-Het" and substitute therefor --$SO_2NHCO$-Het--.

Column 4, line 37, delete "non-fluorobutyl" and substitute therefor --nonafluorobutyl--;

Column 5, line 9, delete "that" and substitute therefor --HET--;

line 16, delete "$C_1$-alkylamino" and substitute therefor --$C_{1-4}$-alkylamino--;

line 24, delete "$AR_1$" and substitute therefor --$Ar_1$--;

line 33, delete "$AR_1$" and substitute therefor --$Ar_1$--;

line 49, delete "$AR_1$" and substitute therefor --$Ar_1$--;

line 53, delete "$AR_1$" and substitute therefor --$Ar_1$--;

line 64, delete "$AR_1$" and substitute therefor --$Ar_1$--.

UNITED STATES PATENT AND TRADEMARK OFFICE
CERTIFICATE OF CORRECTION

PATENT NO. : 5,554,624
DATED : September 10, 1996
INVENTOR(S) : Carmen Almansa, et al.

Page 2 of 5

It is certified that error appears in the above-indentified patent and that said Letters Patent is hereby corrected as shown below:

Column 6, line 26, delete "$AR_1$" and substitute therefor --$Ar_1$--;

line 42, delete "$AR_1$" and substitute therefor --$Ar_1$".

Column 7, line 5, delete "CH====CH" and substitute therefor --CH═CH--.

Column 36, line 48, delete "W*50" and substitute therefor --W*=H--.

Column 37, line 52, delete "$R_3 13T$" and substitute therefor --$R_3$-T--.

Column 38, line 11, delete "$Mg_2$" and substitute therefor --$MgCl_2$--;

line 20, delete "$10^5 M$" and substitute therefor --$10^{-5} M$--.

Column 41, line 62, delete "0.1 9" and substitute therefor --0.1 g--.

Column 45, line 12, delete "$CH_2$" and substitute therefor --$CH_3$--.

Column 47, line 30, after "enylmethyl" insert --tetrazole--.

Column 49, line 5, delete "(46 mL";

UNITED STATES PATENT AND TRADEMARK OFFICE
CERTIFICATE OF CORRECTION

PATENT NO. : 5,554,624
DATED : September 10, 1996
INVENTOR(S) : Carmen Almansa, et al.

It is certified that error appears in the above-indentified patent and that said Letters Patent is hereby corrected as shown below:

line 19, delete "4.14" and substitute therefor --4.15--;

line 46, after "Hz" (1st ocurr) should read -- 3H,$CH_3$), 2.57 (s, 3H, $CH_3$), 2.62 (s, 3H, $CH_3$), 2.80 (q, J=7.5Hz, -- line 47, after "$CH_2$)," should read -- 5.48 (s, 2H, $CH_2$), -- line 62, delete "Propionitrile" and substitute therefor --propionitrile--.

Column 51, line 12, delete "3 2.83" and substitute therefor --2.83--;

line 14, delete "5.51 (s, 0.5X2H, $CH_2$),".

Column 52, line 8, delete "imidazole" and substitute therefor --imidazo--;

line 14, delete "$^1$-NMR" and substitute therefor --$^1$H-NMR--;

line 17, delete "0.55" and substitute therefor --0.5--;

line 23, delete "3-[[3-(2-Cyano-1-phenylvinyl)" and substitute therefor -- 3[[4-(2-Cyano-2-hydroxymethyl-1-phenylethyl --

UNITED STATES PATENT AND TRADEMARK OFFICE
CERTIFICATE OF CORRECTION

PATENT NO. : 5,554,624
DATED : September 10, 1996
INVENTOR(S) : Carmen Almansa, et al.

It is certified that error appears in the above-indentified patent and that said Letters Patent is hereby corrected as shown below:

Column 53, line 32, delete "2.36" and substitute therefor --2.32--;

line 51, after "phenyl " delete "]".

Column 59, line 13, after "Hz" delete ")";

line 15, after "7.5(" insert --m--.

Column 60, lines 22 and 23 delete in their entirety;

line 66, delete "4.27" and substitute therefor --4.37--;

line 67, delete "Pry" and substitute therefor --Pyr--.

Column 62, line 18, delete ")q" and substitute therefor --(q--.

Column 63, line 35, delete "Pry" and substitute therefor --Pyr--.

Column 66, line 21, delete "4" and substitute therefor --5--;

line 38, delete "21.5" and substitute therefor --21.4--;

lines 61-62, delete "0.5X2H, $CH_2$), 4.10 (q, J-7.5 Hz,".

UNITED STATES PATENT AND TRADEMARK OFFICE
CERTIFICATE OF CORRECTION

PATENT NO. : 5,554,624
DATED : September 10, 1996
INVENTOR(S) : Carmen Almansa, et al.

It is certified that error appears in the above-indentified patent and that said Letters Patent is hereby corrected as shown below:

Column 67, line 43, delete "3" and substitute therefor --63--;

line 63, after "imidazo" insert --[--.

Signed and Sealed this

Sixth Day of May, 1997

Attest:

Attesting Officer

BRUCE LEHMAN

Commissioner of Patents and Trademarks